(12) United States Patent
Fan et al.

(10) Patent No.: US 10,980,428 B2
(45) Date of Patent: Apr. 20, 2021

(54) WEARABLE PULSE WAVEFORM MEASUREMENT SYSTEM AND METHOD

(71) Applicant: ViviPulse, LLC, New Haven, CT (US)

(72) Inventors: Linran Fan, Pasadena, CA (US); Zhen Li, New Haven, CT (US); Peiyuan Mao, Chicago, IL (US); Peng Yuan, Mountain View, CA (US)

(73) Assignee: VIVIPULSE, LLC, New Haven, CT (US)

( * ) Notice: Subject to any disclaimer, the term of this patent is extended or adjusted under 35 U.S.C. 154(b) by 320 days.

(21) Appl. No.: 15/843,608

(22) Filed: Dec. 15, 2017

(65) Prior Publication Data

US 2018/0168466 A1    Jun. 21, 2018

Related U.S. Application Data

(60) Provisional application No. 62/434,949, filed on Dec. 15, 2016.

(51) Int. Cl.
*A61B 5/021* (2006.01)
*A61B 5/024* (2006.01)
*A61B 5/00* (2006.01)

(52) U.S. Cl.
CPC ...... *A61B 5/02108* (2013.01); *A61B 5/02416* (2013.01); *A61B 5/024* (2013.01); *A61B 5/681* (2013.01); *A61B 5/725* (2013.01); *A61B 5/7267* (2013.01); *A61B 5/7271* (2013.01); *A61B 5/7278* (2013.01)

(58) Field of Classification Search
CPC .......................... A61B 5/02416; A61B 5/1455
See application file for complete search history.

(56) References Cited

U.S. PATENT DOCUMENTS

| | | | |
|---|---|---|---|
| 5,431,170 A * | 7/1995 | Mathews | A61B 5/0002 600/323 |
| 5,588,425 A | 12/1996 | Sackner et al. | |
| 5,961,467 A * | 10/1999 | Shimazu | A61B 5/02116 600/485 |
| 6,058,331 A | 5/2000 | King | |
| 6,361,501 B1 | 3/2002 | Amano et al. | |
| 6,364,842 B1 | 4/2002 | Amano et al. | |
| 7,277,752 B2 | 10/2007 | Matos | |

(Continued)

FOREIGN PATENT DOCUMENTS

| | | |
|---|---|---|
| CN | 103135801 A | 6/2013 |
| EP | 0 947 160 A1 | 10/1999 |
| WO | 2012/037679 A1 | 3/2012 |

OTHER PUBLICATIONS

International Search Report for International Application No. PCT/US2017/066686 dated Apr. 16, 2018.

(Continued)

*Primary Examiner* — Puya Agahi
(74) *Attorney, Agent, or Firm* — McCormick, Paulding & Huber PLLC

(57) ABSTRACT

A pulse waveform measurement system includes an LED light source providing an incident beam having a predetermined wavelength onto a radial or other artery, samples reflected light at a predetermined sample rate, computes, and displays a pulse waveform and various parameters associated therewith. The wavelength and sample rate are set so as to provide desired data quality.

25 Claims, 48 Drawing Sheets

(56) References Cited

U.S. PATENT DOCUMENTS

| | | |
|---|---|---|
| 7,326,180 B2 | 2/2008 | Tanabe et al. |
| 7,465,274 B2 | 12/2008 | Amano et al. |
| 7,627,374 B1 | 12/2009 | Farazi et al. |
| 7,896,811 B2 | 3/2011 | Han et al. |
| 8,126,526 B2 | 2/2012 | Kitajima et al. |
| 8,301,215 B2 | 10/2012 | Lee et al. |
| 8,419,637 B2 | 4/2013 | Nielsen et al. |
| 8,773,239 B2 | 7/2014 | Phillips et al. |
| 2007/0135717 A1 | 6/2007 | Uenishi et al. |
| 2007/0225614 A1 | 9/2007 | Naghavi et al. |
| 2010/0042173 A1 | 2/2010 | Farazi et al. |
| 2010/0305412 A1 | 12/2010 | Darrah et al. |
| 2011/0028810 A1* | 2/2011 | Van Slyke ............. A61B 5/726 600/323 |
| 2011/0035222 A1 | 2/2011 | Schiller |
| 2012/0108928 A1 | 5/2012 | Tverskoy |
| 2013/0137945 A1* | 5/2013 | Addison ............ A61B 5/02416 600/323 |
| 2014/0073938 A1 | 3/2014 | Rodriguez-Llorente et al. |
| 2014/0249424 A1 | 9/2014 | Fan et al. |
| 2015/0031969 A1 | 1/2015 | Khair |
| 2015/0105637 A1 | 4/2015 | Yu et al. |
| 2015/0109124 A1 | 4/2015 | He et al. |
| 2015/0112154 A1 | 4/2015 | He et al. |
| 2015/0112155 A1 | 4/2015 | Bijjani et al. |
| 2015/0112156 A1 | 4/2015 | He et al. |
| 2015/0112157 A1 | 4/2015 | Bijjani et al. |
| 2015/0112158 A1 | 4/2015 | He et al. |
| 2015/0112159 A1 | 4/2015 | He et al. |
| 2015/0112208 A1 | 4/2015 | He et al. |
| 2015/0112452 A1 | 4/2015 | He et al. |
| 2015/0112606 A1 | 4/2015 | He et al. |
| 2015/0164351 A1 | 6/2015 | He et al. |
| 2015/0201876 A1 | 7/2015 | Zhou |
| 2016/0106325 A1 | 4/2016 | Kang et al. |
| 2016/0256116 A1* | 9/2016 | Baik ................... A61B 5/0059 |
| 2017/0143279 A1* | 5/2017 | Jayaraman ......... A61B 5/02405 |
| 2017/0196497 A1* | 7/2017 | Ray ........................ G16H 40/63 |
| 2017/0281024 A1 | 10/2017 | Narasimhan et al. |

OTHER PUBLICATIONS

Written Opinion for International Application No. PCT/US2017/066686 dated Apr. 16, 2018.

Li et al., "Forward and Backward Pressure Waveform Morphology in Hypertension", Hypertension—Pulse Wave Analysis, p. 375-381, Jul. 5, 2016.

Liu et al., "Modeling carotid and radial artery pulse pressure waveform by curve fitting with Gaussian functions", Biomedical Signal Processing and Control 8, p. 449-454, 2013.

Nitzan et al., "Pulse oximetry: Fundamentals and technology update", Medical Devices: Evidence and Research, p. 231-239, Jul. 2014.

Chen et al., "Estimation of Central Aortic Pressure Waveform by Mathematical Transformation of Radial Tonometry Pressure", American Heart Association, vol. 95(7): 1827-1836, Apr. 1, 1997.

Nelson et al., "Noninvasive Measurement of Central Vascular Pressures with Arterial Tonometry: Clinical Revival of the Pulse Pressure Waveform?", Mayo Clinic Proceedings, vol. 85(5), p. 460-472, May 2010.

Fan et al., "Pulse Wave Analysis", Advanced Biomedical Engineering, Aug. 23, 2011, Gaetano Gargiulo, IntechOpen, DOI: 10.5772/22600. https://www.intechopen.com/books/advanced-biomedical-engineering/pulse-wave-analysis.

O'Rourke et al., "Pulse wave analysis", British Journal Clinical (Research Methods in Human Cardiovascular Pharmacology), vol. 51, p. 507-522, 2001.

Shimizu et al., "Role of the augmentation index in hypertension", Therapeutic Advances in Cardiovascular Disease, vol. 2(1), p. 25-35, 2008.

Lee et al., "Role of High Augmentation Index in Spontaneous Intracerebral Haemorrhage", Asian Journal of Surgery, vol. 33—No. 1, p. 42-50, Jan. 2010.

Acampa et al., "Arterial Stiffness in Patients with Deep and Lobar Intracerebral Hemorrhage", Journal of Stroke, vol. 16(3), p. 184-188, 2014.

Shim et al., "Development of Heart Rate Monitoring for Mobile Telemedicine using Smartphone", Chwee Teck Lim, James C.H. Goh (Eds.): ICBME 2008, Proceedings 23, pp. 1116-1119, 2009.

* cited by examiner

| Time | Voltage Output |
|---|---|
| 2016/08/09 11:35:08:016 | 1251 |
| 2016/08/09 11:35:08:020 | 1249 |
| 2016/08/09 11:35:08:023 | 1248 |
| 2016/08/09 11:35:08:026 | 1309 |
| 2016/08/09 11:35:08:065 | 1312 |
| 2016/08/09 11:35:08:071 | 1314 |
| 2016/08/09 11:35:08:074 | 1402 |
| 2016/08/09 11:35:08:077 | 1399 |
| 2016/08/09 11:35:08:114 | 1402 |
| 2016/08/09 11:35:08:118 | 1403 |
| 2016/08/09 11:35:08:122 | 1370 |
| 2016/08/09 11:35:08:126 | 1364 |
| 2016/08/09 11:35:08:163 | 1366 |
| 2016/08/09 11:35:08:166 | 1365 |
| 2016/08/09 11:35:08:172 | 1279 |
| 2016/08/09 11:35:08:175 | 1275 |
| 2016/08/09 11:35:08:211 | 1274 |
| 2016/08/09 11:35:08:215 | 1271 |
| 2016/08/09 11:35:08:220 | 1229 |
| 2016/08/09 11:35:08:223 | 1224 |
| 2016/08/09 11:35:08:260 | 1223 |
| 2016/08/09 11:35:08:263 | 1223 |
| 2016/08/09 11:35:08:270 | 1200 |
| 2016/08/09 11:35:08:274 | 1200 |
| 2016/08/09 11:35:08:309 | 1201 |
| 2016/08/09 11:35:08:313 | 1203 |
| 2016/08/09 11:35:08:318 | 1210 |
| 2016/08/09 11:35:08:321 | 1211 |
| 2016/08/09 11:35:08:357 | 1209 |
| 2016/08/09 11:35:08:361 | 1208 |
| 2016/08/09 11:35:08:368 | 1199 |
| 2016/08/09 11:35:08:372 | 1195 |
| 2016/08/09 11:35:08:406 | 1196 |
| 2016/08/09 11:35:08:411 | 1198 |
| 2016/08/09 11:35:08:414 | 1197 |
| 2016/08/09 11:35:08:418 | 1197 |
| 2016/08/09 11:35:08:455 | 1195 |
| 2016/08/09 11:35:08:458 | 1198 |
| 2016/08/09 11:35:08:461 | 1195 |
| 2016/08/09 11:35:08:464 | 1196 |
| 2016/08/09 11:35:08:504 | 1196 |
| 2016/08/09 11:35:08:507 | 1196 |
| 2016/08/09 11:35:08:511 | 1214 |
| 2016/08/09 11:35:08:514 | 1216 |
| 2016/08/09 11:35:08:553 | 1216 |
| 2016/08/09 11:35:08:557 | 1214 |
| 2016/08/09 11:35:08:560 | 1254 |
| 2016/08/09 11:35:08:563 | 1254 |
| 2016/08/09 11:35:08:601 | 1255 |
| 2016/08/09 11:35:08:604 | 1257 |
| 2016/08/09 11:35:08:607 | 1301 |
| 2016/08/09 11:35:08:610 | 1304 |
| 2016/08/09 11:35:08:655 | 1304 |
| 2016/08/09 11:35:08:659 | 1306 |
| 2016/08/09 11:35:08:663 | 1609 |
| 2016/08/09 11:35:08:668 | 1631 |
| 2016/08/09 11:35:08:699 | 1640 |
| 2016/08/09 11:35:08:703 | 1654 |
| 2016/08/09 11:35:08:706 | 2919 |
| 2016/08/09 11:35:08:709 | 2970 |
| 2016/08/09 11:35:08:748 | 2990 |
| 2016/08/09 11:35:08:751 | 3014 |
| 2016/08/09 11:35:08:753 | 3073 |
| 2016/08/09 11:35:08:755 | 3063 |
| 2016/08/09 11:35:08:797 | 3057 |
| 2016/08/09 11:35:08:803 | 3052 |
| 2016/08/09 11:35:08:807 | 3083 |
| 2016/08/09 11:35:08:812 | 3068 |
| 2016/08/09 11:35:08:853 | 3056 |
| 2016/08/09 11:35:08:859 | 3054 |
| 2016/08/09 11:35:08:866 | 2519 |
| 2016/08/09 11:35:08:869 | 2475 |
| 2016/08/09 11:35:08:894 | 2459 |
| 2016/08/09 11:35:08:900 | 2437 |
| 2016/08/09 11:35:08:903 | 1472 |
| 2016/08/09 11:35:08:909 | 1449 |
| 2016/08/09 11:35:08:943 | 1435 |
| 2016/08/09 11:35:08:946 | 1424 |
| 2016/08/09 11:35:08:951 | 993 |
| 2016/08/09 11:35:08:953 | 990 |
| 2016/08/09 11:35:08:992 | 983 |
| 2016/08/09 11:35:08:995 | 981 |
| 2016/08/09 11:35:08:999 | 1005 |
| 2016/08/09 11:35:09:002 | 1012 |

FIG. 4

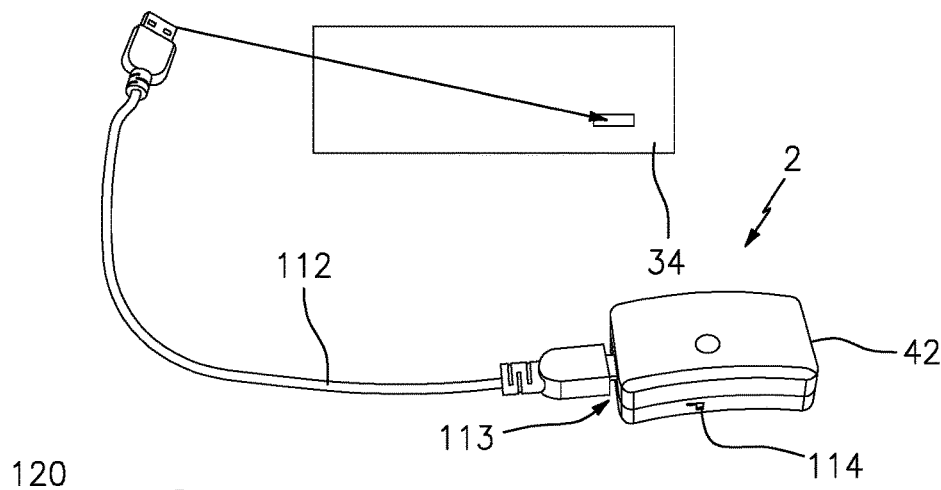
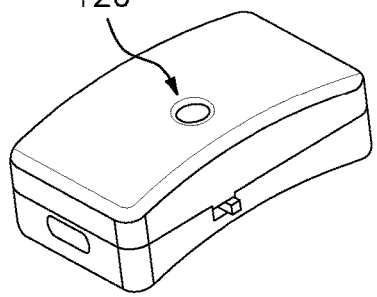
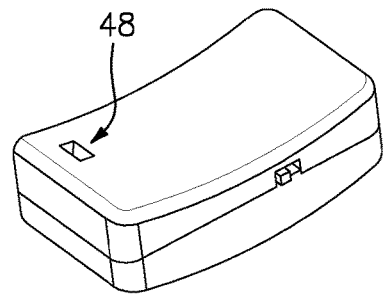
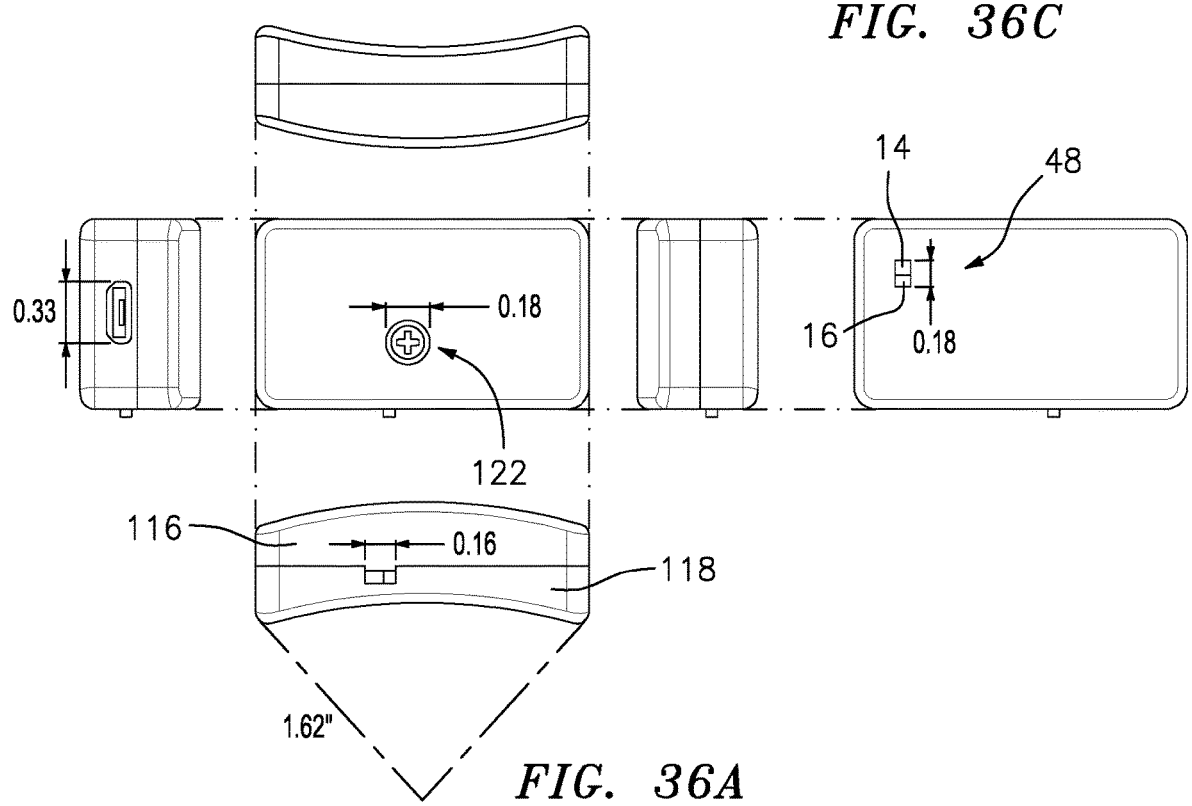
FIG. 35
FIG. 36B
FIG. 36C
FIG. 36A

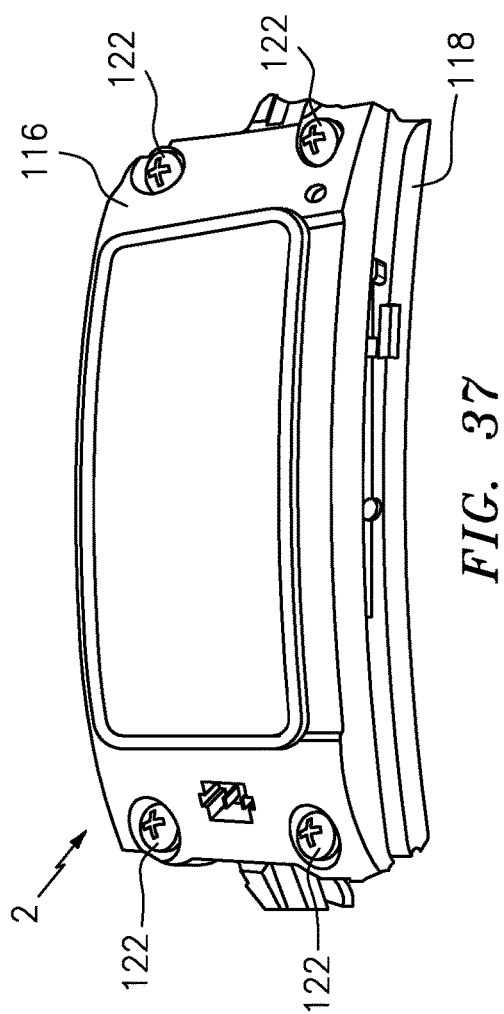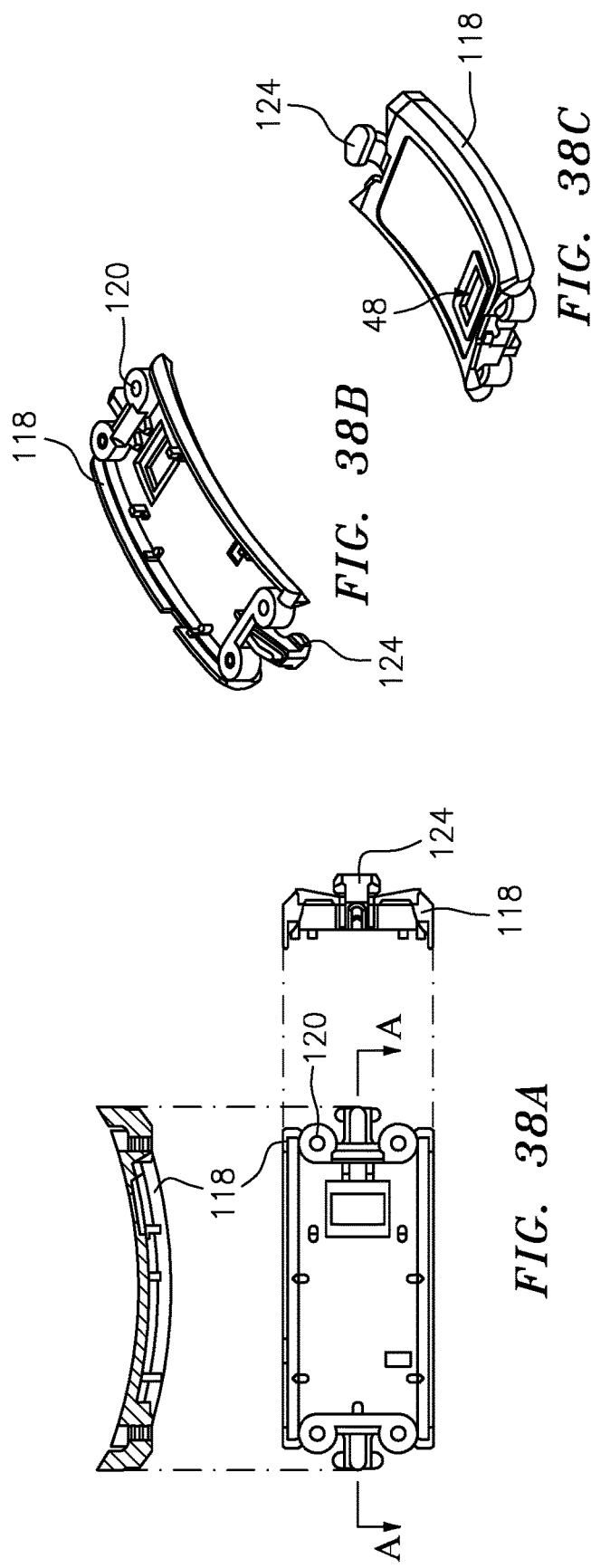

| Pulse Type | Description | Physiological cause | Possible Disease |
|---|---|---|---|
| Normal | Prominent peaks, Stable heart rate, Consistent pulse waveform | N/A | N/A |
| Small and Weak | No diastolic peak, Weak systolic peak | Decreased stroke volume | Heart failure, hypovolemia, severe aortic stenosis |
| | | Increased peripheral resistance | |
| Large and Bounding | No diastolic peak, Strong systolic peak | Increased stroke volume | Fever, anemia, hyperthyroidism, aortic regurgitation, bradycardia, heart block, atherosclerosis |
| | | Decreased peripheral resistance | |
| | | Decreased compliance | |
| Bisferiens (biphasic pulse) | double systolic peak | Increased arterial pulse with double systolic peak | Aortic regurgitation, aortic stenosis and regurgitation, hypertrophic cardiomyopathy |
| Alternating pulses (pulsus alternans) | Abnormal ratio between peaks, Unstable amplitude | Pulse amplitude varies from peak to peak, rhythm basically regular | Left ventricular failure |

FIG. 46

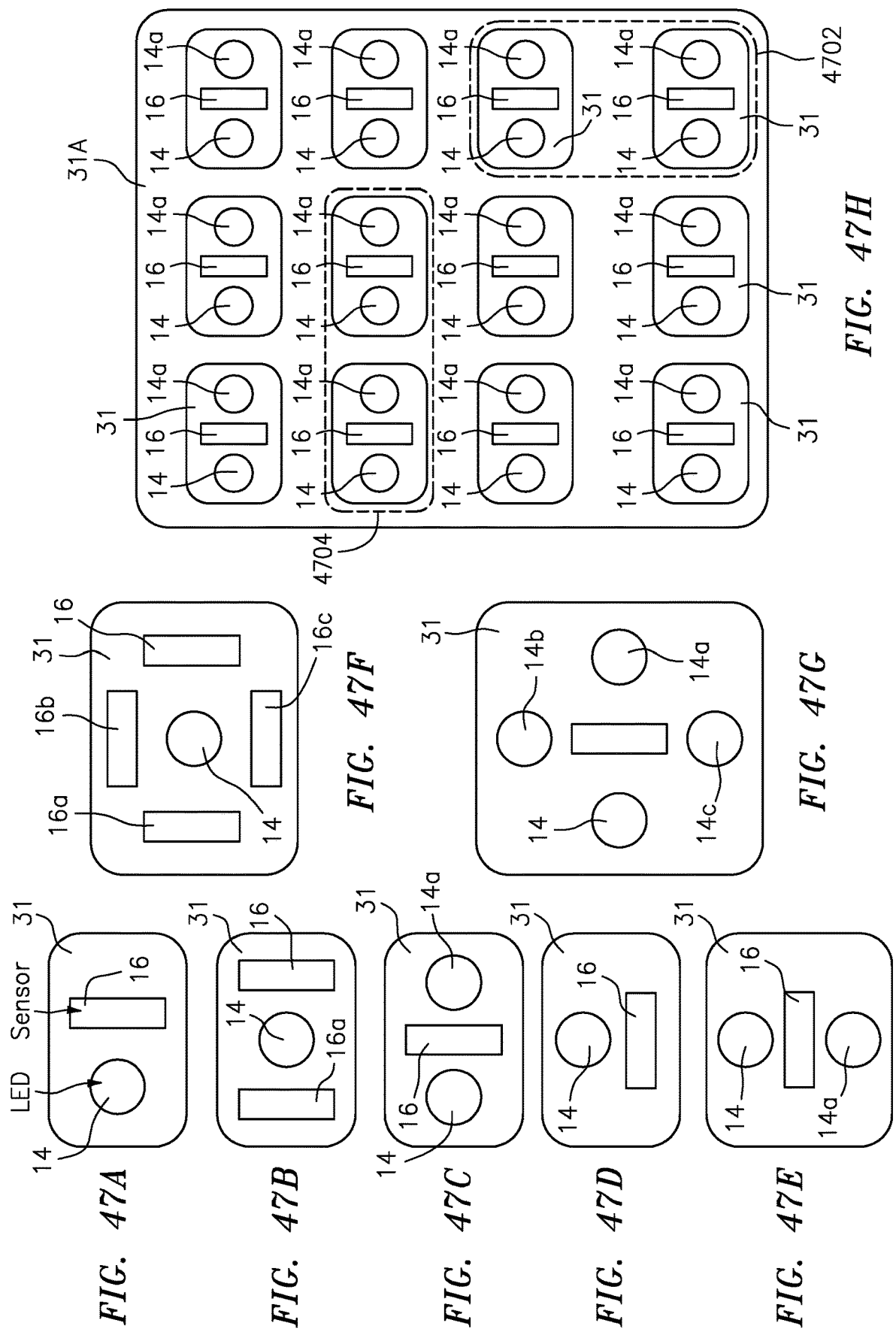

4900

PWM App Settings

Display Format: ⟵ 4902
- ☐ Show Pulse Rate
- ☐ Show Pulse Waveform graph
- ☐ Show Pulse Waveform parameters
- ☐ Show Health Parameters
- ☐ Show Healthy/Abnormal Status
- ☐ Show Blood Pressure
- ☐ Show Blood Pressure Change/Details
- ☐ Show Comparison to Normal/Healthy users
- ☐ Show Aggregate User Data by:
    - ☐ Age; ☐ Health History; ☐ Location; ☐ Conditioning

User Attributes/Characteristics: ⟵ 4904
- ☐ DOB: __/__/____    ☐ Male  ☐ Female
- ☐ Age Group: ☐ <18; ☐ 18-21; ☐ 22-30; ☐ 31-40; ☐ 41-50; ☐ 51-60; ☐ 61-70; ☐ >70
- ☐ Location/Home Address: __City X, State Y__ <>(drop-down)
- ☐ Health History:__(Conditions, Medications, etc)__<>(drop-down)
- ☐ Conditioning:___(Run, Lift, Bike, etc.)__<>(drop-down)
- ☐ Last BP:____/____; Date:__/__/____ (may auto-populate)
- ☐ Alow receipt of data (BP, Other)

Alert Settings: ⟵ 4906
- ☐ Alerts On
- ☐ Alert me when an Abnormal Status/Data occurs relating to:
    - ☐ BP  ☐ PWM Params  ☐ Health Params  ☐ Healthy/Abnormal
    - ☐ Pulse Rate  ☐ Urgent Event (Heary Attack, Stroke, Other)
- ☐ Also Alert:  ☐ Doctor_____;  ☐ 911;  ☐ Hospital;
    - ☐ Family/Friend _____
- ☐ Alert me when to get BP measured

*FIG. 49*

WEARABLE PULSE WAVEFORM MEASUREMENT SYSTEM AND METHOD

CROSS-REFERENCE TO RELATED APPLICATION

This application claims the benefit of U.S. Provisional Patent Application No. 62/434,949 filed Dec. 15, 2016, the contents of which are incorporated herein by reference in their entirety to the extent permitted under applicable law.

BACKGROUND

While fingertip and earlobe pulse oximeters measure general oxygen levels, they do not provide the fidelity to measure a pulse waveform. Accordingly, there is a need for an improved measuring system to provide a high fidelity pulse waveform.

BRIEF DESCRIPTION OF THE DRAWINGS

FIG. 4 is a table of exemplary measurements from the PWM device and a timestamp of those measurements, i.e., pulse waveform data, collected in accordance with embodiments of the present disclosure.

FIG. 35 is a perspective view of a PWM device connected to a connector cable, in accordance with embodiments of the present disclosure.

FIG. 36A is top, front, inverted back, left side, right side and bottom views of a PWM device, in accordance with embodiments of the present disclosure.

FIG. 36B is perspective view of a PWM device, in accordance with embodiments of the present disclosure.

FIG. 36C is an inverted perspective view of a PWM device, in accordance with embodiments of the present disclosure.

FIG. 37 is a perspective view of a PWM device in accordance with embodiments of the present disclosure.

FIG. 38A is top, side and cross-section across A-A views of a bottom section of a PWM device in accordance with embodiments of the present disclosure.

FIG. 38B is a perspective view of a bottom section of a PWM device in accordance with embodiments of the present disclosure.

FIG. 38C is an inverted perspective view of a bottom section of a PWM device in accordance with embodiments of the present disclosure.

FIG. 46 is an illustration of possible pulse waveform irregularities, and diseases associated with the irregularities, that may be displayed by a PWM application implemented on a user device, in accordance with embodiments of the present disclosure.

FIGS. 47A, 47B, 47C, 47D, 47E, 47F, 47G, 47H are sensor and LED configurations on, for example, a printed circuit board in accordance with embodiments of the present disclosure.

FIG. 49 is a screen illustration of a settings screen for setting options for the PWM software application (PWM App), in accordance with embodiments of the present disclosure.

DETAILED DESCRIPTION

Figure 1C:
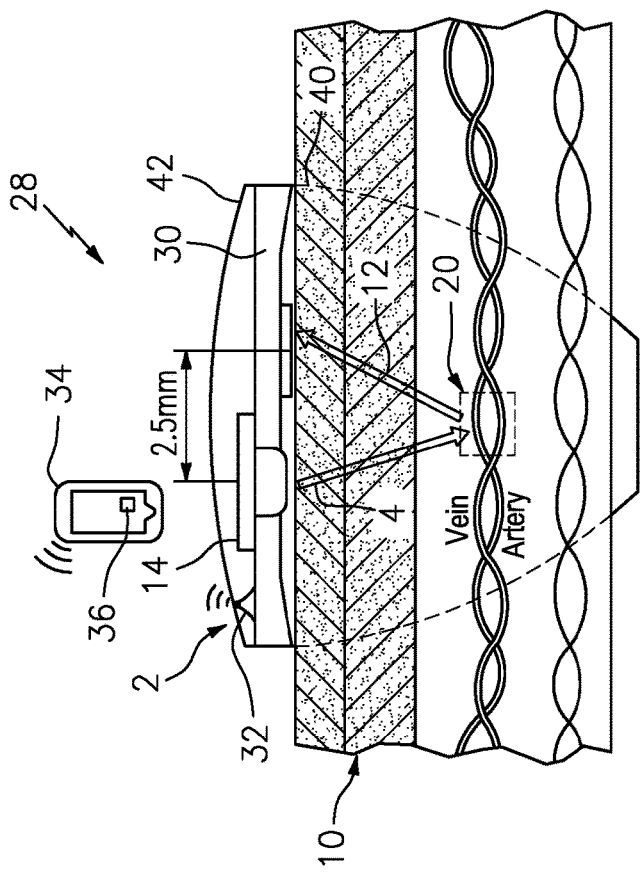
FIG. 1C is an enlarged cut-away view of an exemplary PWM device including a light emitting diode, an optical sensor, and a band encircling the user's arm, in accordance with embodiments of the present disclosure.
Figure 1A:
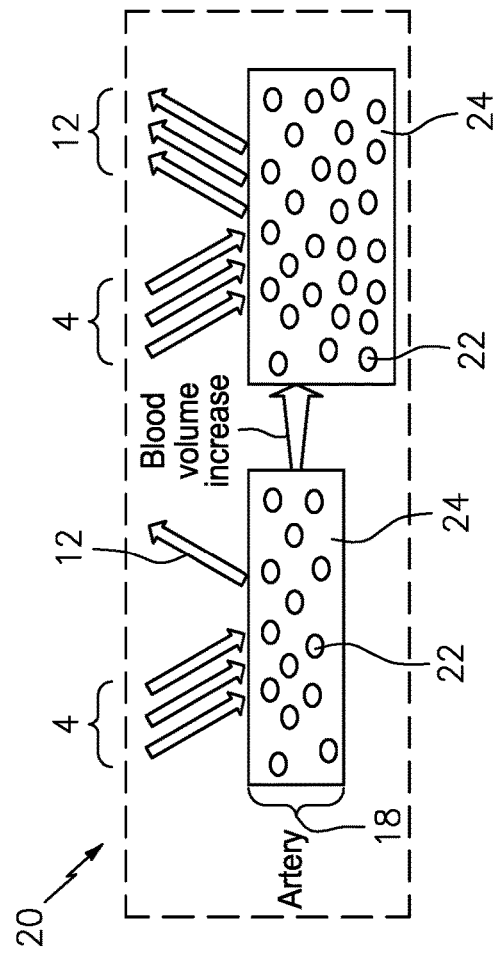
FIG. 1A is a cut-away view of a user's arm where an exemplary pulse waveform measurement (or PWM) device transmits light within the user's arm and detects reflection of the light, in accordance with embodiments of the present disclosure.

Referring to FIG. 1A, a pulse waveform measurement (or PWM) device 2 transmits an incident light 4 through an epidermis 6 layer and dermis layer 8 into a hypodermis layer 9 of an arm 10 and detects a reflected light 12 by the same PWM device 2.

In some embodiments, the PWM device 2 includes a light emitting diode ("LED") 14 (also shown in various embodiments as D2) adapted to transmit the incident light 4 and an optical sensor 16 (also shown in various embodiments as U5) configured to receive the reflected light 12.

In some embodiments, there may be more than one LED 14, such as, for example, two LEDs 14, 14*a* (also shown in various embodiments as D2 and D3) adapted to transmit the incident light 4. In some embodiments, the optical sensor 16 may consist of more than one optical sensor, such as, for example, two sensors 16, 16*a* configured to receive the reflected light 12. Other configurations are also contemplated and discussed herein.

In some embodiments, the incident light 4 is a coherent light emanating from the LED 14 at a predetermined wavelength range, such as, in the visible green spectrum having a wavelength of 500-540 nm. In some embodiments, the light 4 is incoherent light. In some embodiments, the incident light 4 may be transmitted at a single wavelength of about 515 nm. Green light is particularly well suited because it has an absorption peak for blood. However, other possible wavelength ranges include approximately 650-700 nm and approximately 900 nm, as shown and discussed in FIG. 1 of *Pulse oximetry: Fundamentals and technology update*, which is incorporated herein by reference to the extent necessary to understand the present disclosure, may also be used provided they meet the function and performance requirements discussed herein. (See Nitzan M, Romero A, Koppel R., *Med Devices (Auckl)*. 2014 Jul. 8; 7:231-9. doi: 10.2147/MDER.S47319. eCollection 2014. Review).

The optical sensor 16 is adapted to receive the reflected light 12 from an angle relative to an artery 18 (such as a radial artery) or in a directly vertical position. Additionally, in some embodiments, the LED 14 and optical sensor 16 may share a transmitter/receiver so that the transmitted incident light 4 and the reflected light 12 occur at the same location.

Figure 1B:
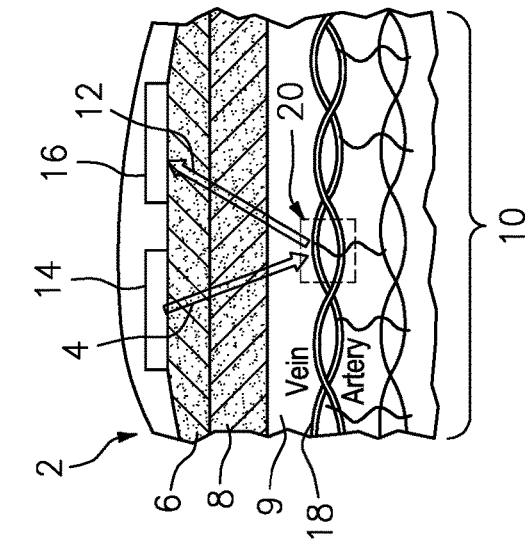
FIG. 1B is an enlarged view of an artery, showing light reflected from hemoglobin, in accordance with embodiments of the present disclosure.
Figure 22B:
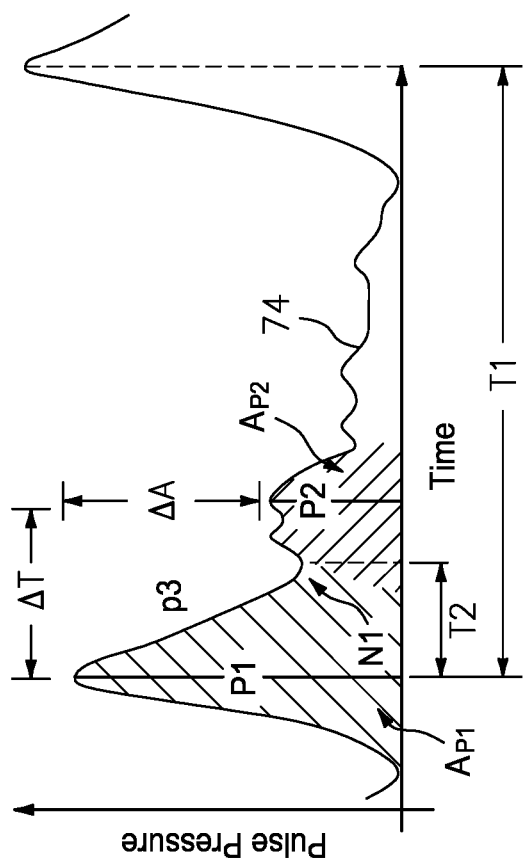
FIG. 22B is a line graph of a pulse waveform.
Figure 22A:
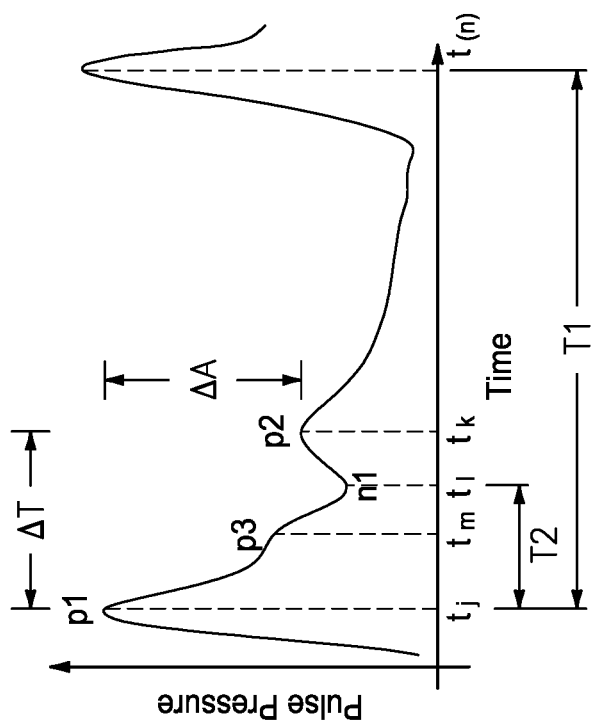
FIG. 22A is a line graph of a pulse waveform.

Referring to FIG. 1B, an enlarged view of a sensing or measurement location 20 of artery 18 illustrates that the intensity fluctuation of the reflected light 12 is indicative of a pressure pulse waveform (also referred to herein as a pulse waveform) as shown in FIGS. 22A and 22B. We believe the incident light 4 reflects off hemoglobin 22 present in blood 24, although other physiological factors may affect the reflectance. For example, the artery 18 wall may also influence the reflected light 12. As the blood volume oscillates with each heartbeat, the reflectance changes accordingly. A blood 24 volume increase correlates to more reflected light 12. This may be due to factors such as the increased amount of hemoglobin 22 and/or blood oxygenation levels.

Other physiological factors may affect the reflectance baseline. For example, skin color or the artery 18 wall may also influence the reflected light 12.

Referring to FIG. 1C, a pulse wave measurement (PWM) system 28 is shown. In some embodiments, the LED 14 and the optical sensor 16 are disposed on a printed circuit board 30. In various embodiments, the distance between the LED 14 and the optical sensor 16 is about 2.5 mm and has a near vertical (0 degree) incidence and reflectance angle. A slight angle may be used if desired, provided sufficient reflected light 12 is received at the sensor 16 to perform the functions as described herein.

In some embodiments, multiple LEDs (e.g., 14, 14a) are arranged opposite each side of the sensor 16 to provide increased source light and/or more evenly distribute light. In such embodiments, the sensor may be located directly above the sensing or measurement location 20 with LEDs 14 and 14a transmitting light at slight angles. The angled light 4 can meet at the sensing or measurement location 20, and reflect off hemoglobin as described herein. Other configurations are contemplated within the scope of the present disclosure and are described herein.

The printed circuit board 30 may be approximately 2.5 cm width by 2.5 cm length and have a height of about 1.0 cm. Other dimensions may be used if desired, provided they meet the functions and performance requirements described herein.

In some embodiments, the printed circuit board 30 may be two circuit boards 30, 31, with, for example, LEDs 14, 14a and/or optical sensors 16, 16a disposed on one circuit board 31 and various electrical hardware disposed on another printed circuit board 30. Details of embodiments with a two circuit board 30, 31 design are discussed herein.

The PWM device 2 may further include an antenna 32 (also shown in various embodiments as E1 or A1) capable of Bluetooth® transmission to a user device 34 (also referred to in certain embodiments as 61). In some embodiments, transmission to the user device 34 may occur through near field communication (NFC), Wi-Fi or radio frequency identification (RFID). The user device 34 may be a cellular telephone, smart phone, e-reader, set-top box, wireless mobile device, Bluetooth® hub, cloud storage device, computer, laptop, tablet or the like, or any combination thereof.

In some embodiments, the user device 34 is configured to run a pulse waveform measurement (PWM) software application (or PWM App.) 36, which is configured to process, calculate and/or display sampled pulse waveform data received by the user device, as described herein.

Figure 40:
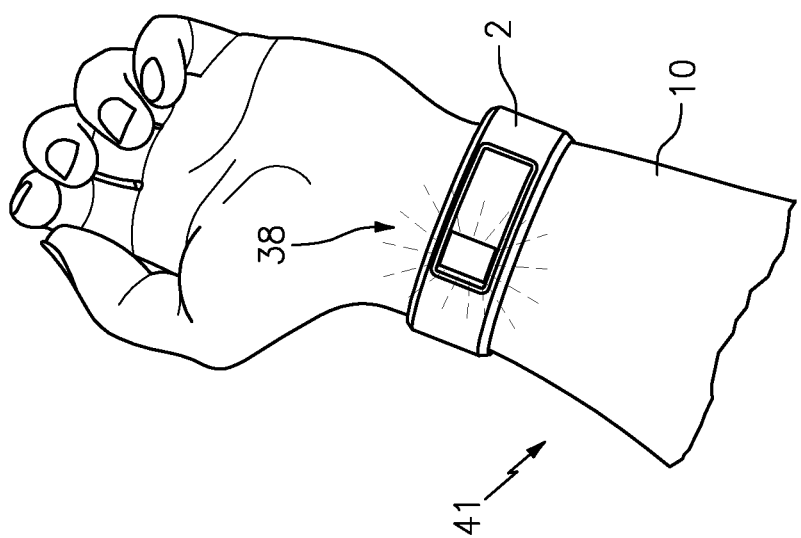
FIG. 40 is a perspective view of a PWM device in use on a user's arm in accordance with embodiments of the present disclosure.

The PWM device 2 may be positioned in various locations on the body, for example, on either side of the arm 10, and more specifically, secured flat against the anterior portion of a wrist 38. A band 40 can accomplish such positioning on a user 41 (illustrated in FIG. 40). In some embodiments, the PWM device 2 may be secured within the band 40. In some embodiments, the band 40 adheres to a casing 42 of the PWM device 2, specifically at sides 46 of the casing 42, and is configured to allow the incident light 4 to pass unobstructed, such as through an opening 48 on the casing 42 of the PWM device 2.

Hence, the user 41 can wear the PWM device 2 in a manner similar to that of wearing a watch, a wristband or any article of clothing, or garment adapted to be worn on the arm 10 of the user 41. The user 41 can wear the PWM device 2 while performing any routine and ordinary operation the user 41 would otherwise perform in everyday life, such as walking, running, cycling and so forth.

Figure 2:
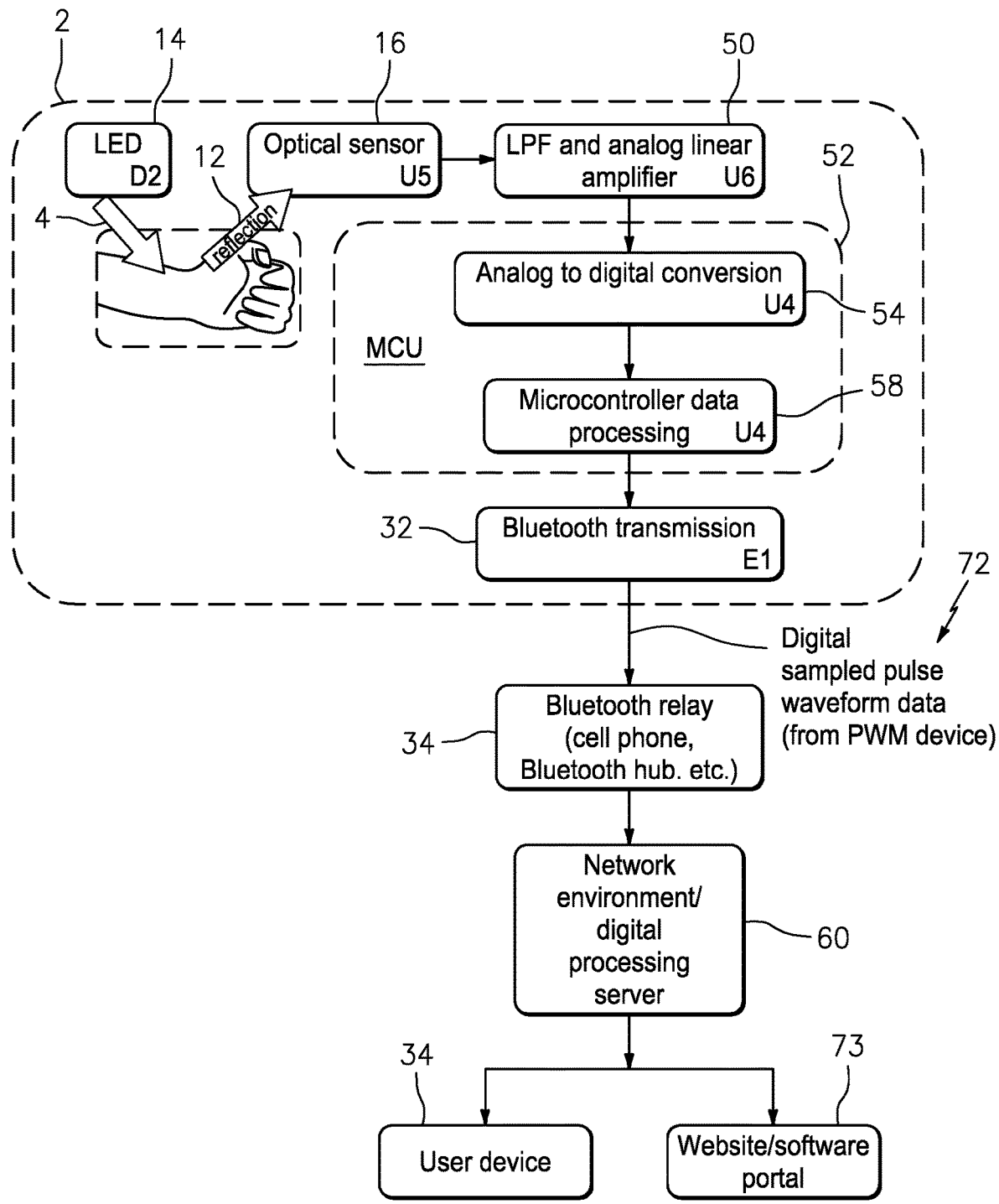
FIG. 2 is a block diagram showing hardware involved in light signal processing, amplification, conversion, and storage in accordance with embodiments of the present disclosure.
Figure 3:
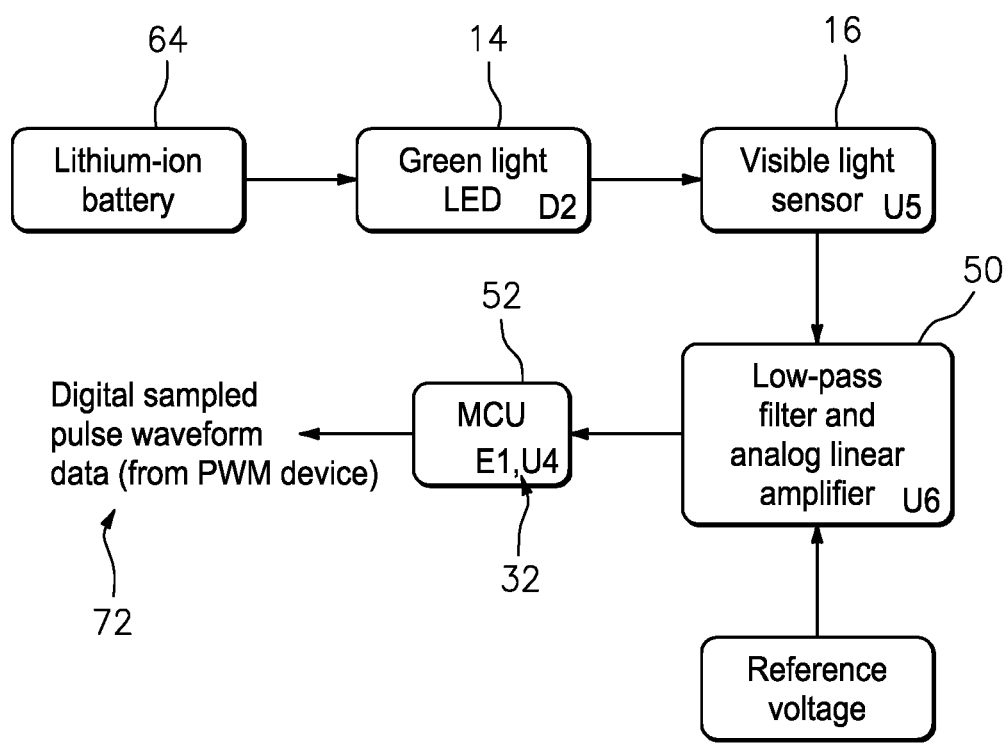
FIG. 3 is a hardware block diagram showing certain electronic circuit components utilized in the process of FIG. 2, in accordance with embodiments of the present disclosure.

Referring to FIGS. 2 and 3, in some embodiments the PWM device 2 transmits the incident light 4 via the LED 14 (D2) and receives the reflected light 12 at the optical sensor 16 (U5). The optical sensor 16 (or, in some embodiments, sensors) provides an electrical signal indicative of the measured reflected light 12 to a combination low-pass filter (LPF) and analog linear amplifier 50 (U6). The LPF aspect of the LPF and analog linear amplifier 50 removes or attenuates frequencies of the input signal above 4 Hz (i.e. the filter breakpoint), and may be a single order low pass filter or other filter. The linear amplifier aspect of the LPF and analog linear amplifier 50 amplifies the low pass filtered analog voltage signal, for example, using a gain of 20 db. The amplified signal is provided to a microcontroller unit (MCU) 52 (U4). The MCU 52 samples the analog voltage signal using a built-in analog to digital (A/D) converter 54 within the MCU 52. The MCU 52 performs an (A/D) conversion step at a predetermined sample rate 56 (shown in FIGS. 25A-25C and discussed herein) to create a digital signal which may be stored in the MCU built-in memory. In some embodiments, the MCU (or other processor or component) may directly transmit, either wirelessly or by wired connection, the analog PWM signal (e.g., the low pass filtered PWM signal). The digitized (or analog) data signal may further be transmitted via Bluetooth® transmission by the antenna 32 (E1, A1) to a network environment 60, such as a server cloud, wireless personal area network, i.e., a Bluetooth® low energy, Bluetooth® smart network or to a wireless connected network or server, such as a network cloud server. Further details of the network environment 60 are discussed with regards to FIG. 39.

The digitized pulse waveform data may be also be transmitted to the network environment 60 via the user device 34. The user device 34 can display the processed pulse waveform data and further transmit it to the network environment 60 for storage, further processing, or access by others. In some embodiments, the user device 34 can display the processed data received from the network environment 60.

Referring to FIG. 3, in some embodiments a battery 64, such as a lithium-ion battery, provides power to the LED 14 (D2); the optical sensor 16 (U5); the LPF and analog linear amplifier 50 (U6); the MCU 52 (U4); the antenna 32 (E1); and other hardware components. The MCU 52 (U4) includes several areas of built-in memory and the A/D converter 54 as discussed above. In some embodiments, other microcontrollers or microprocessors may be used if desired, provided they meet the functions and performance requirements described herein.

Referring to FIG. 4, an exemplary table of sampled data results is shown. The optical sensor 16 provides filtered and amplified analog voltage signal indicative of the reflected light 12 which is then sampled by the A/D converter 54 in the MCU 52 at the predetermined sample rate 56. The A/D converter 54 records the sampled digital voltage output reading 66 and a time measurement 68 and stores the information on an on-board memory unit of the A/D converter 54. The digital voltage output readings 66 are integers, ranging from 0 to 4095, which are proportional to the analog voltage range of 0V to approximately 3.7V. When the digital voltage measurements 66 are graphed against the time measurements 68, a repeating sampled pulse waveform 72 results, for example, as shown in FIG. 25B (sampled at about 68 Hz). The sampled voltage measurements are also referred to herein as sampled pulse waveform data 72 and/or sampled pulse waveform data stream/readings 72. A theoretical pulse waveform 74 is illustrated in FIGS. 22A and 22B and further described with reference to FIG. 23.

Mathematically, the sampled pulse waveform data stream 72 can be described as a function y=f(t), where independent variable t represents time, and dependent variable y represents the collected voltage output readings 66. While there is a specific unit associated with the measurements from the PWM device 2 (i.e., the intensity of the reflected light 12), the precise values of the readings are not particularly significant for data analysis since the readings are sensitive to many environmental variables that are not controllable, such as ambient lighting. Thus, the data analysis focuses on the relative variations of the peaks and troughs shown in the repeating sampled pulse waveforms 72 and further explained with regards to FIGS. 5, 6, 7, 8A, 8B, 8C, 9, 10, 11, 12, 13, 14, 15, 16A, 16B, 17, 18, 19, 20, 21, 22A, 22B, 23, 25A, 25B and 25C.

Figure 5:
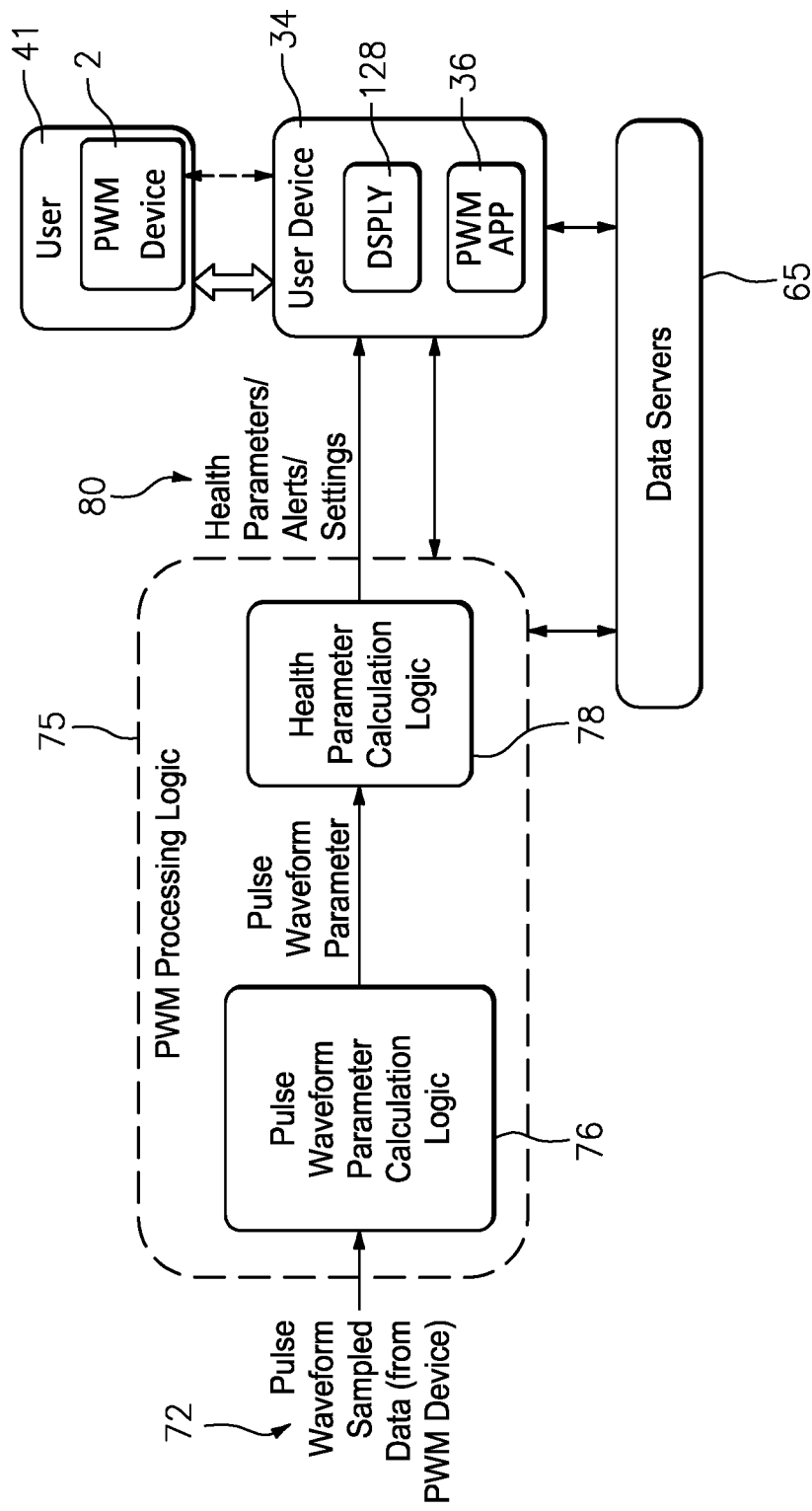
FIG. 5 is a block diagram showing digital data processing of the sampled pulse waveform data, including pulse waveform parameter calculation logic and health parameter calculation logic, in accordance with embodiments of the present disclosure.

Referring to FIG. 5, the sampled pulse waveform digital data 72 may be processed on or off the device 2 by digital data processing logic such as PWM processing logic 75. The PWM processing logic 75 uses pulse waveform parameter calculation logic 76 and health parameter calculation logic 78 to produce medically relevant health parameters 80 from the sampled pulse waveform digital data 72. Such health parameters may be calculated and/or stored continuously in real time by the system of the present disclosure.

Figure 6:
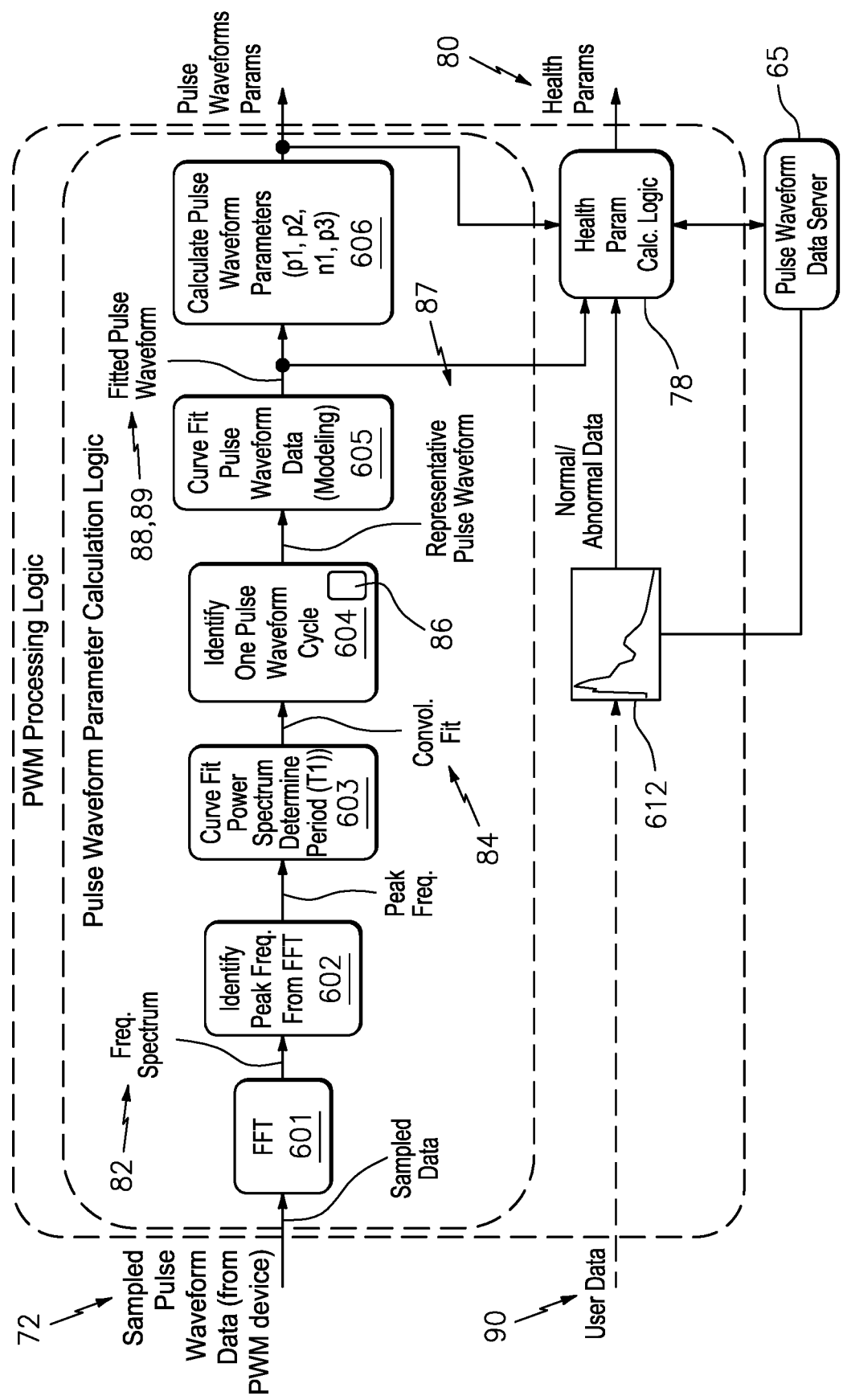
FIG. 6 is a flow diagram detailing the steps of the pulse waveform parameter calculation logic described in FIG. 5, in accordance with embodiments of the present disclosure.
Figure 11:
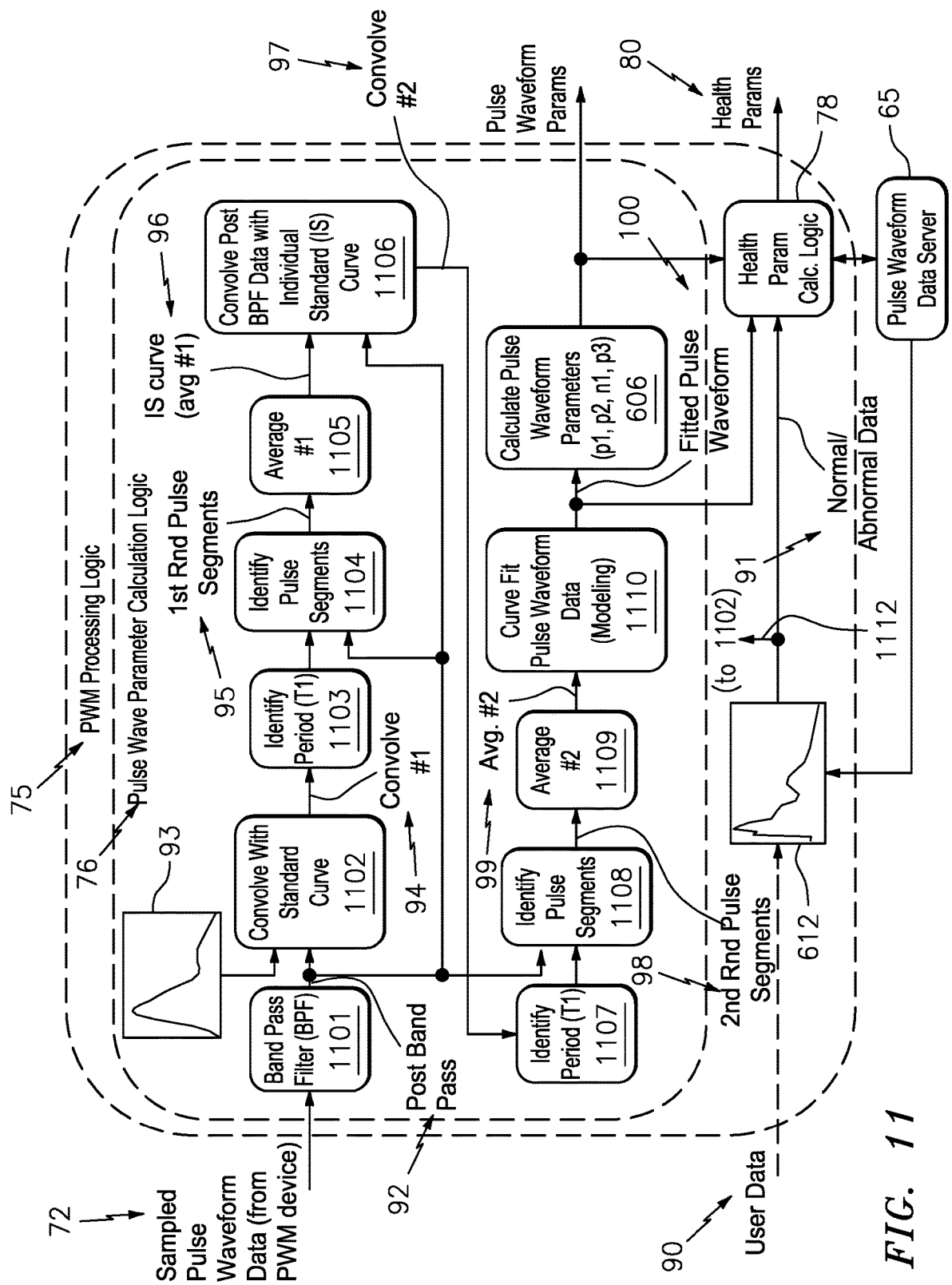
FIG. 11 is a flow diagram detailing steps of pulse waveform parameter calculation logic such as described in FIG. 5, in accordance with embodiments of the present disclosure.

The pulse waveform parameter calculation logic 76 includes a plurality of data processing steps and is further described with regards to FIGS. 6 and 11.

Fast Fourier Transform (FFT) Approach

Referring to FIG. 6, a section of the sampled pulse waveform data 72 (graphically illustrated in FIG. 7) undergoes several analysis steps. Each of the steps described herein (e.g. in FIGS. 6 and 11) may be performed by hardware, firmware or software logic or components or devices as described herein to perform the functions described herein. For example, a multi-step analysis sequence may be applied (or performed) by the pulse waveform parameter calculation logic 76, to extract pertinent information. The steps include:

1. Applying a Fast Fourier Transform, extracting a peak frequency, and curve fitting the power spectrum, illustrated in steps 601-603; and
2. Identifying a single pulse waveform representative sample, waveform modeling, and parameter extraction/calculation, illustrated in steps 604-606.

Details of these steps are provided below.

Applying a Fast Fourier Transform and Frequency Extraction

Figure 7:
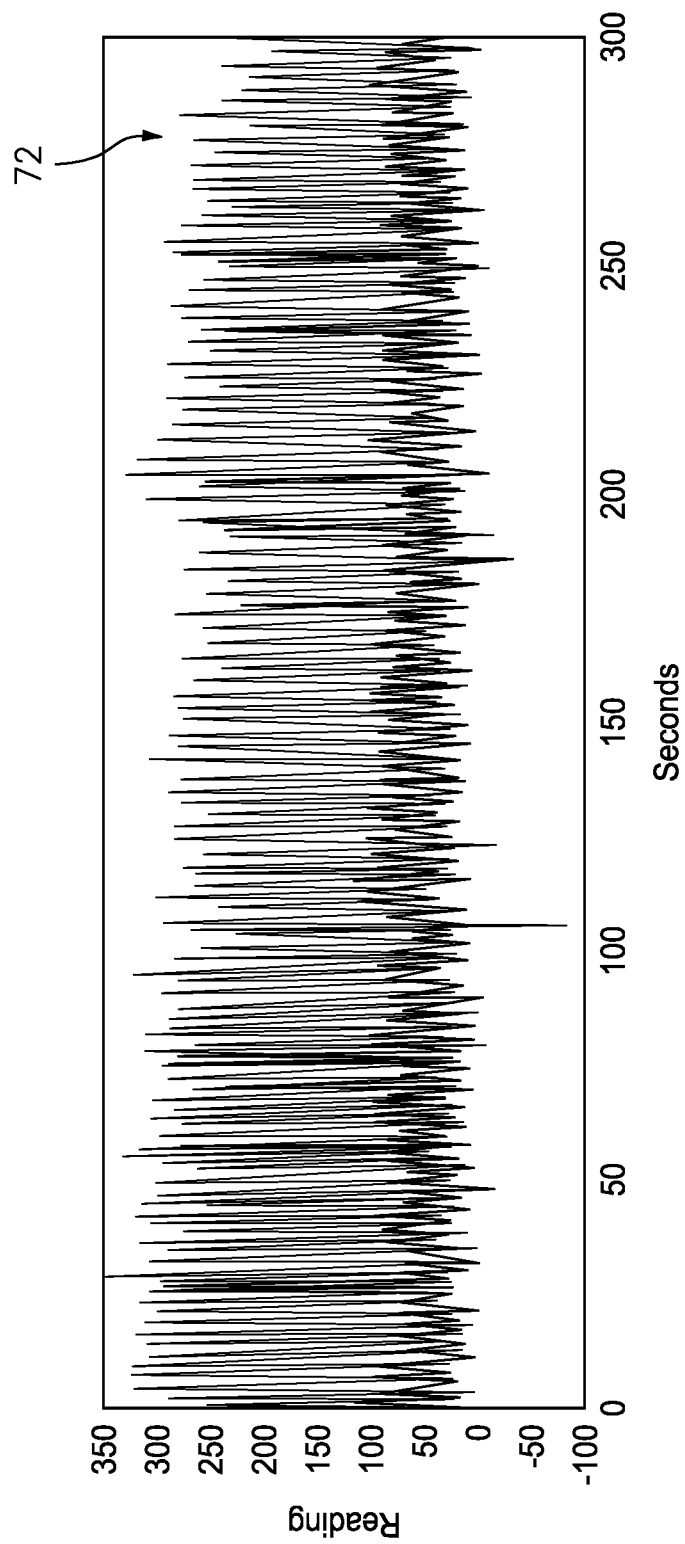
FIG. 7 is a three hundred second time plot of the pulse waveform data in accordance with embodiments of the present disclosure.
Figure 12:
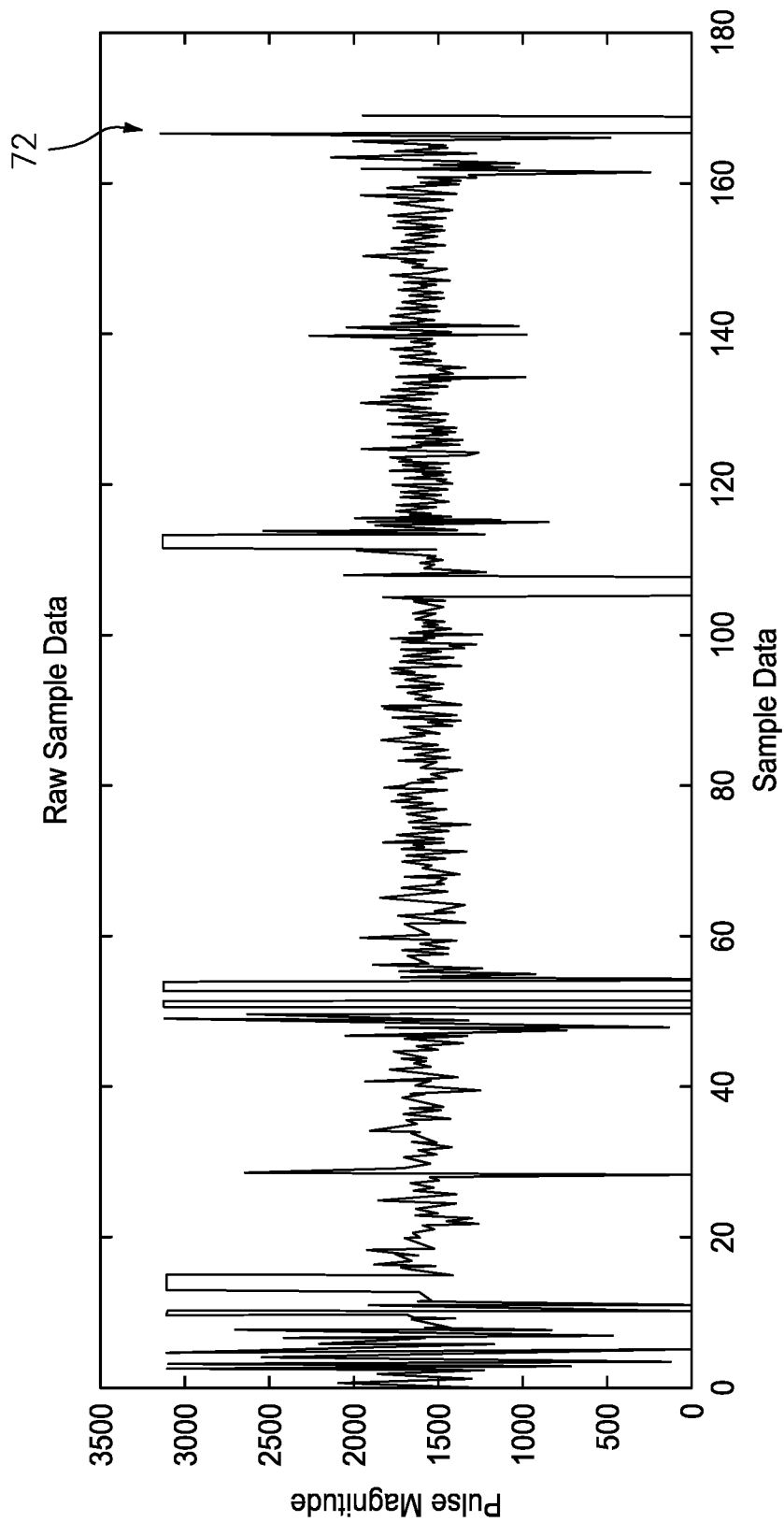
FIG. 12 is raw sampled pulse waveform data collected in accordance with embodiments of the present disclosure.
Figure 25A:
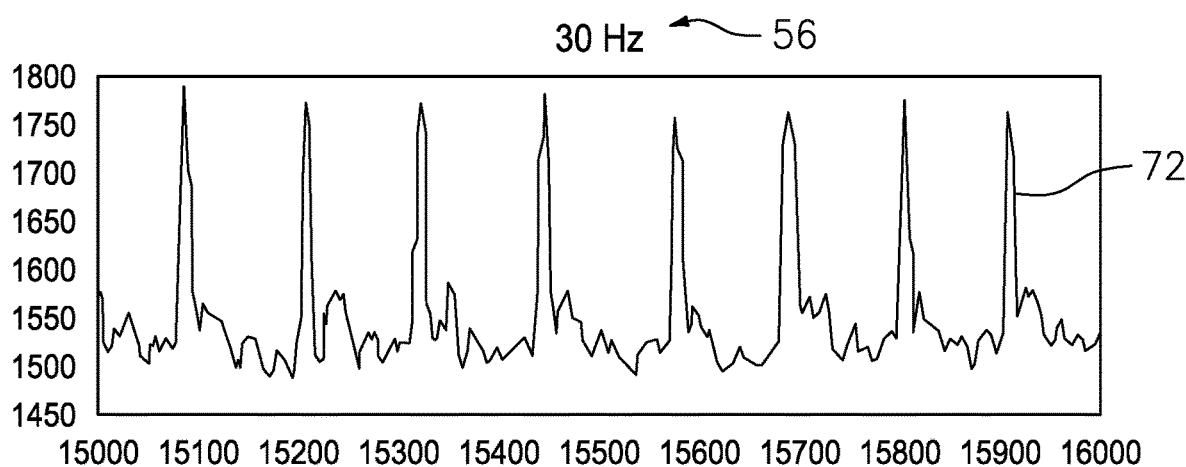
FIG. 25A is a graphical representation of pulse waveform data collected at a specified sampling rate, in accordance with embodiments of the present disclosure.
Figure 25B:
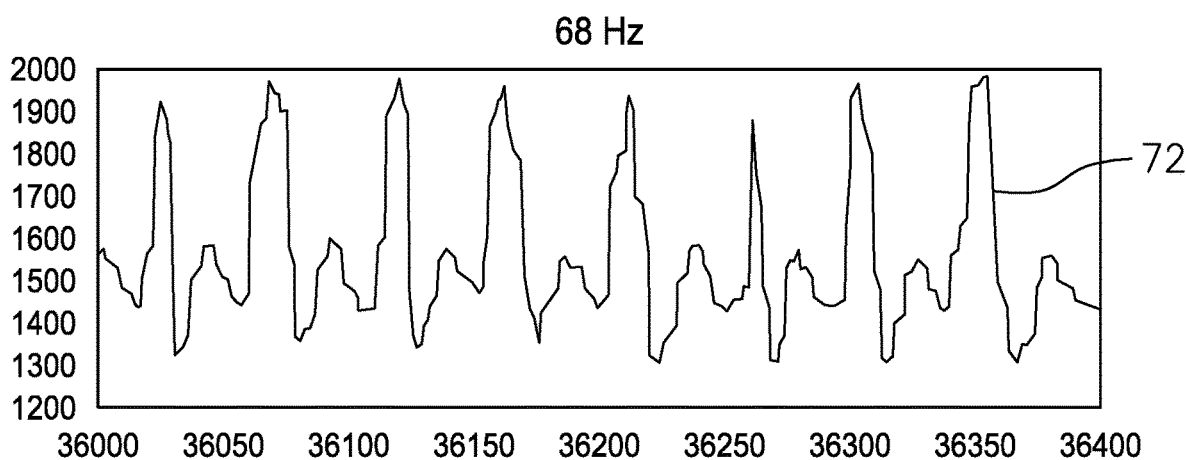
FIG. 25B is a graphical representation of pulse waveform data collected at a specified sampling rate, in accordance with embodiments of the present disclosure.

Noise and other systematic variations exist in the pulse waveform data stream 72 such as shown in FIGS. 7, 12 and 25A. To remove any periodic behavior with frequencies higher than the arterial pulses (normally in the range of 40-100 times per minute), the pulse waveform parameter calculation logic 76 performs a Fourier Transform (using a Fast Fourier Transform), as described below, to a section of the sampled pulse waveform data 72.

Generally, a Fourier Transform decomposes a function of time into the frequencies that make it up. It is a complex-valued function of frequency, whose magnitude (or absolute value) represents the magnitude of that frequency component present in the original function, and the complex argument is the phase offset of the basic sinusoid in that frequency.

Mathematically, $\hat{f}$, the Fourier transform of the function f, is denoted as:

$$\hat{f}(\xi) = \int_{-\infty}^{+\infty} f(t) e^{-2\pi i t \xi} \, dt, \tag{Eq. 1}$$

in which independent variable t represents time, and transform variable represents frequency. Since the pulse waveform data stream 72 comes in as a sequence of numbers, a discrete Fourier Transform (DFT) is applied to find the most dominant frequency in the waveforms 72, which corresponds to the arterial pulse among all kinds of longer-term variations and noises. In operation, the pulse waveform parameter calculation logic's 76 Fourier analysis utilizes an algorithm called the Fast Fourier Transform (FFT), which computes the discrete Fourier transform (DFT) of the original sequence (step 601) in a much shorter time compared with directly applying the mathematical formula defined above.

From the FFT, peak frequency can be identified (step 602), as described below.

Figure 8A:
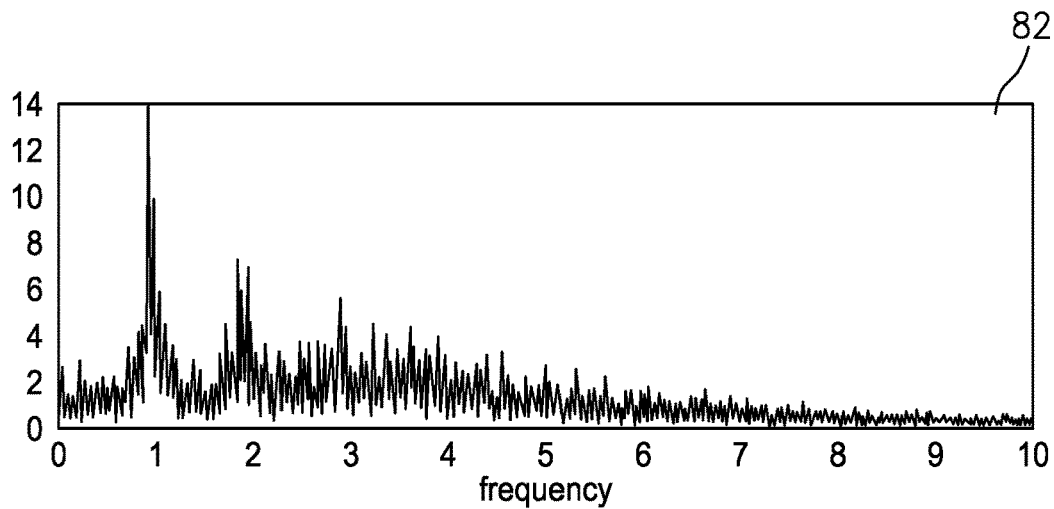
FIG. 8A is a power spectrum of FIG. 7, in accordance with embodiments of the present disclosure.

Referring to FIGS. 7 and 8A, 8B, and 8C, using a 300-second section of the pulse wave form data reading 72, a power spectrum 82 (FFT Data) including the frequency components and their magnitudes from the PWM device 2 readings is applied. The results are shown in FIG. 8A. The FFT Data allows for identification of the period (T1) as discussed herein and with regards to FIGS. 22A and 22B. Other sample time sections may be used if desired.

To find the most dominant frequency (i.e., peak frequency) in the pulse waveform data readings 72, a least squares fitting algorithm is applied to the power spectrum curve 82 of FIG. 8A.

Least squares fitting is a mathematical procedure for finding the best-fitting parameters of a proposed function to a given set of points by minimizing the sum of the squares of the offsets ("the residuals") of the points from the curve. Given a set of two-dimensional data points $(x_1, y_1), \ldots, (x_n, y_n)$ and a proposed functional form $f(x_i, a_1, a_2, \ldots, a_m)$ in which $(a_1, \ldots, a_m)$ are the parameters to determine, the best-fitting values are found when the expression $$\sum_{i=1}^{n} [y_i - f(x_i, a_1, a_2, \ldots, a_m)]^2 \tag{Eq. 2}$$

is minimized. Other fitting techniques, including those discussed herein, may also be used if desired.

Curve Fitting the Power Spectrum

Figure 8B:
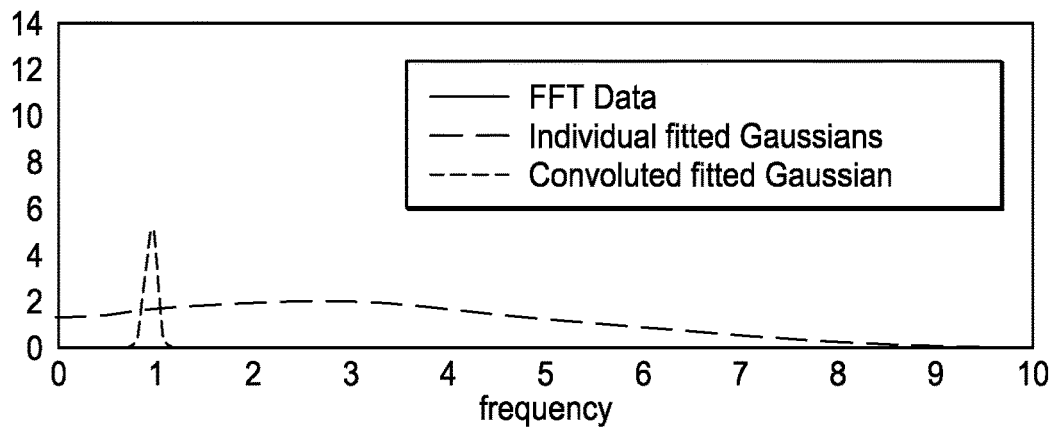
FIG. 8B is mathematical curves fitted to the power spectrum, in accordance with embodiments of the present disclosure.

To curve fit the power spectrum 82, in some embodiments a sum of n multiple Gaussian curves is used (step 603). A Gaussian curve centered at mean µ and standard deviation σ is simply expressed as $$f(x \mid \mu, \sigma^2) = \frac{1}{\sqrt{2\sigma^2\pi}} e^{-\frac{(x-\mu)^2}{2\sigma^2}}, \quad \text{(Eq. 3)}$$

and a proposed function of the present disclosure is therefore $$\sum_{1}^{n} A_i f(x \mid \mu_i, \sigma_i), \quad \text{(Eq. 4)}$$

with $A_i$'s being respective normalization constants. The number of Gaussian curves required to fit the power spectrum 82 varies among each data collection, and is subject to the particular user and the exact condition when the readings were taken. In FIG. 8B, the power spectrum 82 is best fit by two Gaussian curves, with a lower frequency component representing the arterial pulse at around 0.97 Hz, and a higher frequency noise at about 2.5 Hz.

Figure 8C:
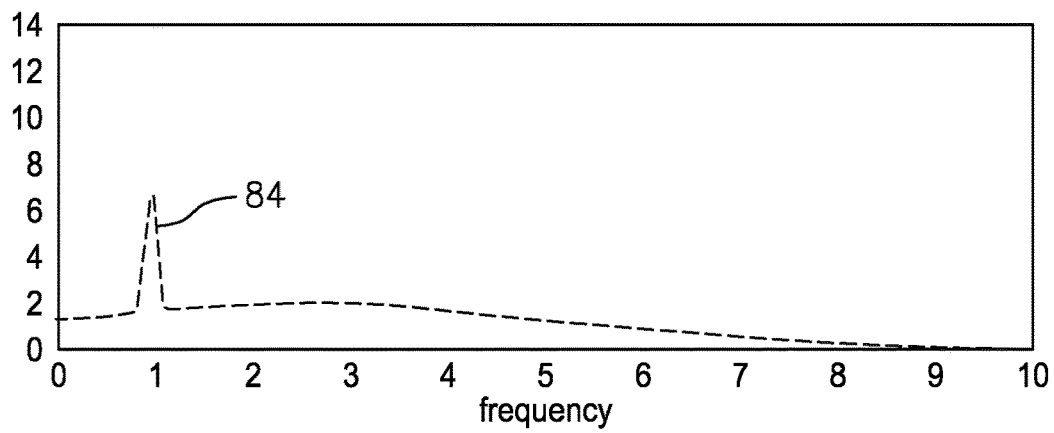
FIG. 8C is a convoluted curve based on the mathematical curves, in accordance with embodiments of the present disclosure.

As illustrated in FIG. 8C, mathematical addition of the two Gaussian curves results in a convoluted fitted Gaussian curve 84.

Figure 9:
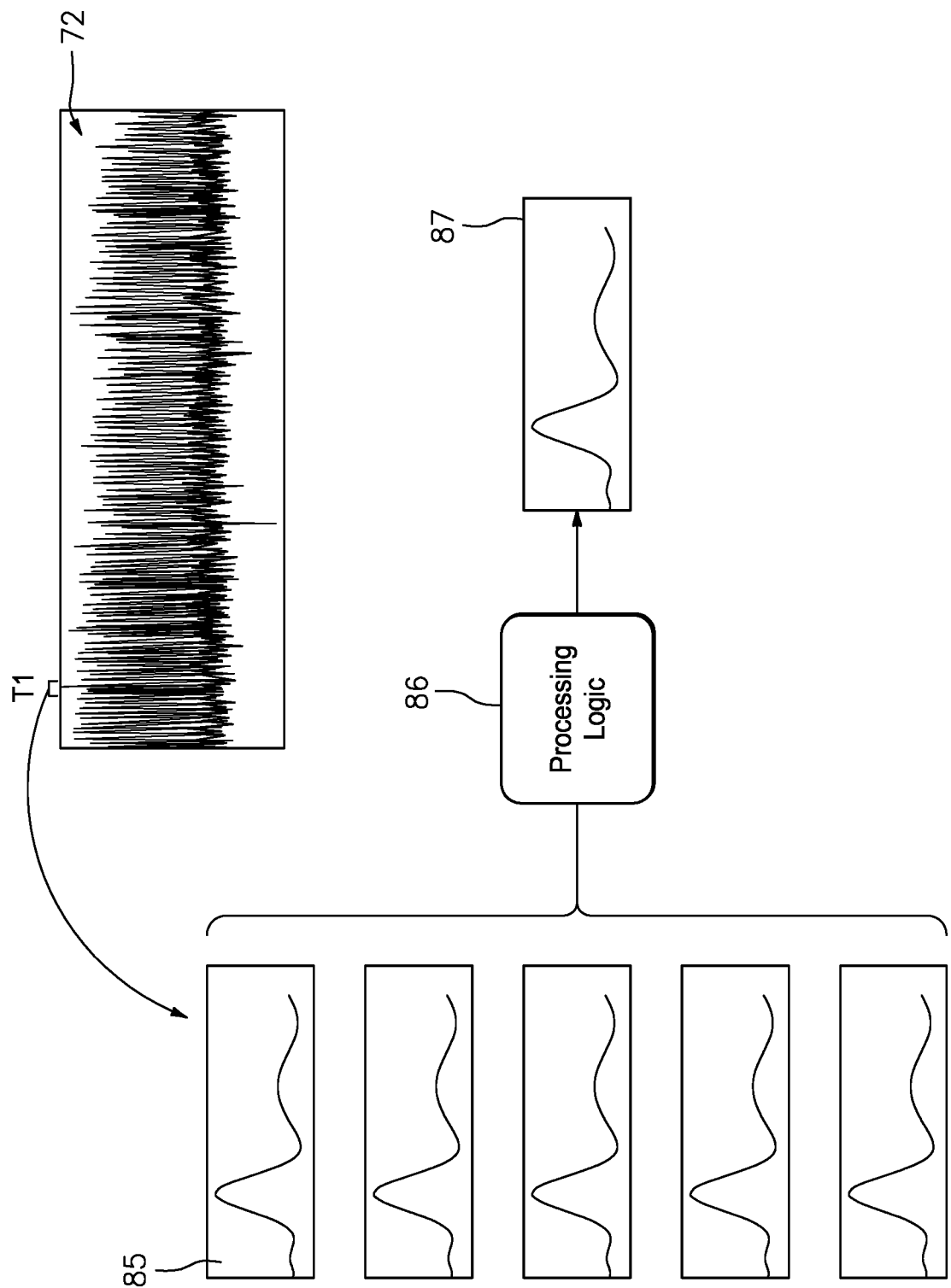
FIG. 9 is pictorial representation of averaged sampled pulse waveforms used produce a mathematically modified pulse waveform, in accordance with embodiments of the present disclosure.

Referring to FIGS. 6 and 9, at step 604, one sampled pulse waveform 85 of the pulse waveform data reading section (FIG. 7) is identified based on the above-calculated dominant frequency of the measured data stream 72, for example, by identifying the period (T1) and extracting an individual pulse waveform 85. This single sampled pulse waveform 85 serves as a representative sample used for further waveform modeling and parameter calculation by the pulse waveform parameter calculation logic 76. In some embodiments, an average (or median or other mathematical combination) of multiple (or even all) individually sampled pulse waveforms 85 of the measured data stream 72 can be compiled via processing logic 86 within logic 604 to produce an averaged single sampled pulse waveform 87.

Waveform Modeling

Referring to FIG. 6, at step 605, the sampled data is curve fit to a desired functional form that models a theoretical pulse waveform for the arterial pulse. Such theoretical pulse waveform curve, may be shown as a line graph 74 in FIG. 22A, which is similar to that shown in Chen et al., *Circulation*, 95(7), 1827-36, 1997.

Figure 10:
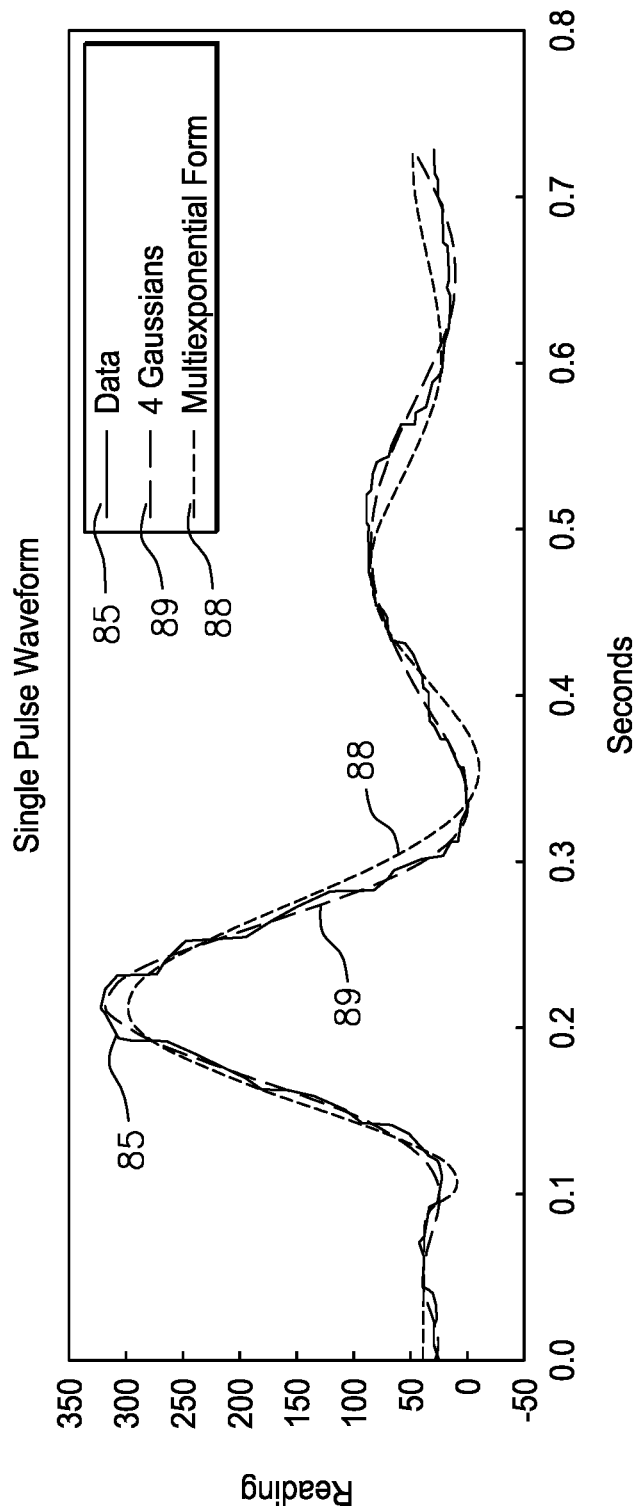
FIG. 10 is an example of a single calculated pulse waveform fitted to data according to two methods of the present disclosure, in accordance with embodiments of the present disclosure.

Referring to FIGS. 6 and 10, we have found that either a modified multi-exponential form 88 such as that described in Cohn et al. (*Hypertension* 1995; 26: 503-508), or a multi-Gaussian form 89 may be used to curve fit the pulse waveform data 72. Other curve fit equations or functions may be used if desired, including other exponential forms, provided they meet the function and performance requirements discussed herein.

The multi-exponential form 88 may be represented by the following equation:

$$f(t) = A_1 \exp(-A_2 t) + A_3 \exp(-A_4 t)\cos(A_5 t + A_6). \quad \text{(Eq. 5)}$$

We have found that modifying Eq. 5 by adding offsets in both the X- and Y-directions provides an acceptable fit. Thus, a unique function to the present disclosure is, $$f(t) = y_0 + A_1 \exp(-A_2(t-t_0)) + A_3 \exp(-A_4(t-t_0))\cos(A_5(t-t_0)+A_6). \quad \text{(Eq. 6)}$$

The multi-Gaussian form 89 of the present disclosure is a sum of four different Gaussian curves, with two of the Gaussian curves corresponding to the two peaks shown in FIG. 10. Along with a Y-axis offset, the equation for this function is $$f(t) = y_0 + \sum_{i=1}^{4} \frac{A_i}{\sqrt{2\sigma^2\pi}} \exp\left(-\frac{(t-\mu_i)^2}{2\sigma_i^2}\right). \quad \text{(Eq. 7)}$$

Theoretically, the data may be fit to only two Gaussian curves, with the rest of the graphed data being noise. In practice, however, we have found that using more than two Gaussian curves in the curve fit function produces better fits with lower sum of squares. Additionally, there may be other relevant health information that can be identified using more than two Gaussian curves, for example, contained within two additional peaks when using four Gaussian curves. Alternatively, three Gaussian curves may be used as described herein with FIG. 11, block 1110. Other numbers of Gaussian curves may be used if desired.

Similar to the "Applying a Fast Fourier Transform and Frequency Extraction" approach discussed herein above, a set of curve fit parameters (e.g. $A_1$-$A_6$, $y_o$ for Eq. 6; $A_i$, $y_o$ for Eq. 7) are calculated using a least-square fitting (or other curve fitting technique such as least absolute residual fitting) to the fitted multi-Gaussian form 89 (Eq. 7). Alternatively, a set of curve fit parameters may also be calculated using a least-square fitting (or other curve fitting technique) applied to the fitted Multiexponential form 88 (Eq. 6).

The curve fit parameters for the desired curve/function are then used to identify various pulse waveform (PWM) parameters (e.g. p1, p2, n1, p3) further described below in step 606 of FIG. 6.

Calculate Pulse Waveform Parameters

Referring to FIG. 6, at step 606, pulse waveform parameters (p1, p2, n1, and p3) as shown in the pulse waveform curve 74 (FIGS. 22A and 22B) may be calculated and updated continuously in real time from the curve fit parameters described above, as described below with regards to FIGS. 22A and 22B.

Figure 23:
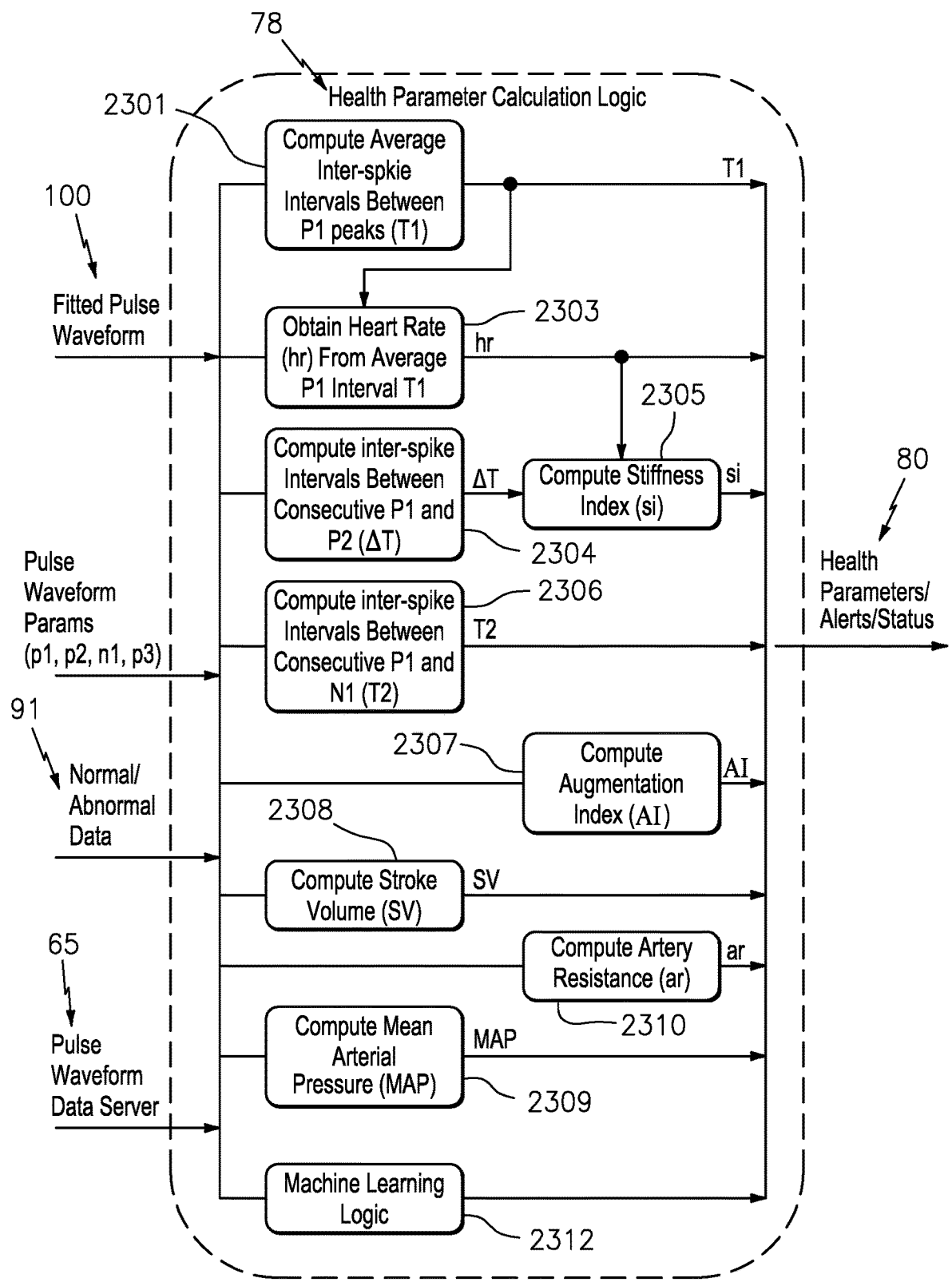
FIG. 23 is a flow diagram detailing the steps of health parameter calculation logic, such as described in FIG. 5, in accordance with embodiments of the present disclosure.

Referring to FIGS. 6 and 23, in some embodiments, instead of using the pulse waveform parameters (p1, p2, n1, p3) to derive health parameters 80, the system of the present disclosure may determine health status or conditions (e.g., normal or abnormal conditions or irregularities) directly using health parameter calculation logic 78. In that case, the logic 78 receives the PWM curve fit parameters discussed above and may continuously (or in real time) save such data on a server or database (e.g., such as a Pulse Waveform Data server 65 discussed hereinafter with regards to FIG. 39). The health parameter calculation logic 78 may also receive PWM curves, 612 from users (e.g. User 1-User N in FIG. 39) or user data 90, normal and/or abnormal pulse waveform data 91, or theoretical pulse waveform data, to train the health parameter calculation logic 78 to identify what curve fit parameters correspond to (or correlate to, or are predictive of, or are classified as) "normal" and "abnormal" conditions, and, if abnormal, what type(s) of abnormality(ies) exists (e.g., such as is shown in FIG. 46). Such correlations, or predictions, or classifications may be learned over time by machine learning logic 2312 using machine learning techniques and classifiers, such as support vector machines (SVMs), neural networks, decision tree classifiers, logistic regression, random forest, or any other machine learning or classification techniques that perform the functions of the present disclosure. The machine learning logic 2312 may also be used to determine other intermediate parameters, such as pulse waveform parameters (e.g., p1, p2, n1, p3) and/or other health parameters 80 (e.g. artery resistance, augmentation index, stiffness index, blood pressure).

The Health Parameter Calculation Logic 78 may also have alert logic that generates or sends alerts to the user device 34, 61 or to the PWM device 2, based on various predetermined health conditions or reminders. If the user settings have alerts activated, this logic determines whether the current PWM data or parameters, or PWM health parameters, or the like, matches the Alert Settings that the user has set up in the PWM App Settings (FIG. 49). If so, the logic sends a PWM Alert message to the user device or to the PWM device 2. The alert logic may be part of the machine learning logic 2312 or a separate logic component within the Health Parameter Calculation Logic 78. The alerts may also be part of the Health Parameters 80 provided by the Logic 78. Also, the machine learning logic 2312 may also learn over time what constitutes a health condition necessary to send an alert to the user.

In particular, the PWM alert message may be sent directly to the User Device 34 (e.g., text message or SMS or the like) or to a personal online account of the user, e.g., email or the like. If selected by the user, the alert may also be sent to the users Doctor, 911 emergency, hospital or family/friend, as indicated in the settings as discussed herein with FIG. 49. The graphical format and content of the PWM alert may be a pre-defined message, such as a pop-up box having text or graphics, such as: "A PWM Alert has occurred. Click this alert box to get more information," or it may specify the details, such as: "A PWM Alert has occurred regarding: An unsafe change in blood pressure. Click this alert box to get more information." In some embodiments, if the user clicks on the alert box, the PWM App is launched and the user can explore the PWM Alert in more detail, e.g., with the PWM GUIs discussed herein. Any other format and content for the PWMs alerts may be used if desired. The content and format of the PWM alert may also be set by the user if desired.

Also, user data 90 and the normal/abnormal pulse data 91, and curve/waveform 612 may be inputs for the logic 78. The user data 90 may encompass a wide variety of individual attributes that may affect (or help determine) the pulse waveform 74 such as age, height, weight, fitness level, ethnicity, DNA, geography, or any other personal attribute. The logic 78 may develop a normal range for certain parameters against which it compares new data collected to determine normal/abnormal conditions.

Convolve Approach

Referring to FIG. 11, in another approach of the present disclosure, e.g., an iterative time domain convolution technique, raw sampled pulse waveform data 72 (shown in FIG. 12) undergoes several analysis steps (or blocks or logic) to identify and extract the pulse waveform. An advantage of this approach is that the method is less sensitive to (1) noise, (2) shifting baseline, and (3) identifying erroneous multiple peaks as compared to isolating pulses from the raw sampled data trace (FIG. 12).

Figure 13:
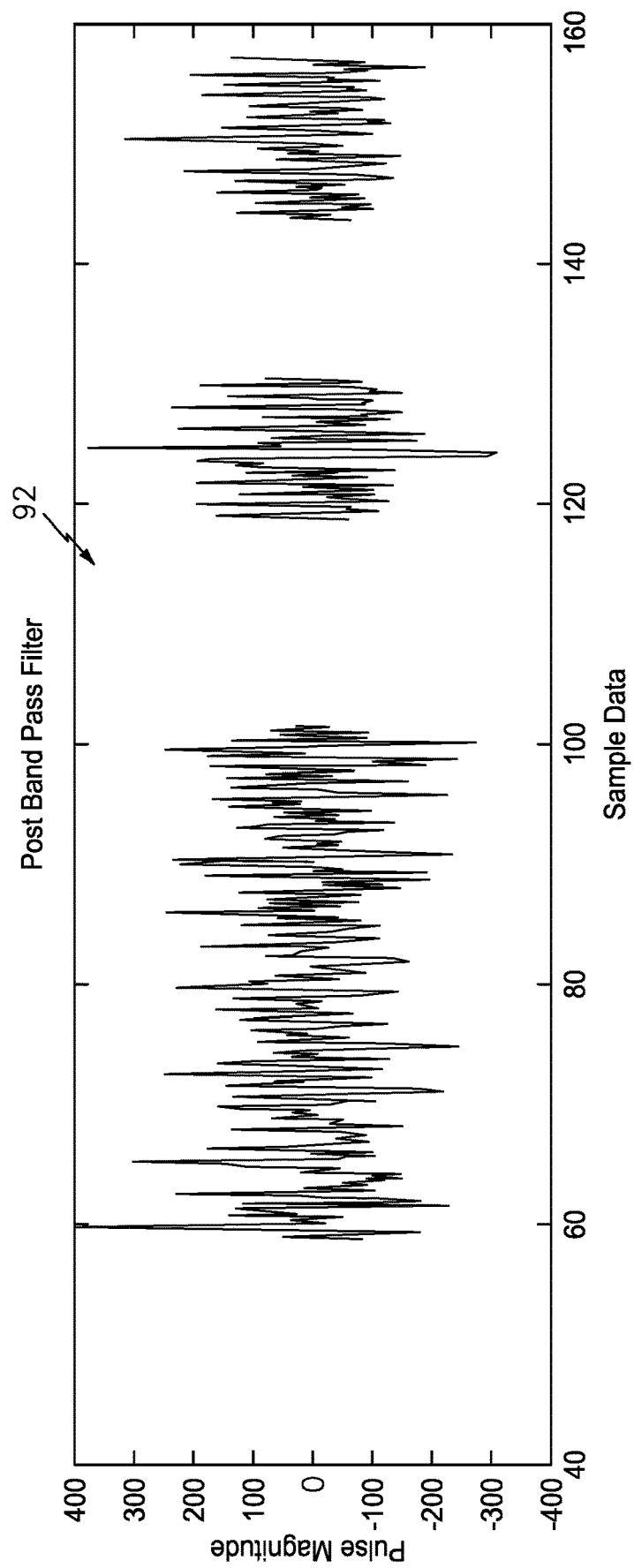
FIG. 13 is sampled pulse waveform data after a band pass filter has been applied, in accordance with embodiments of the present disclosure.
Figure 14:
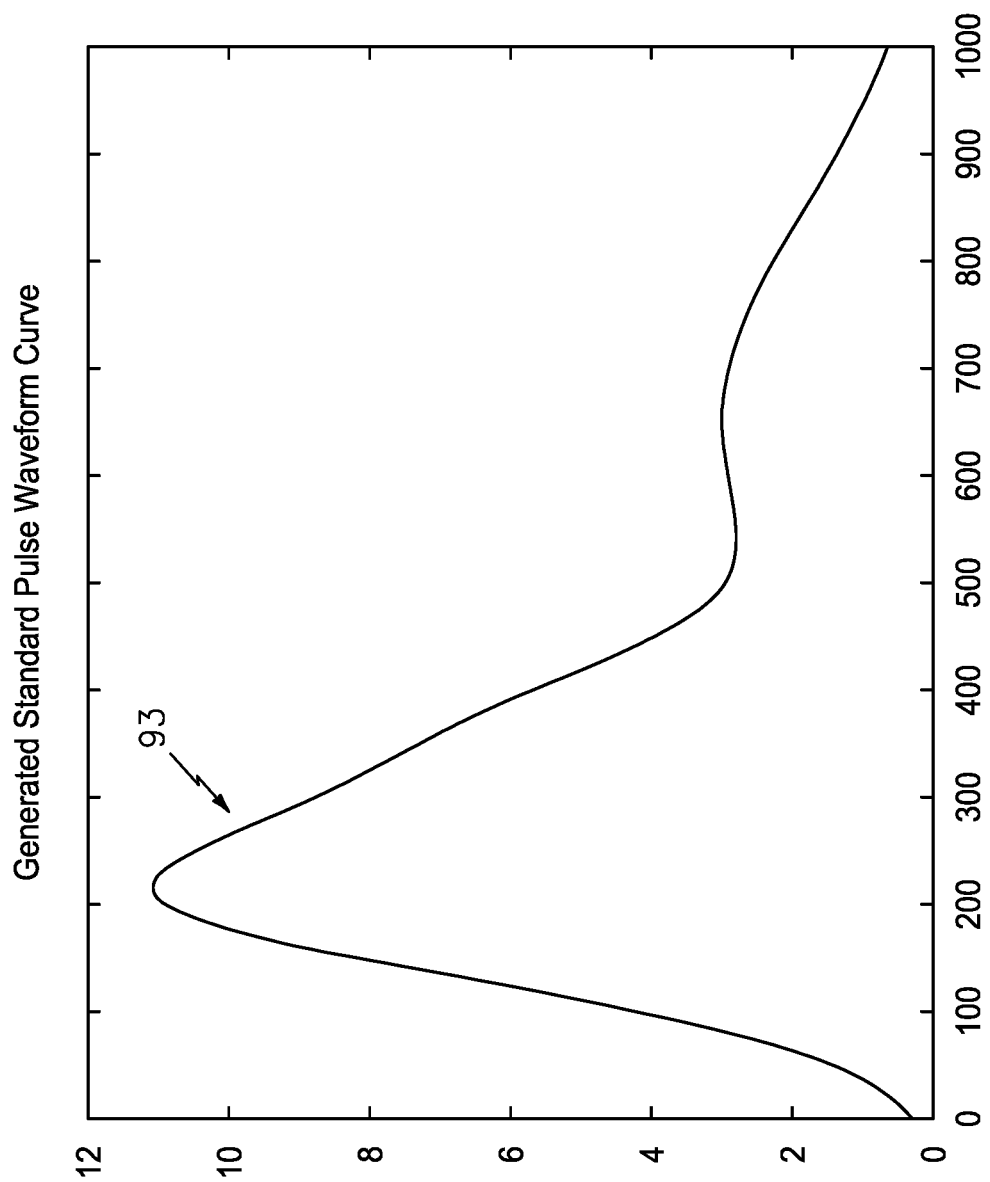
FIG. 14 is a standard curve generated from a simulation database for a "normal" pulse waveform, in accordance with embodiments of the present disclosure.

In particular, at block 1101, a digital band pass filter of about 0.5 to 3.5 Hz is applied to the sampled pulse waveform data 72 to produce post band pass filtered data 92, for example, as shown in FIG. 13.

At block 1102, the post band pass filtered data 92 is convolved (using digital convolution) with a "generated" standard pulse waveform curve 93. The generated standard pulse waveform curve 93 is a result of data provided by http://haemod.uk/virtual database. Radial and physiological data provided based on hemodynamic modeling from this website can be downloaded and averaged. An equation for generating this generated standard pulse waveform curve 93 is represented by:

$$\text{Raw\_standard} = 10 \cdot \exp(-0.5 \cdot ((x-200)/75)^2) + 5 \cdot \exp(-0.5 \cdot ((x-350)/75)^2) + 3 \cdot \exp(-0.5 \cdot ((x-650)/200)^2).$$ (Eq. 7.1)

In particular, the logic performs two convolutions of the input sampled PWM data, a first convolution with a "generated" standard curve, and a second convolution with the PWM output from the first pass through the logic. More than two convolutions may be done if desired. Alternatively, a singe convolution may be done to obtain the pulse waveform.

Figure 15:
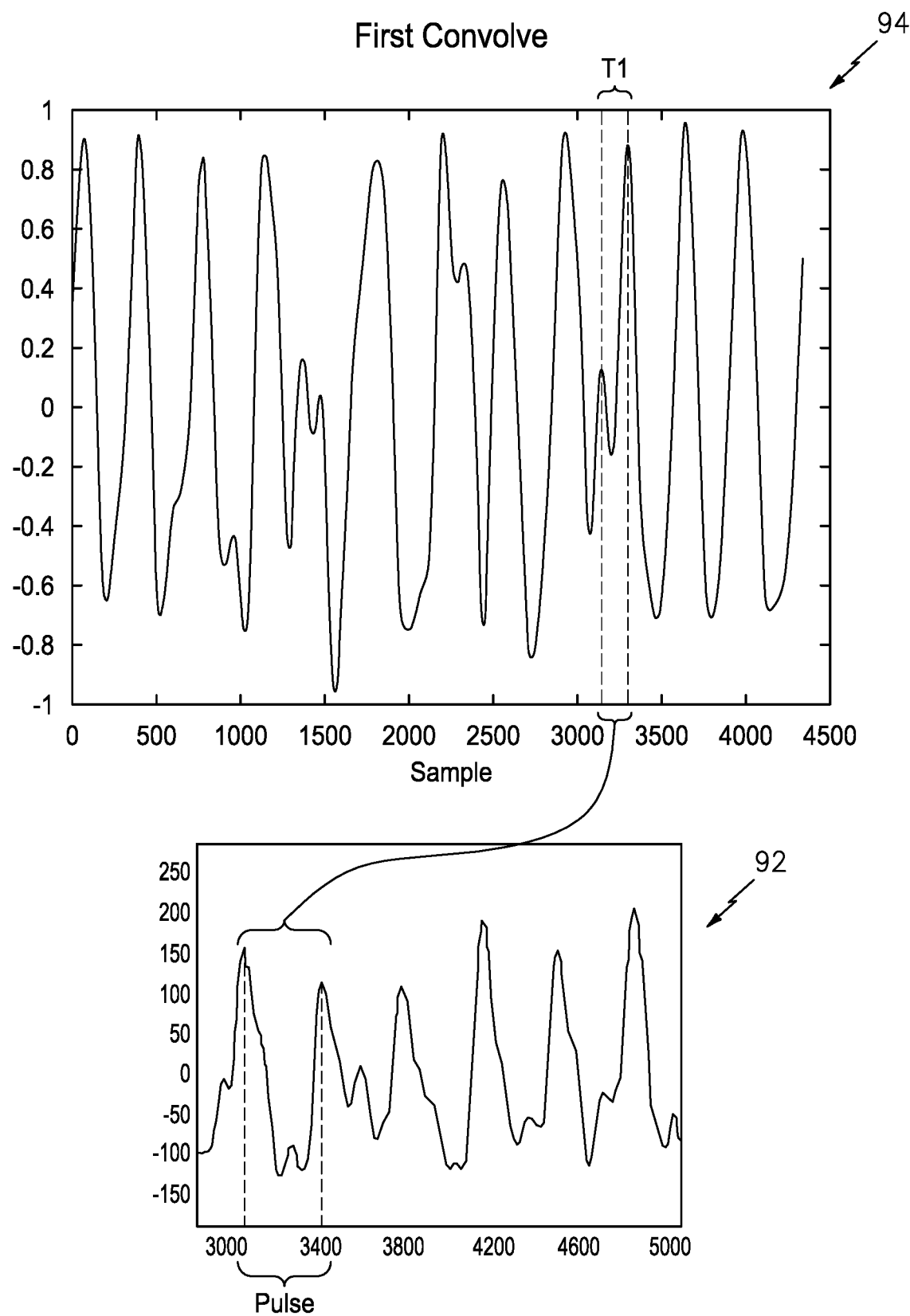
FIG. 15 is a convolution of post band pass filtered data with a standard curve in accordance with embodiments of the present disclosure.

Referring to FIG. 15, an exemplary segment of the first convolution (convolve #1) 94 is shown. The new time-series generated from the above step is essentially a correlation coefficient time-series.

Referring back to FIGS. 11 and 15, from the first convolution 94, local peaks higher than 0.5 are identified by, for example, using MATLAB's "findpeaks" function, and the indices of the peak location are recorded. The convolution is indicative of a correlation between the post band pass filtered data 92 and the "generated" standard curve 93 (in convolve #1). However, it is understood that any correlation between the various pulse waveform curves described herein, including curves from users (e.g. User 1-User N in FIG. 39), curve/waveforms 612 from individual users, representative normal/abnormal pulse data 91, and the sampled pulse waveform data 72 may be used to identify the period or to extract a PWM cycle provided they provide the performance described herein.

The period can be identified as the distance (T1) between the peaks of the first convolution 94. The data (e.g., sample number) between the two consecutive peak indices of the first convolution are used to extract a single pulse from the post band pass filtered time series data 92 (FIG. 13).

Figure 16A:
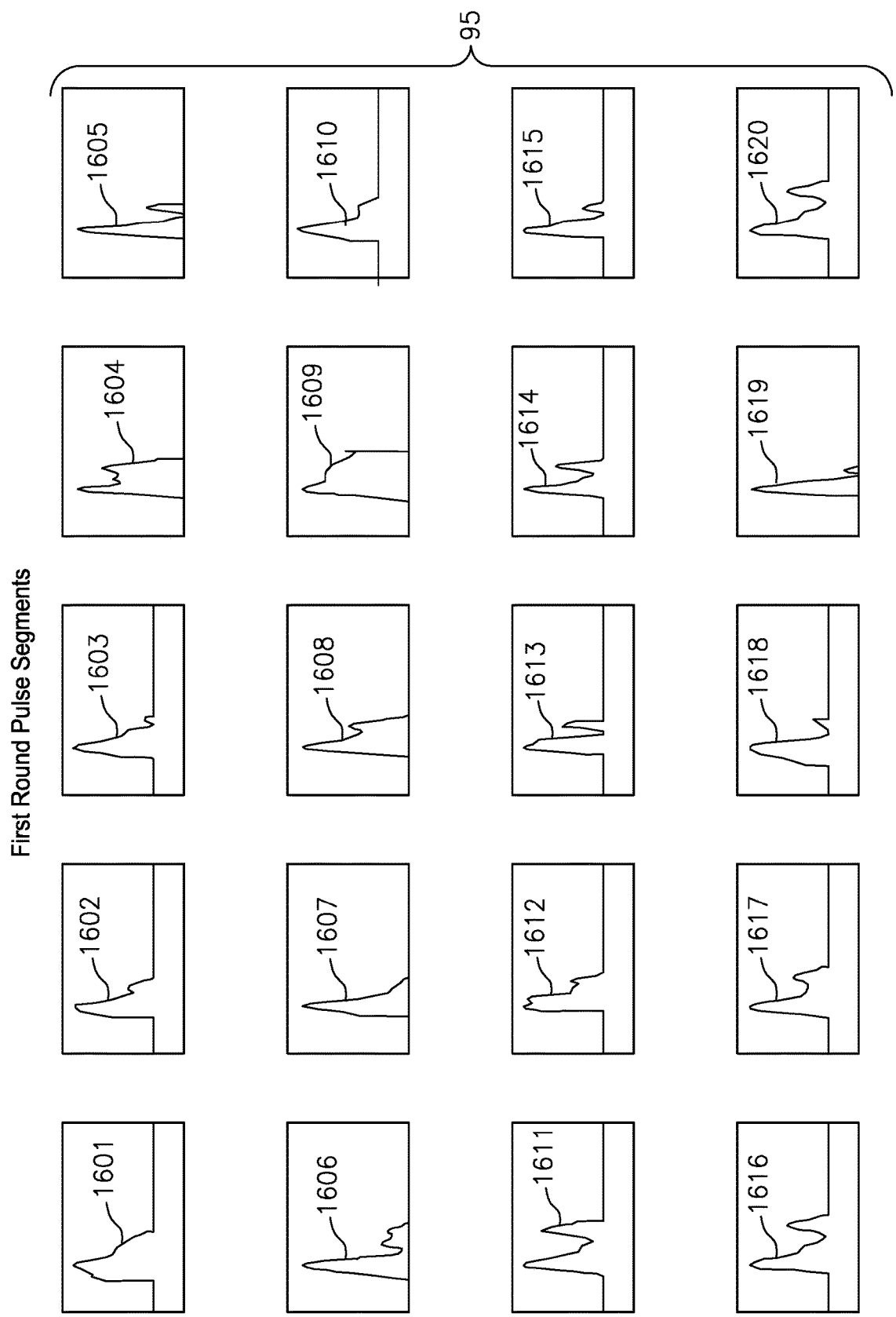
FIG. 16A is extracted individual pulse segments identified from a convolution in accordance with embodiments of the present disclosure.
Figure 16B:
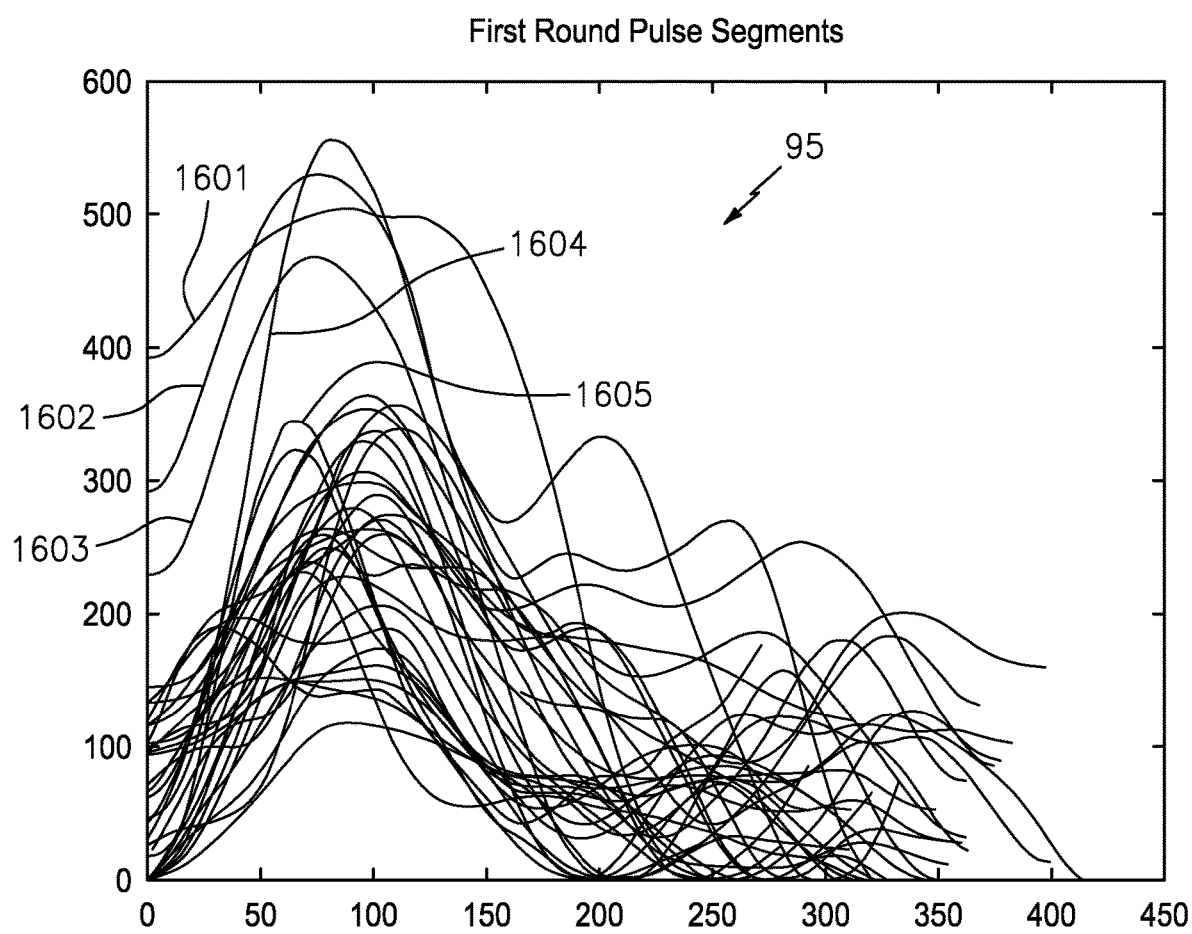
FIG. 16B is the individual pulse segments identified from the convolution overlaid in the same plane, in accordance with embodiments of the present disclosure.

By applying T1 to the post-band pass filtered data 92 the logic can identify or extract first round pulse segments 95 in FIGS. 16A and 16B (block 1104).

Figure 17:
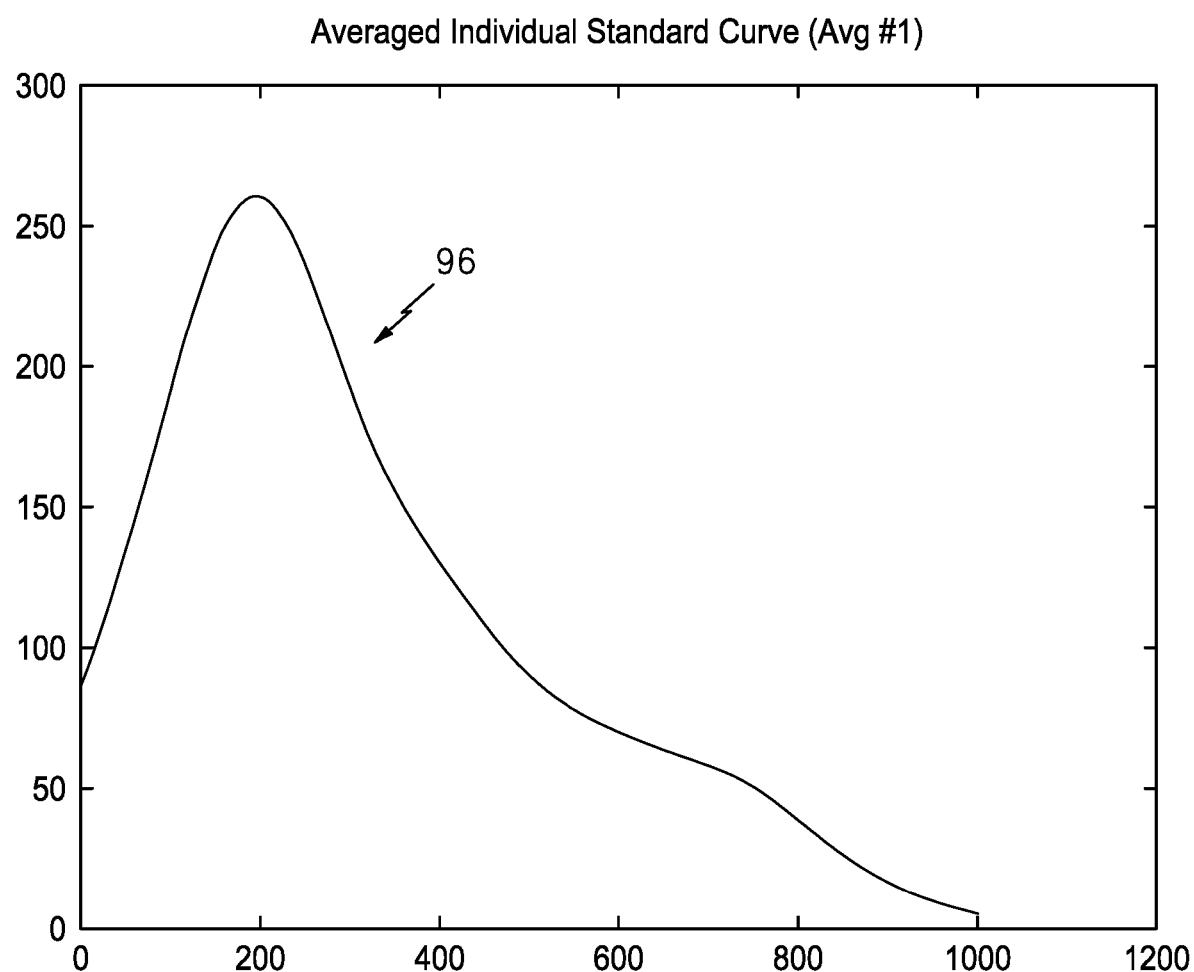
FIG. 17 is an averaged individual standard (IS) curve generated from identified individual pulse segments in accordance with embodiments of the present disclosure.

At block 1105, the identified individual pulse segments 95 are averaged to produce an averaged individual standard (IS) curve 96, as shown in FIG. 17. This IS curve 96 may be used to repeat the segmentation, as discussed further herein.

Figure 18:
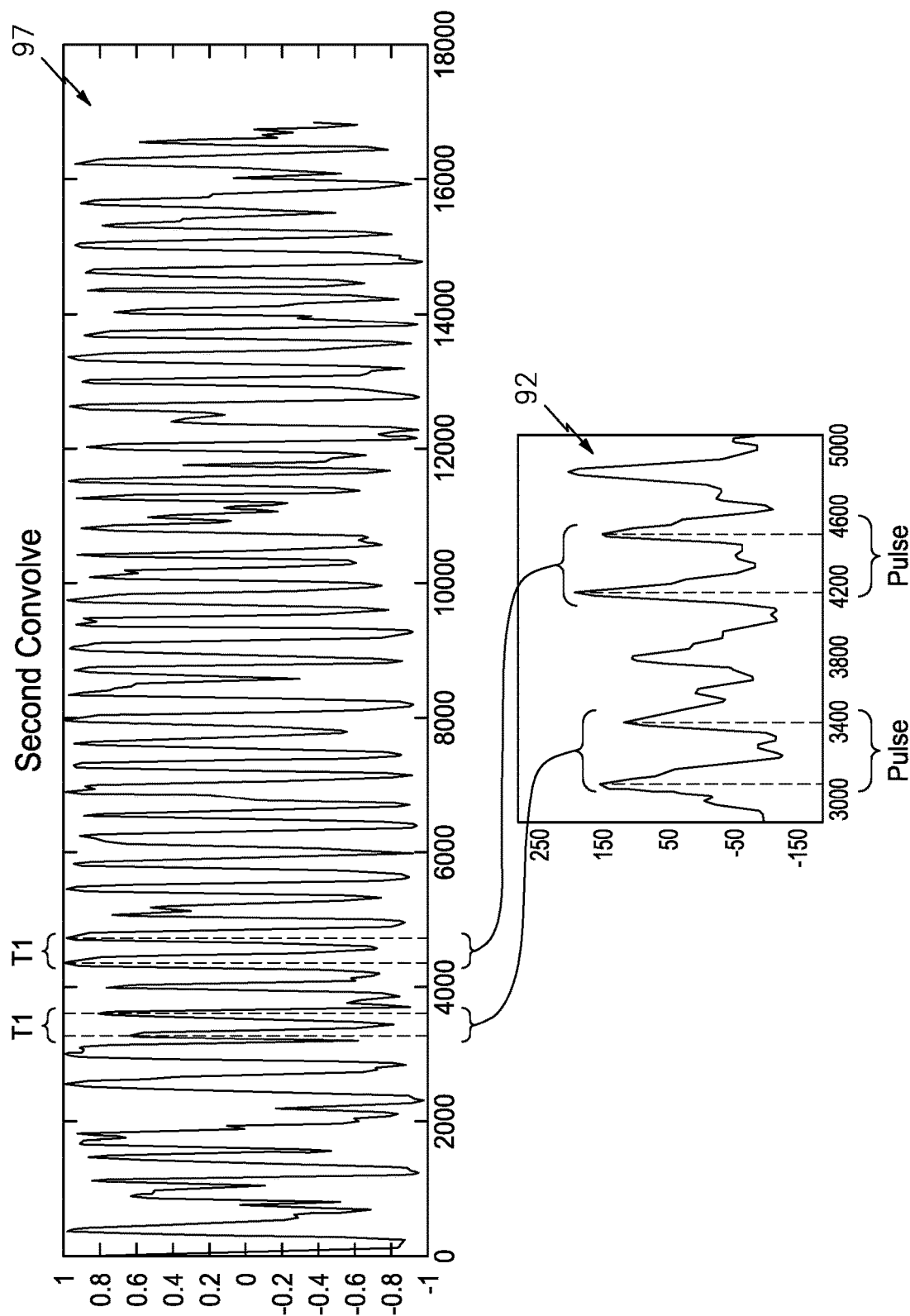
FIG. 18 is a convolution of post band pass filtered data with an averaged IS curve in accordance with embodiments of the present disclosure.

At block 1106, the post band pass filtered data 92 is convolved with the averaged IS curve 96 to produce a second convolution output signal (convolve #2) 97, as shown in FIG. 18.

At block 1107, from the second convolution 97, the period (T1) can again be identified as the distance (T1) between the peaks of the second convolution 97. The data (e.g., sample number) between the two consecutive peak indices of the second convolution are used to extract a single pulse from the post band pass filtered time series data 92 (FIG. 13), similar to that doen in the first convolution.

Figure 19:
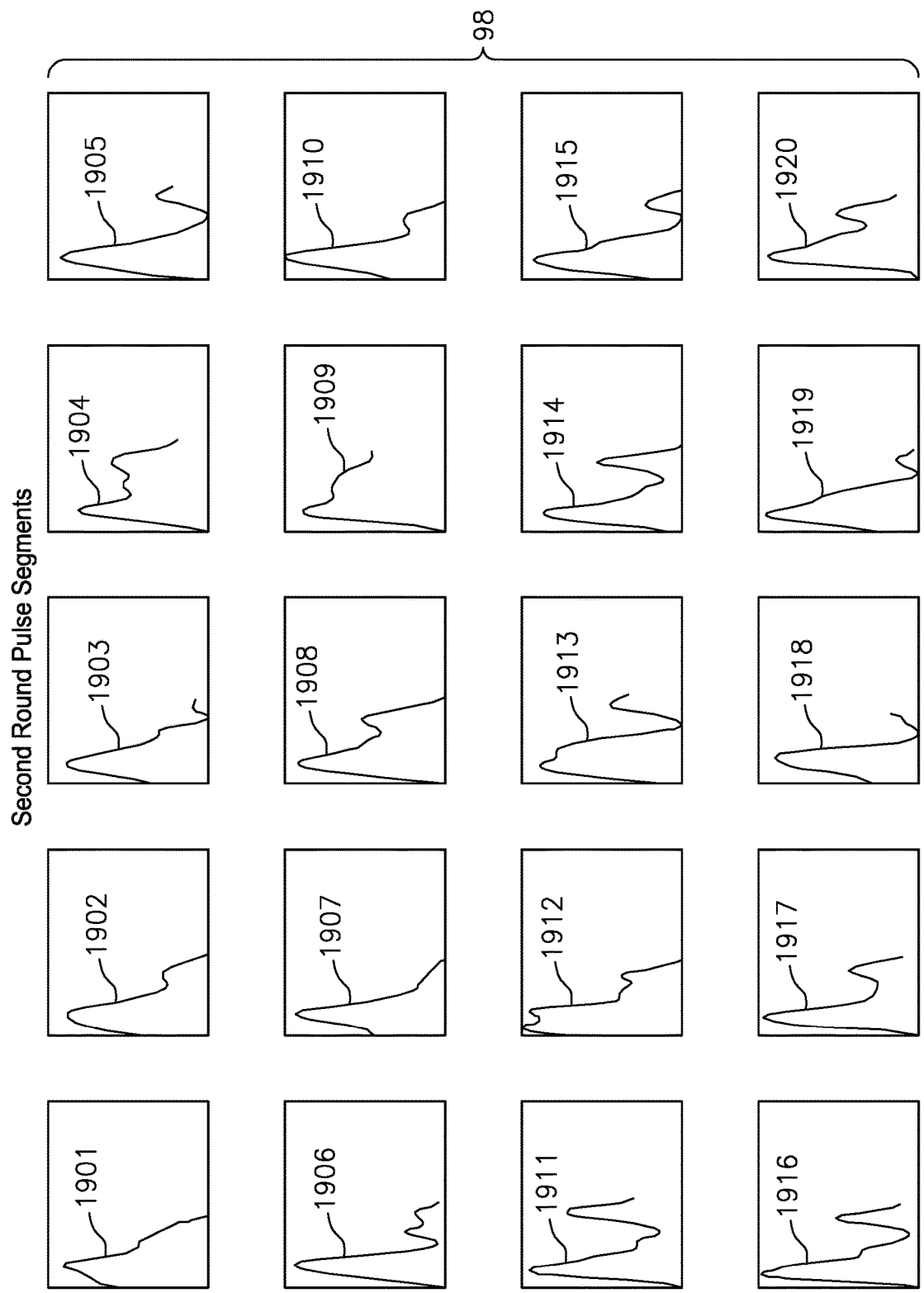
FIG. 19 is extracted individual pulse segments identified from a convolution, in accordance with embodiments of the present disclosure.

At block 1108, the period (T1) is applied to the post-band pass filtered data 92 to identify a second round pulse segments 98, as shown in FIG. 19.

Figure 20:
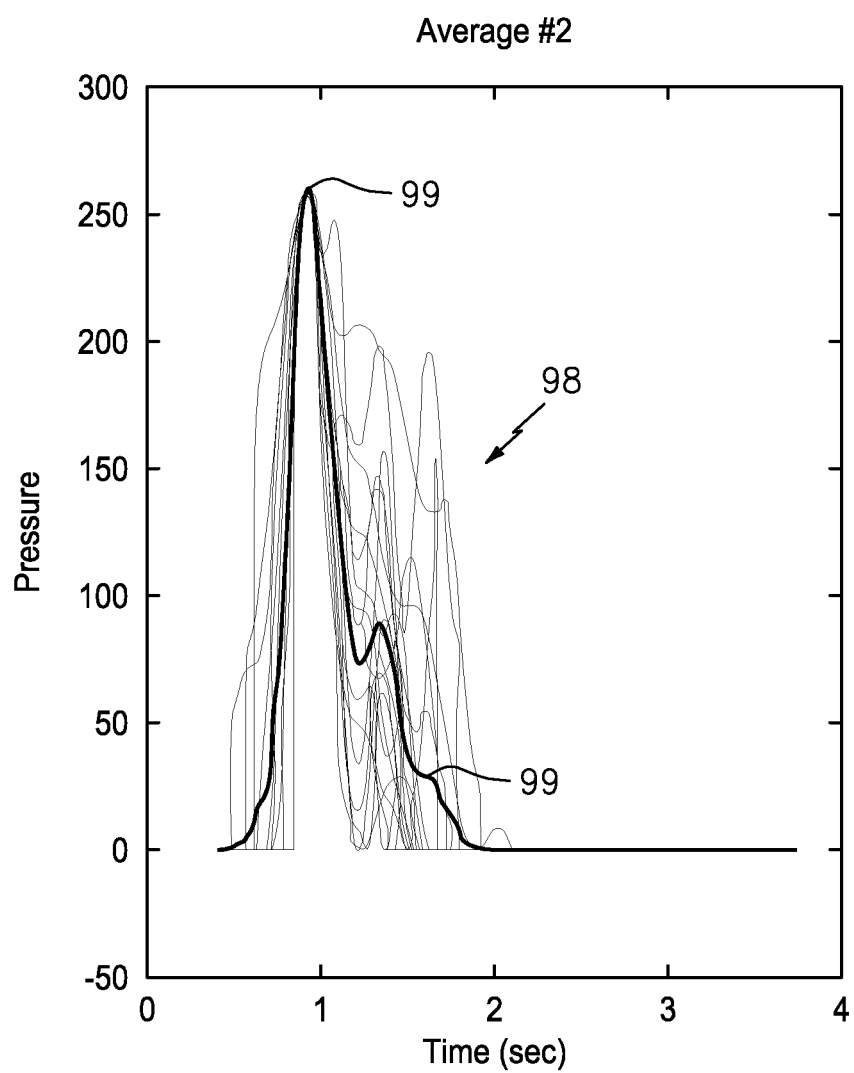
FIG. 20 is an average of individual pulse segments, in accordance with embodiments of the present disclosure.

At block 1109, the identified second round individual pulse segments 98 are averaged to form an averaged pulse wave 99, as shown in FIG. 20.

Figure 21:
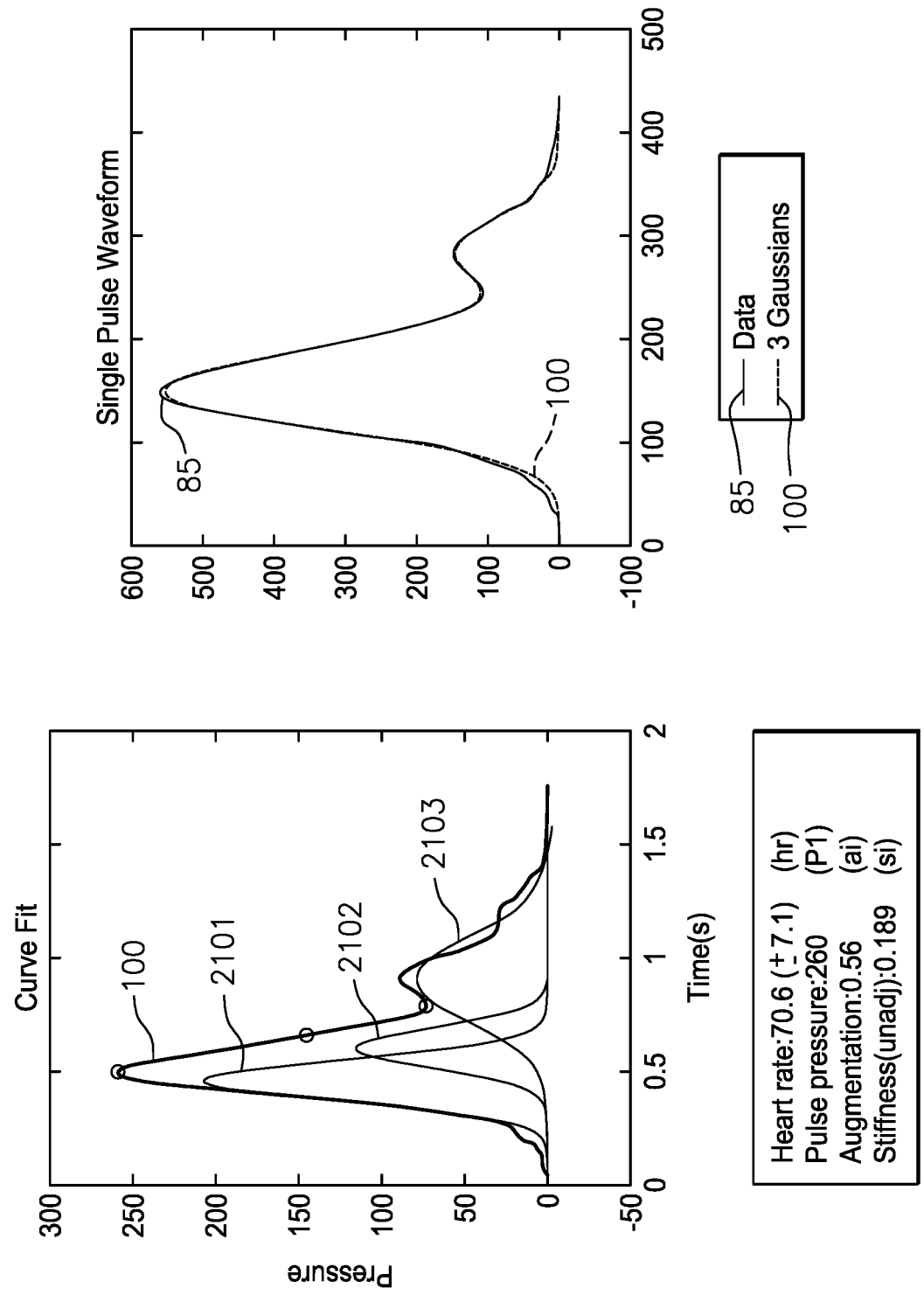
FIG. 21 is an example of a curve fit pulse waveform showing individual Gaussian components, and a curve fit pulse waveform fitted to data according to a method of the present disclosure, in accordance with embodiments of the present disclosure.

At block 1110, the averaged pulse wave 99 is curve fit using a desired function form that models a theoretical pulse waveform for an arterial pulse 100, as shown in FIG. 21. Which may be similar to the curve fit logic 605 (FIG. 6). We have found that a multi-Gaussian form may be used to curve fit the averaged pulse wave 99. More particularly, the multi-Gaussian form of the present disclosure is a sum of three different Gaussian curves 2101, 2102, 2103. Along with a Y-axis offset, the equation for this function is:

$$f(t) = y_0 + \sum_{i=1}^{3} \frac{A_i}{\sqrt{2\sigma^2 \pi}} \exp\left(-\frac{(t-\mu_i)^2}{2\sigma_i^2}\right). \quad \text{(Eq. 7.2)}$$

Theoretically, the data may be fit to only two Gaussian curves, with the rest of the graphed data being noise. In practice, however, we have found that using more than two Gaussian curves in the curve fit function produces better fits with lower sum of squares. Additionally, there may be other relevant health information that can be identified using more than two Gaussian curves, for example, contained within one additional peak when using three Gaussian curves.

A set of curve fit parameters (e.g. $y_o$ for Eq. 7.2) may be calculated using a least-square fitting. Another way to fit parameters is least absolute residual fitting. With least absolute residual fitting, similar to the least squares technique, it attempts to find a function which closely approximates a set of data. In the simple case of a set of (x,y) data, the approximation function is a simple "trend line" in two-dimensional Cartesian coordinates. The method minimizes the sum of absolute errors (SAE) (the sum of the absolute values of the vertical "residuals" between points generated by the function and corresponding points in the data). The least absolute deviations estimate also arises as the maximum likelihood estimate if the errors have a Laplace distribution.

Alternatively, a multi-exponential form may be used to perform the curve fit as described herein with FIG. 6, block 605.

Still referring to FIG. 21, using the curve fit of the averaged pulse waveform 100, heart rate (hr), pulse pressure (P1), augmentation index (ai) and stiffness index (si) can be calculated by the various equations provided herein and described below. In this exemplary example, the user 41 has a heart rate of approximately 70 beats per minute, a pulse pressure of 260, augmentation index of 0.56 and unadjusted stiffness index of 0.189.

At box 606, pulse waveform parameters (p1, p2, n1, and p3) from the theoretical pulse waveform curve (FIG. 22A) may be calculated and updated continuously in real time from the curve fit parameters and/or curve fit 100 described above, as described below with regards to FIG. 22A.

An advantage of the convolution approach is, by calculating the likelihood of each pulse start point individual events can be extracted as signal between two consecutive peaks.

While the above convolve approach has been described utilizing the "generated" standard pulse waveform curve 93 from a virtual database, it is understood that curves from users (e.g. User 1-User N in FIG. 39), curve/waveforms 612 from individual users, representative normal/abnormal pulse data 91, and other curves generated and discussed herein (including convolve #1 94, first round pulse segments 95, averaged IS curve 96, convolve #2 97, second round pulse segments 98, averaged pulse wave 99, and curve fit of average pulse wave 100) may be used instead of or in combination with generated standard pulse waveform curve 93, such as shown by arrow 1112 in FIG. 11.

Referring to FIGS. 22A and 22B, each pulse has a major peak (p1), representing the systolic peak of the blood flow; a minor peak (p2), indicating the reflection of the wave; a dicrotic notch (n1), corresponding to the closing of heart valve; and an inflection point (p3) between the major peak and the notch, representing the augmentation of pulse pressure by the reflected coherent light 12. The Further information about mathematical estimations of parameters can be found in *Circulation*, 95(7), 1827-36, 1997. As noted in the cited reference, radial artery measurements follow a fixed mathematical relationship with aorta pressure change during a heartbeat. Thus, the pulse waveform provides pertinent information regarding a user's vascular system.

Mathematically, the four pulse waveform (PWM) parameters are defined as follows
1. Systolic Peak (p1)
For each complete waveform isolated with n data points (for example, as described in steps 601-605), the systolic peak is defined as the relative height of where the global maximum occurs, i.e.

$$p1 = x_j \text{ where } x_j \geq x_t \forall t \text{ where } j \in (1,n). \quad \text{(Eq. 8)}$$

This is the pulse pressure at time $t_j$ as shown in FIG. 22A.
2. Diastolic Peak (p2)
The diastolic peak is defined as the local maximum that is lower than p1 but higher than all other local maximums. Mathematically, a local maximum in a 2-dimensional x vs. t space occurs when the first derivative is zero and the second derivative is negative. p2 is the relative height of the highest local maximum (if there are m such local maximums), i.e.

$$p2 = \max(x_{k_1}, x_{k_2}, \ldots, x_{k_m}) \text{ where} \quad \text{(Eq. 9)}$$

$$\left.\frac{dx}{dt}\right|_k = 0 \text{ and } \left.\frac{d^2x}{dt^2}\right|_k < 0 \text{ and } p2 < p1 \text{ for } k \in (j, n). \quad \text{(Eq. 10)}$$

This is the pulse pressure at time $t_k$ as shown in FIG. 22A.
3. Notch (n1)
The notch is defined as the relative height of the local minimum between p1 and p2, i.e.

$$n1 = x_l \text{ where } x_l \leq x_t \forall t \in (j,k) \text{ and } l \in (j,k). \quad \text{(Eq. 11)}$$

This is the pulse pressure at time $t_L$ as shown in FIG. 22A.
4. Augmentation Peak (p3)
The augmentation peak is defined as the point of inflection between p1 and n1. Mathematically, this is where both the first and the second derivative are equal to zero, i.e.

$$p3 = x_m \text{ where } \left.\frac{d^2x}{dt^2}\right|_m = 0 \text{ for } m \in (j, l). \quad \text{(Eq. 12)}$$

This is the pulse pressure at time $t_m$ as shown in FIG. 22A.
After curve fitting to the desired equation such as Eq. 6, Eq. 7, Eq. 7.2, a combination thereof, or other function (described above regarding step 605, waveform modeling or box 1110), a heart rate (hr) as well as the parameters defined previously (p1, p2, n1, and p3) will be calculated from the resulting waveforms.

Referring to FIGS. 22A and 22B, the curve parameters are shown as applied to pulse waveform data 74, including intervals described below.

Health parameter calculations, shown in FIG. 23, using the health parameter calculation logic 78 provide the following quantities, which are useful in determining health parameters 80:

1. Inter-spike interval

The inter-spike systolic peak spike time interval ($t_u$ or T1) is defined as $$T1 = \frac{X_{p1_{u+1}} - X_{p1_u}}{f} \quad \text{(Eq. 13)}$$

where f is sampling frequency 56, X is the sample count, and u is a number of each extracted pulse. T1 is typically measured from the start of a pulse segment to the end of a pulse segment. Although, as described herein, T1 may be calculated in a variety of different ways, and avearged.

2. The time interval between systolic peak and notch ($\tau_u$ or T2) is defined as $$T2 = \frac{p1 - n1}{f} \quad \text{(Eq. 14)}$$

3. The time interval between systolic peak and diastolic peak ($\psi$ or $\Delta T$) is defined as $$\Delta T = \frac{p1 - p2}{f} \quad \text{(Eq. 15)}$$

These PWM calculations may be performed for a single pulse waveform or for a plurality of pulse waveforms.

Referring to FIG. 23, based on the above calculated pulse waveform parameters (p1, p2, n1, and p3) and Eqs. 13, 14, and 15, various parameters may be calculated by the health parameter calculation logic 78 having the following steps or blocks or logic.

At step 2301 an average inter-spike time interval T1 between consecutive systolic peaks (p1) is computed in Eq. 13. In particular average T1 may be determined by aligning multiple consecutive extracted pulse segments, and counting the number of p1 systolic spikes over the time for the extracted pulse segments and dividing the number of p1 systolic peaks over the total time of consecutive extracted pulse segments. As another approach, the T1 values for each extracted pulse segment may be averaged (such as a mean average or a weighted average, or other averaging techniques as discussed herein) to determine the average value of T1. The average value of T1 may be used for calculations herein unless otherwise indicated.

In addition, the pulse wave velocity (PWV) may be computed using standard techniques or other techniques as discussed herein (e.g., PWV may be calculated from the stiffness index (SI)).

At step 2303, the heart rate (hr) (beats/min) may be obtained based on the average p1 interval (T1). In particular, the heart rate (hr) may be calculated by the equation hr=(1/T1)(60).

At step 2304, an inter-spike time interval AT between the systolic peak (p1) and the diastolic peak (p2) is computed using Eq. 15.

At step 2305, the heart rate (hr) information from step 2303 and the inter-spike time interval AT of step 2304 is further used to compute the stiffness index (si or $A_{si}$ as described herein). Further information about the stiffness index (si) is explained with regards to Eq. 18 below.

At step 2306, an inter-spike time interval T2 between the consecutive systolic peak (p1) and notch (n1) is computed using Eq. 14.

At step 2308 a stroke volume (SV), i.e. the area under systolic peak (p1), $A_{P1}$ as shown in FIG. 22A, is calculated. This may be done, for example, by determining the area under the curve of the first fitted Gaussian 2101 shown in FIG. 21. $A_{P1}$ is indicative of stroke volume. The term stroke volume (SV) can apply to each of the two ventricles of the heart, although it usually refers to the left ventricle. The stroke volumes for each ventricle are generally equal, both being approximately 70 mL in a healthy 70-kg man. The area $A_{P1}$ may be computed by other techniques if desired.

At step 2309 a mean arterial pressure (MAP) can be calculated. There are various methods for determining mean arterial pressure (MAP) including the equation MAP=(2P2+P1)/3. Other methods of calculating mean arterial pressure are contemplated within the present disclosure. Mean arterial pressure is defined as the average pressure in a patient's arteries during one cardiac cycle. It is considered a better indicator of perfusion to vital organs than systolic blood pressure (SBP). There are several clinical situations in which it is especially important to monitor mean arterial pressure. In patients with sepsis, vasopressors are often titrated based on the MAP. Also, in patients with head injury or stroke, treatment may be dependent on the patient's MAP.

Several physiological indices (i.e. health parameters 80) can be further calculated by the health parameter calculation logic 78, for example:

1. The artery resistance (ar) is defined as $$ar = \frac{x_{p1} - x_{p2}}{\int_{p1}^{p2} x \, dt} \quad \text{(Eq. 16)}$$

Where $x_{p1}$ is the data value at point p1 and $x_{p2}$ is the data value point p2 and the integral in the denominator is the area under the PWM curve from P1 to P2. This calculation may be performed at step 2310 of FIG. 23. The artery resistance (ar) can alternatively be calculated, for example, by utilizing the stroke volume (SV) and mean arterial pressure (MAP), although other means of calculating the artery resistance (ar) are contemplated within the scope of the present disclosure, including those currently practiced in hospitals and other health care facilities.

Artery resistance is the resistance that must be overcome to push blood through the circulatory system and create flow. The resistance offered by the systemic circulation is known as the systemic vascular resistance (SVR) or may sometimes be called by the older term total peripheral resistance (TPR), while the resistance offered by the pulmonary circulation is known as the pulmonary vascular resistance (PVR). Systemic vascular resistance is used in calculations of blood pressure, blood flow, and cardiac function. Vasoconstriction (i.e., decrease in blood vessel diameter) increases SVR, whereas vasodilation (increase in diameter) decreases SVR. The basic tenet of calculating arterial resistance is that flow is equal to driving pressure divided by resistance, as shown by the equation R=$\Delta$P/Q, where R is Resistance, $\Delta$P is the change in pressure across the circulation loop (systemic/pulmonary) from its beginning (immediately after exiting the left ventricle/right ventricle) to its end (entering the right atrium/left atrium), and Q is the flow through the vasculature.

2. The augmentation index (ai) is defined as $$ai = \frac{x_{p3}}{x_{p1}} \quad \text{(Eq. 17)}$$

Where $x_{p3}$ is the data value point p3. At step 2307, an augmentation index (AI) is calculated based on the augmentation peak (p3) and the systolic peak (p1), such as, for example, by dividing the augmentation peak (p3) by the systolic peak (p1), as shown by equation AI=P3/P1. Augmentation index (AI) is a measure of systemic arterial stiffness typically derived from the ascending aortic pressure waveform. Areas of measurement other than the aorta are generally known as the peripheral augmentation index. The augmentation index (AI) may also be referred to herein as the peripheral augmentation index (AI). The augmentation index (AI) is useful in predicting outcomes for various procedures and has shown correlations with aging, hypertension and drug responses. This calculation may be performed at Step 2307 of FIG. 23. Further information regarding the role of the augmentation index in predicting health outcomes, such as hypertension, may be found in *Therapeutic Advances in Cardiovascular Disease* (2008) 2(1) 25-35).

3. The stiffness index (si) is defined as $$si = \frac{h}{\Delta T \times hr^a} + b \quad \text{(Eq. 18)}$$

Where h is the height of the user; $\Delta T$ is the interval between systolic peak and diastolic peak; hr is the heart rate; and a and b are parameters used in the formula and vary by personal attributes. This calculation may be performed at Step 2305 of FIG. 23. Further information regarding the stiffness index may be found in *Mayo Clin Proc.* 2010; 85(5): 460-472.

While the above artery resistance (ar), augmentation index (ai) and stiffness index (si) have been calculated based on the techniques described herein, it is understood that these health parameters 80 and other health parameters 80 may be calculated in a variety of different ways, such as those shown in Zhaopeng Fan, Gong Zhang and Simon Liao (2011). *Pulse Wave Analysis, Advanced Biomedical Engineering*, Dr. Gaetano Gargiulo (Ed.), ISBN: 978-953-307-555-6 which is incorporated herein by reference to the extent necessary to understand the present disclosure.

Calculated parameters for each pulse waveform segment can be averaged or analyzed in various methods as described herein. Also, the parameters calculated herein may be averaged over time.

Figure 39:
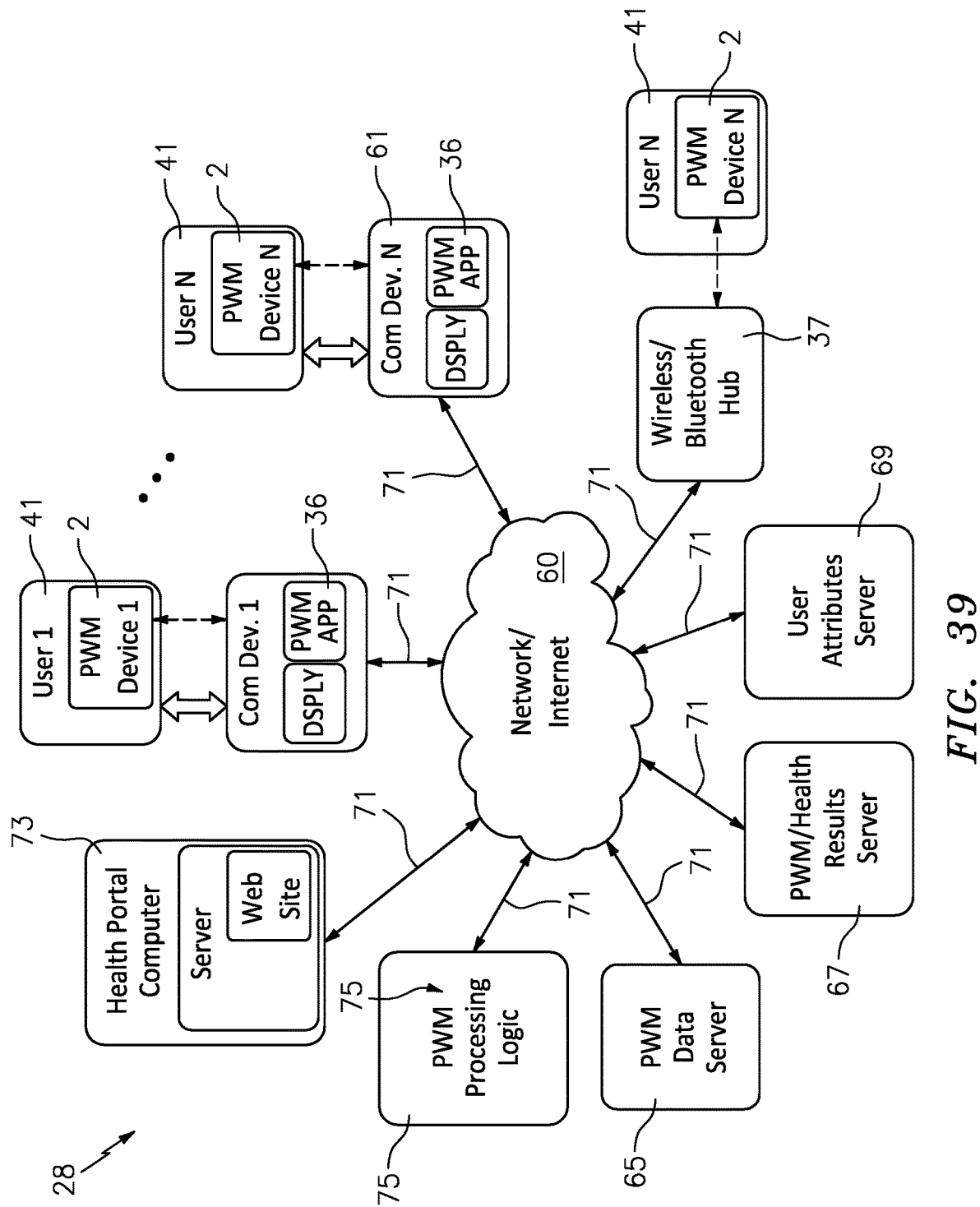
FIG. 39 is a top-level block diagram of components of a pulse waveform management system, in accordance with embodiments of the present disclosure.

Information computed above may be stored in memory of the user device 34 and/or the network environment 60 (FIG. 39). Additionally, the computed information may be displayed on the user device 34.

The health parameter calculation logic 78 is illustrative of the newly applied techniques of the present disclosure and is not meant as an exhaustive list of the PWM device 2 or system 28 capabilities.

Furthermore, while these quantities are defined with the theoretical waveform 74 shown in FIGS. 22A and 22B, there are several factors contributing to the data collection process, which would make the readings deviate from the theoretical situation. A few examples of such external factors are:

1. Change of ambient lighting during collection period;
2. Movement or sweating of the arm during collection period;
3. Individual variation in amount of light reflected;
4. Different user artery location; and
5. Different user blood flow rate.

Figure 24:
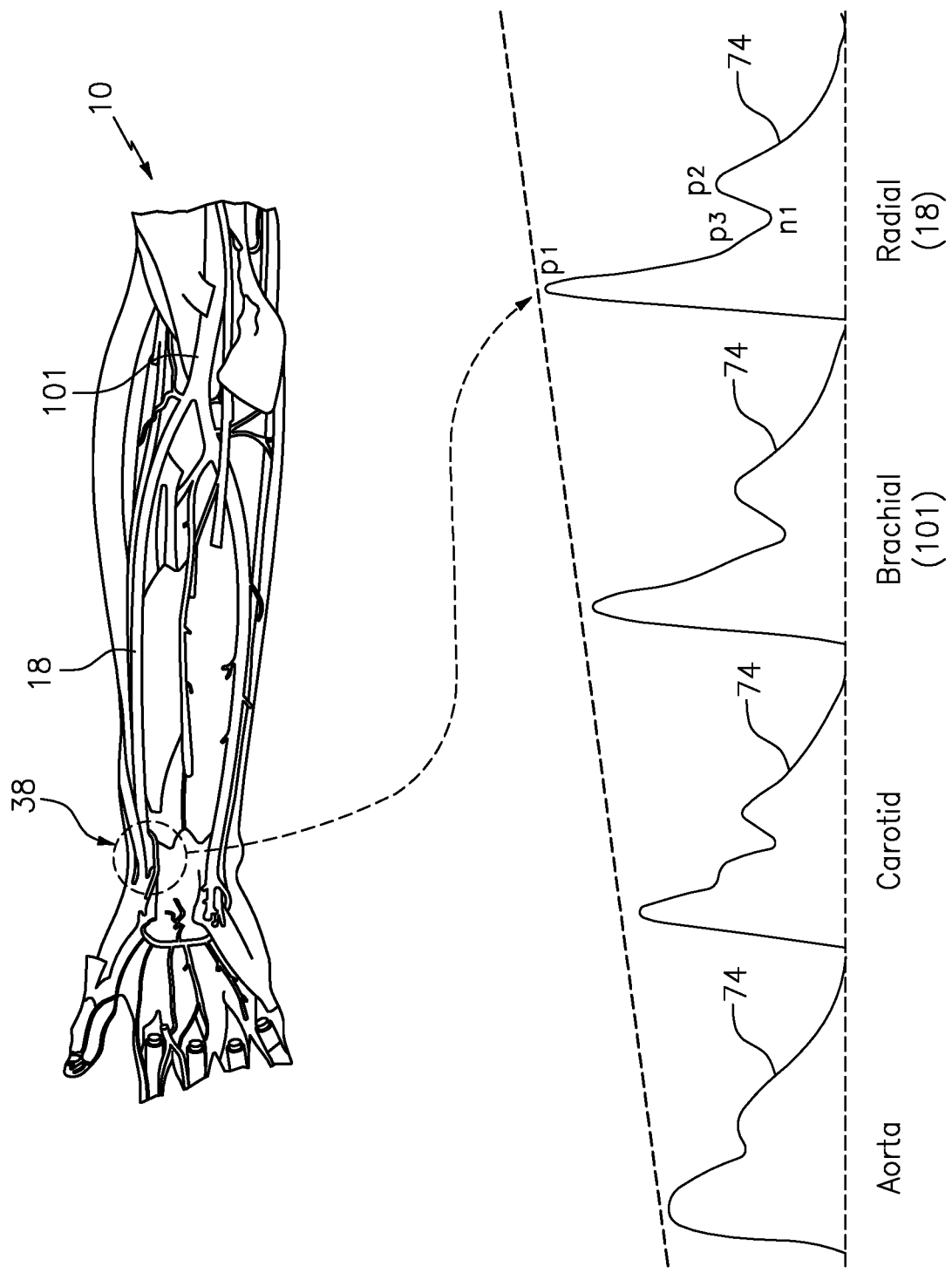
FIG. 24 is a graphical representation of pulse waveforms from different artery locations, in accordance with embodiments of the present disclosure.

Referring to FIG. 24, exemplary graphical representations of the pulse waveform 74 from different artery locations are shown. The reflectance method used in an embodiment of the PWM device 2 does not provide any specificity towards any blood vessel in the body, thus, the source of the signal is significantly determined based on the location of the optical sensor 16 or sensors 16, 16*a*. Other arteries, such as a brachial artery 101, carotid, aorta, or ulnar, will also contain a repeating waveform in every heartbeat. FIG. 24 further illustrates pressure amplification and reflection delay effect based on different artery locations. As shown, (p1) is amplified as the theoretical (or ideal) pulse waveform 74 travels through the artery 18, from the aorta to the radial artery 18.

One area of particular interest is near the thumb on the inner surface of the wrist 38. The pulse waveform 74 found at the inner surface of the wrist 38 produces an amplified pulse waveform 74 without merging the reflection peak (p3) with the dicrotic notch (n1).

The radial artery 18, specifically the area near the thumb on the inner surface of the wrist 38 is particularly advantageous because the fat accumulation in this area is generally low, providing a better signal to noise ratio for PWM measurement. Measuring at the artery 18 allows for detection of the reflection peak (p3). Measurements made from a capillary further delay the reflection peak (p3) resulting in a merge of (p3) with the dicrotic notch (n1) making detection of the reflection peak (p3) extremely difficult, if not impossible. Thus, the device 2 of the present disclosure provides best performance when the pulse waveform is measured at an artery instead of a capillary or capillaries.

The measurement from the brachial artery 101 can be another viable option for detecting the reflection peak (p3). Therefore, if the PWM device 2 is placed at the brachial or radial artery, similar information is produced.

The measurement from an ulnar artery either independently or in combination with the measurement from the radial artery 18 can be another viable option for detecting the pulse waveform. The different locations can provide redundancy or different information, such as arterial stiffness.

Figure 25C:
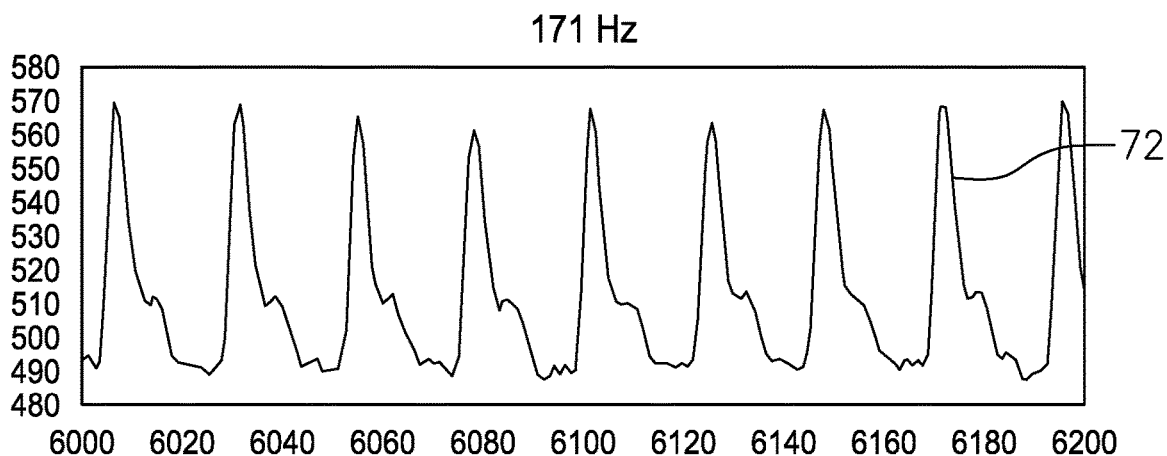
FIG. 25C is a graphical representation of pulse waveform data collected at a specified sampling rate, in accordance with embodiments of the present disclosure.

Referring to FIGS. 25A, 25B and 25C, experimental results show that increasing the sampling rate results in a better defined systolic peak (p1), notch (n1) and diastolic peak (p2). As seen in FIGS. 25A, 25B and 25C, the increased sampling rate from (a) 30 Hz to (b) 68 Hz to (c) 171 Hz results in an increase in accuracy and precision of the repeating sampled pulse waveform 72 at greater than 100 Hz predetermined sampling rate 56. Other sample rates, such as 400 Hz, may be used provided that they provide the desired performance discussed herein. We have also found that when the wavelength ($\lambda$) range of incident light from the LED 14 is in the range of 500-640 nm, or more particularly, 500-540 nm, or more particularly about 515 nm, the pulse waveform data quality is sufficient to provide the desired data/parameters as discussed herein. Other wavelength ranges may be used provided they achieve the desired performance criteria.

Figure 26:
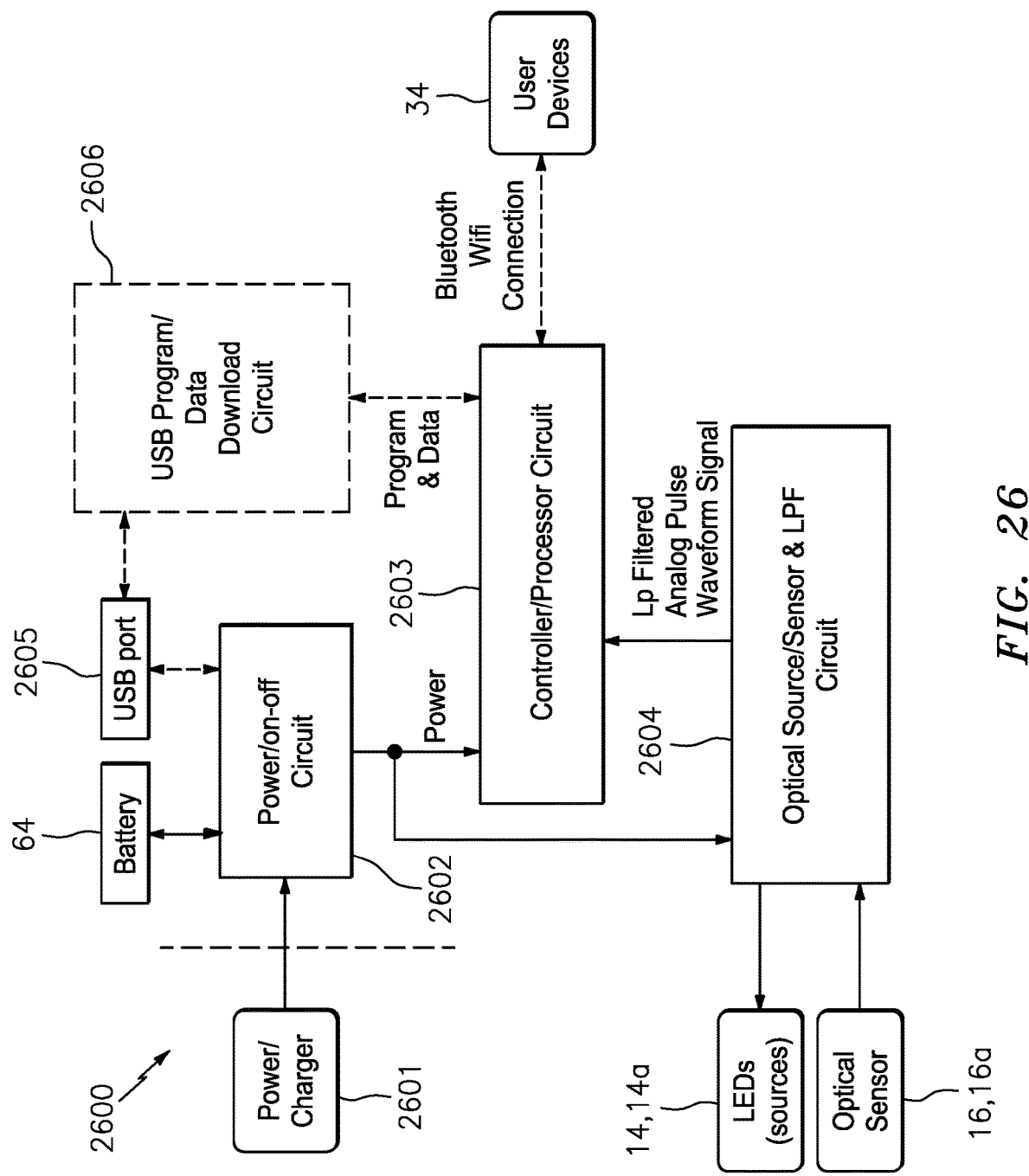
FIG. 26 is a block diagram of circuits implemented in a PWM device in accordance with embodiments of the present disclosure.

Referring to FIG. 26, a circuit block diagram 2600 for the PWM device 2 generally includes a power/on-off circuit 2602, a controller or processor circuit 2603, and an optical source/sensor & low-pass filter (LPF) circuit 2604. In some embodiments, the PWM device 2 may further include a USB port 2605 with a USB program or data download circuit 2606 run by, for example, a USB control unit (U2).

The power/on-off circuit 2602 may utilize components such as those shown in FIGS. 27, 28, 29, 30, 31, 32, 33, 34A and 34B including battery 64 (U1). Power supplied by the battery 64 or power/charger 2601 is provided to the power/on-off circuit 2602 in order to power the controller/processor circuit 2603 and the optical source/sensor & LPF circuit 2604. In embodiments that utilize a USB port, the power/on-off circuit 2602 may also supply power to the USB program or data download circuit 2606. The circuit 2602 may also have a voltage regulator for controlling the supply voltage to other circuits, a battery charging circuit, and an on/off switch.

The optical source/sensor and LPF circuit 2604 is configured to supply power to LEDs 14, 14a and receive analog pulse waveform signal from optical sensor 16. The circuit 2604 also has the analog low pass filter 50 discussed herein, and provides a low pass filtered analog pulse waveform signal to the controller/processor circuit 2603.

The controller/processor circuit 2603, which may include a microcontroller chip (including A/D converter) MCU 52 (U4) as discussed herein receives the low-pass filtered analog pulse waveform signal received from the optical sensor 16 and the optical source/sensor & LPF circuit 2604 and converts it to a digital sampled PWM signal and transmits it to the user devices 34 via Bluetooth and/or Wifi connection. Such data transfer may work in conjunction with a program supplied by the USB program or data download circuit 2606.

Figure 32:
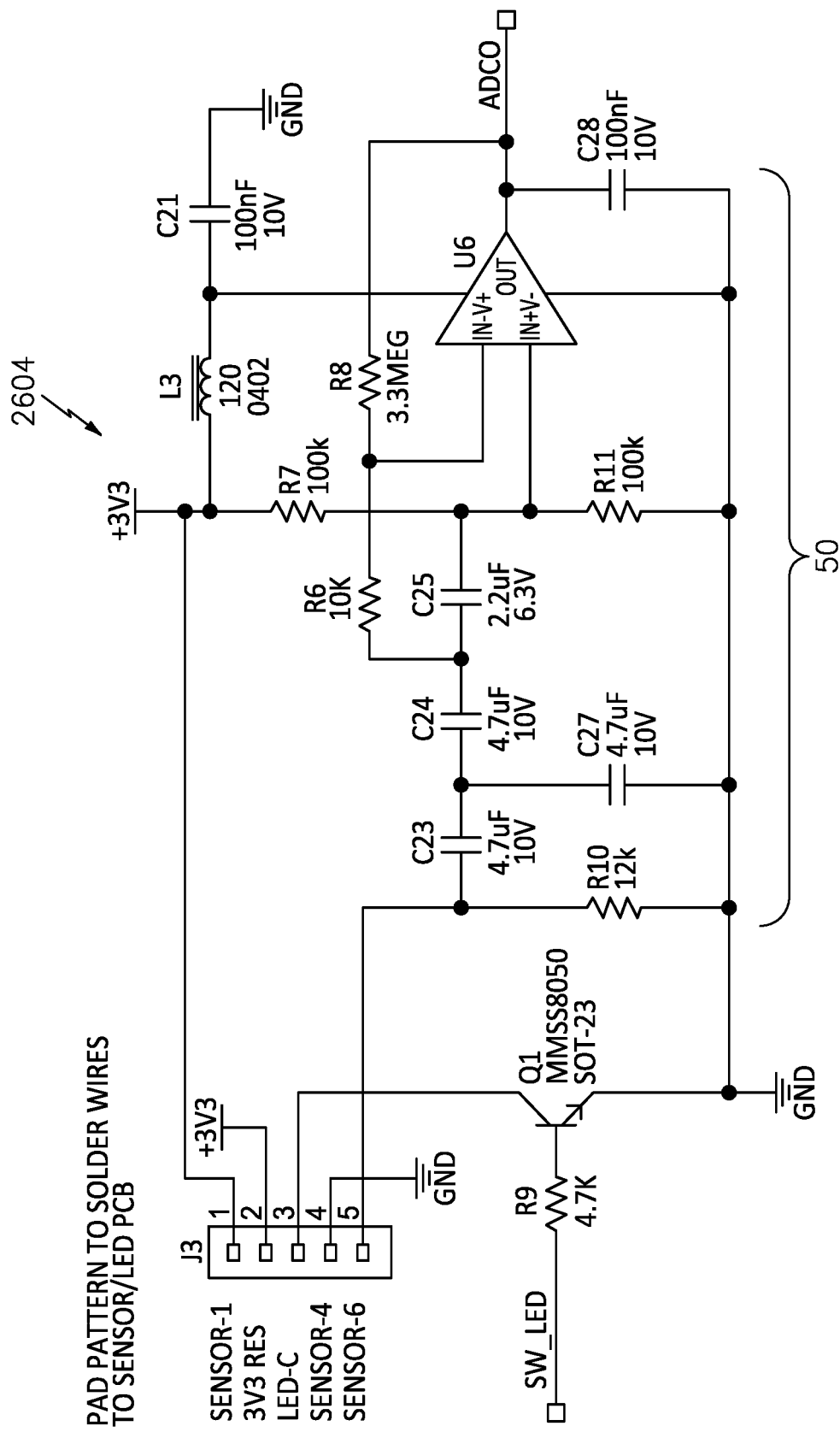
FIG. 32 is a circuit diagram of electronic hardware components implemented in a second embodiment of a PWM device, in accordance with embodiments of the present disclosure.
Figure 33:
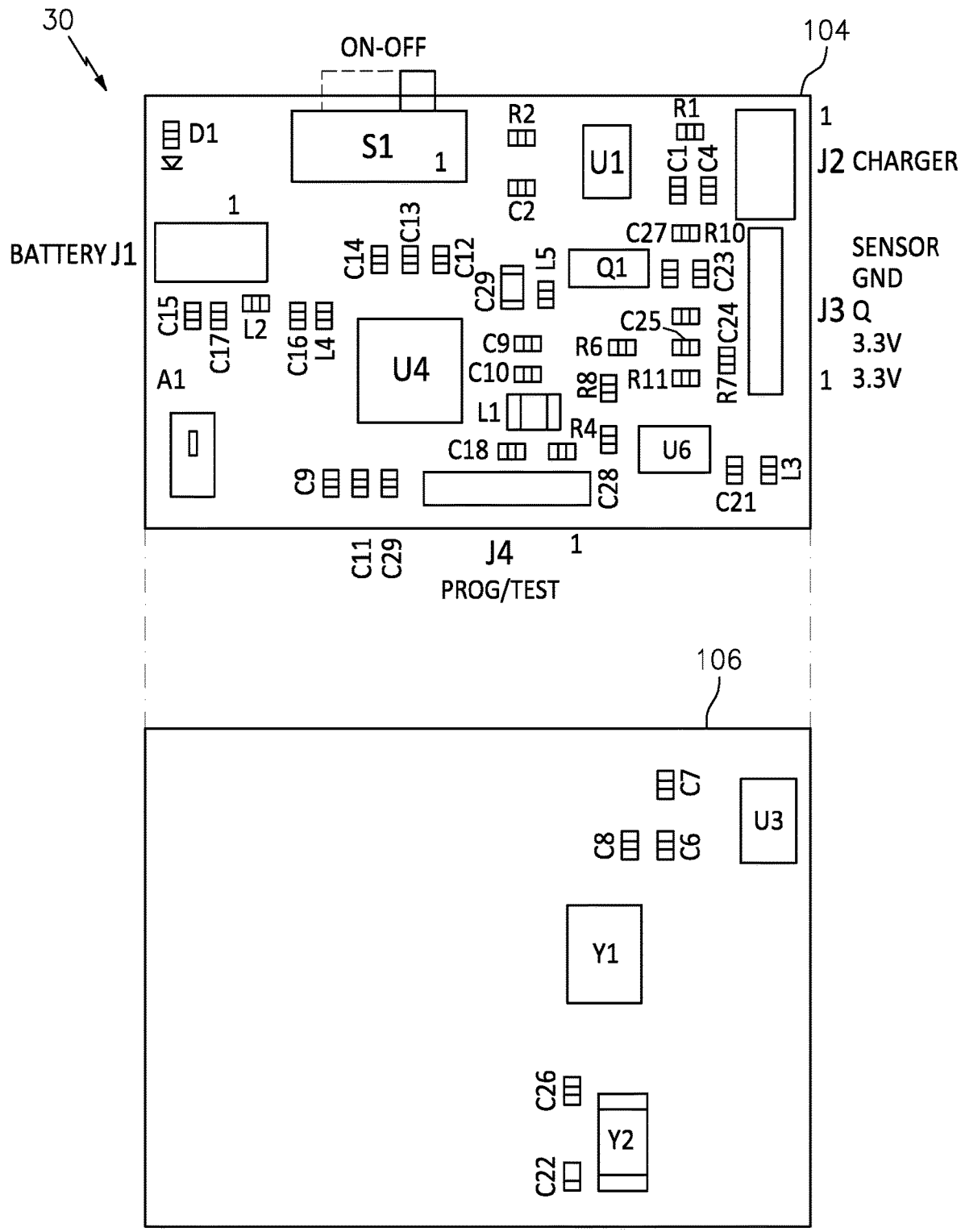
FIG. 33 is top and bottom views respectively, of circuit board layout of electronic hardware components of the circuit of FIG. 34A, in accordance with embodiments of the present disclosure.
Figure 34:
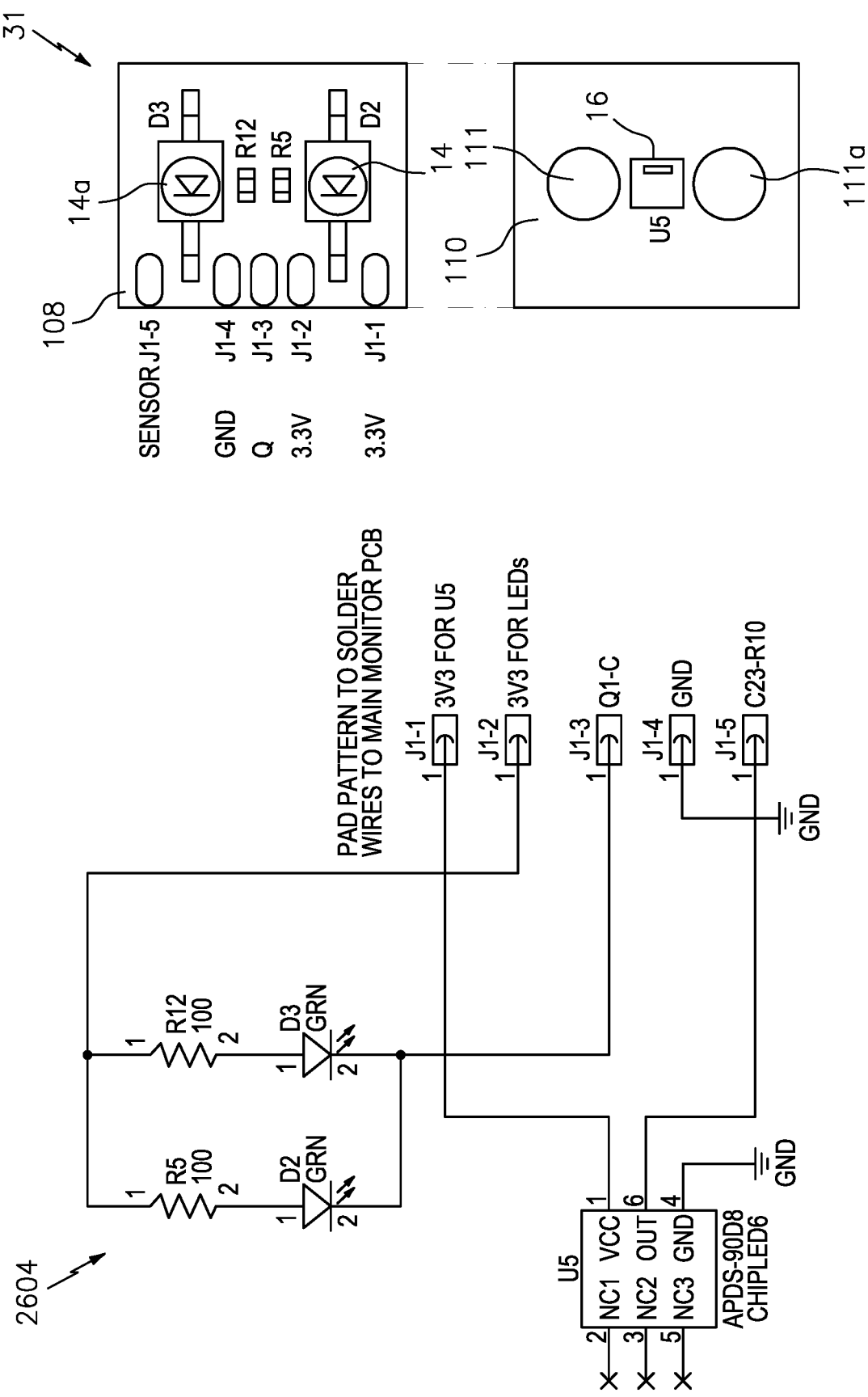
FIG. 34A is a circuit diagram of electronic hardware components implemented in a second embodiment of a PWM device in accordance with embodiments of the present disclosure.
FIG. 34B is a top and bottom view of a circuit board layout of electronic hardware components of the circuit of FIG. 34A, in accordance with embodiments of the present disclosure.

In various embodiments discussed herein, the optical source/sensor & LPF circuit 2604 shown in FIGS. 32 and 34A may be split among two circuit boards 30 (FIGS. 28, 29, 33) and 31 (FIG. 34).

Figure 27:
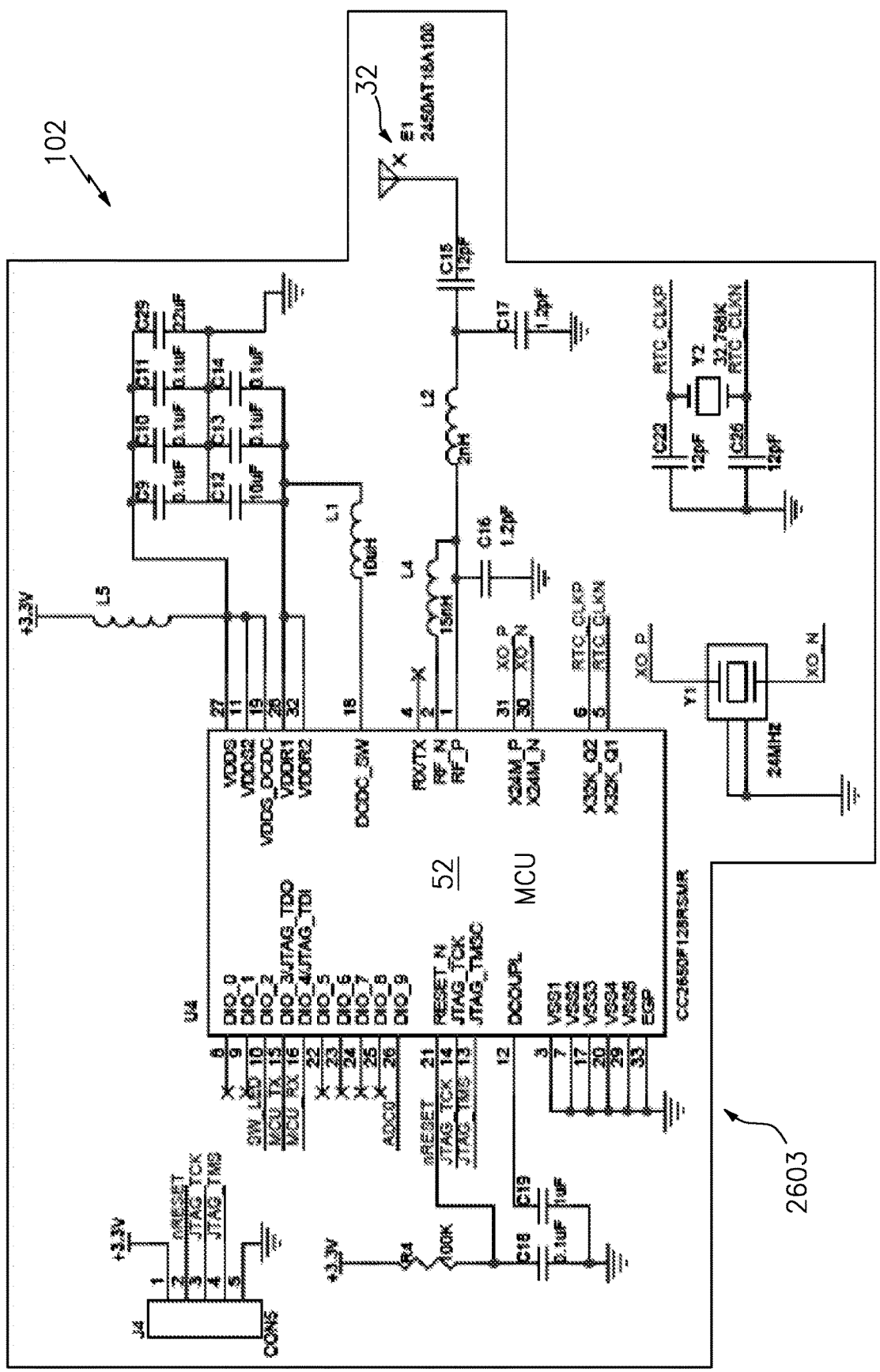
FIG. 27 is a circuit diagram of electronic hardware components implemented in a PWM device, in accordance with embodiments of the present disclosure.
Figure 27:
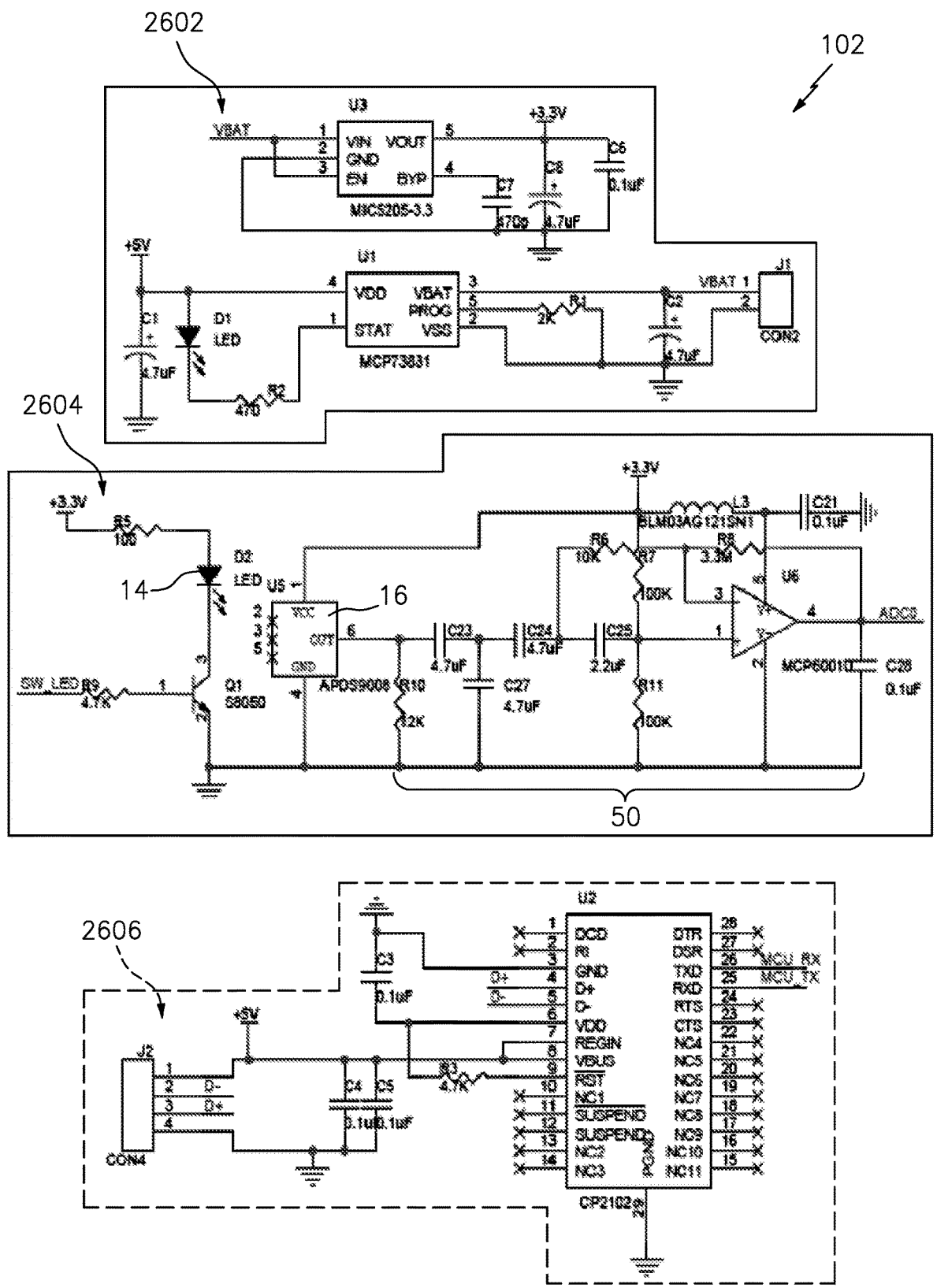

Referring to FIG. 27, a schematic circuit 102 shows one embodiment implemented in the PWM device 2. The component numbers R's (resistors), U's (chips), C's (capacitors), L's (inductors), D's (diodes), Q's (transistors of FIGS. 2-3 and 27, 28, 29, 30, 31, 32, 33, 34A and 34B all correspond to components on the schematic diagram of the circuit 102 of the device. The circuit 102 includes embodiments of the circuits 2602, 2603, 2604, 2606, discussed herein above with FIG. 26.

More specifically, the circuit 102 of FIG. 27 includes a battery charging unit U1 for charging the lithium-ion battery 64 and also providing reverse discharge protection. Specifically, U1 can be a 500 mA linear charge management controller including an integrated pass transistor such as part number MCP73831 made by Microchip Technologies Inc. The battery charging unit U1 includes at least one 10V 4.7 uF capacitor C1 and/or C2. The capacitors C1, C2 may be comprised of any conductive material, for example, tantalum and can further be part number T491A475K010AT made by Kennet Electronics Corporation. The battery charging unit U1 may further include a low power consumption LED D1, in an electrically connected circuit, for example, a hyper-red SMD CHIP LED lamp such as part number APHHS1005SURCK made by Kingbright Company LLC. Resistors R1 and R2 help prevent a large current in the battery charging unit U1. A battery connector J1 can connect the battery charging unit to the rechargeable lithium-ion battery 64.

The circuit 102 further includes a USB control unit U2 for including a USB connection. Specifically, U2 can be a single-chip USB to UART bridge such as part number CP2102 made by Silicon labs, and allows for USB to UART data transfer. USB control unit U2 may further include an integrated USB transceiver, integrated clock, internal 1024-byte programmable ROM for vendor ID, product ID, serial number, power descriptor, release number, and product description strings. The USB control unit U2 is connected to a USB programming connector J2. J2 connects an external device to electronically download programs or firmware to the MCU 52 (U4). J2 may be, for example, a micro USB power charging, digital to digital hardware for sampled data transfer with the USB control unit (U2) from the PWM device 2.

The circuit 102 further includes a voltage regulator U3 for regulating voltage throughout the circuit 102. Specifically, the voltage regulator U3 may be a linear voltage regulator with low-noise output, low dropout voltage (typically 17 mV at light loads and 165 mV at 150 mA), and very low ground current (600 A at 100 mA output) such as part number MIC205-3.3 made by Microchip.

The circuit 102 further includes the MCU 52 (U4) for performing the data processing steps outlined in FIGS. 5, 6, 7, 8A, 8B, 8C, 9, 10, 11, 12, 13, 14, 15, 16A, 16B, 17, 18, 19, 20, and 21. In some embodiments, the MCU 52, U4 may be a 2.4 GHz ultra-low power wireless microcontroller. More specifically, the MCU 52 may be a CC2650 SimpleLink™ Multistandard Wireless MCU part number CC2650F128RSMR made by Texas Instruments Inc. To support the MCU 52 (U4) capacitors C9, C10, C11, C12, C13 and C14 are stacked. Capacitors C15 and C16 can be electrically connected between the MCU 52, U4 and the RF antenna 32 (E1, A1). Additionally, capacitors C18 and C19 are connected to the MCU 52 (U4). A plurality of inductors L1, L2, L4, and L5 are also connected as shown in FIG. 17.

The antenna 32 (E1, A1) may be a 2.4 GHz Chip RF antenna part number 2450AT18A100 made by Johanson Technology Inc.

A crystal Y1 used for setting the frequency of about 24 MHz may be a quartz crystal such as part number CX3225SB26000D0FFFCC made by AVX Corp. Another crystal Y2, used for setting the frequency of about 32.768 kHz±20 ppm Crystal, such as part number ST3215SB32768H5HPWAA made by AVX Corp. Both crystals Y1 and Y2 set reference clocks used for the MCU 52.

The circuit 102 further includes a photo-detector/optical sensor 16 (U5) for pulse detection. An example of such a photo-detector/optical sensor is part number APDS9008 made by Avago Technologies. The photo-detector/optical sensor U5 has particular application in significantly reducing power consumption.

The circuit 102 further includes the LPF and analog linear amplifier 50 (U6) having components (e.g., resistors, capacitors and inductors). As described earlier, the LPF and analog linear amplifier 50 (U6) may be a general purpose op amp offering rail-to-rail input and output over approximately a 1.8 to 6V operating range. More specifically, the amplifier U6 may be, for example, a 1 MHz, Low-Power Op Amp part number MCP6001 made by Microchip Technology Inc.

The circuit 102 further includes the LED 14 (D2) for providing the incident light 4. As described earlier, LED 14 (D2) may be a green source color made with InGaN on a sapphire Light Emitting Diode. More specifically, the LED 14 may be a subminiature solid-state lamp part number AM2520ZGC09 made by Kingbright Company LLC.

Figure 28:
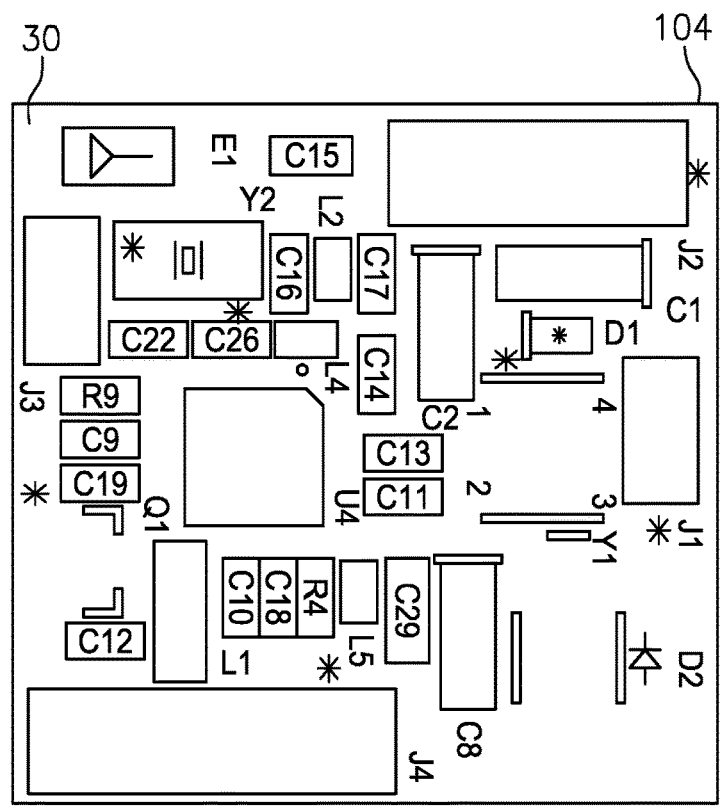
FIG. 28 is a top view of a circuit board layout of electronic hardware components of the circuit of FIG. 27, in accordance with embodiments of the present disclosure.
Figure 29:
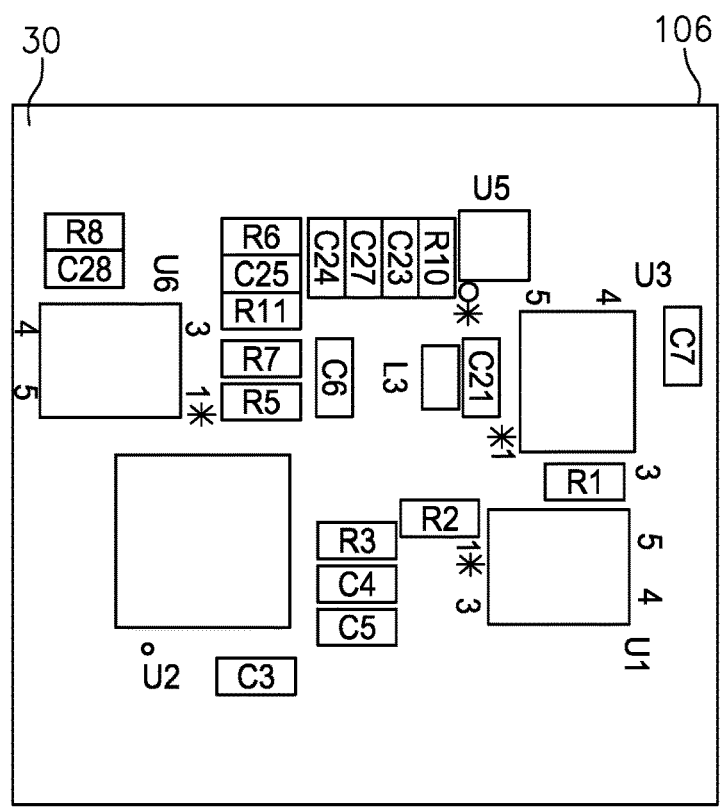
FIG. 29 is a bottom view of a circuit board layout of electronic hardware components of the circuit of FIG. 27, in accordance with embodiments of the present disclosure.

Referring to FIGS. 28 and 29, the printed circuit board 30 comprises a top layer 104 and a bottom layer 106 secured together to complete the circuit board 30 having the components of the circuit 102 (FIG. 27) laid out as indicated.

Referring to FIGS. 30, 31, 32 and 34A a second embodiment of the PWM device 2 corresponding to the circuits 2602, 2603, 2604 (split between FIGS. 32 and 34A). Such embodiments may, optionally, not include a USB connection.

Figure 30:
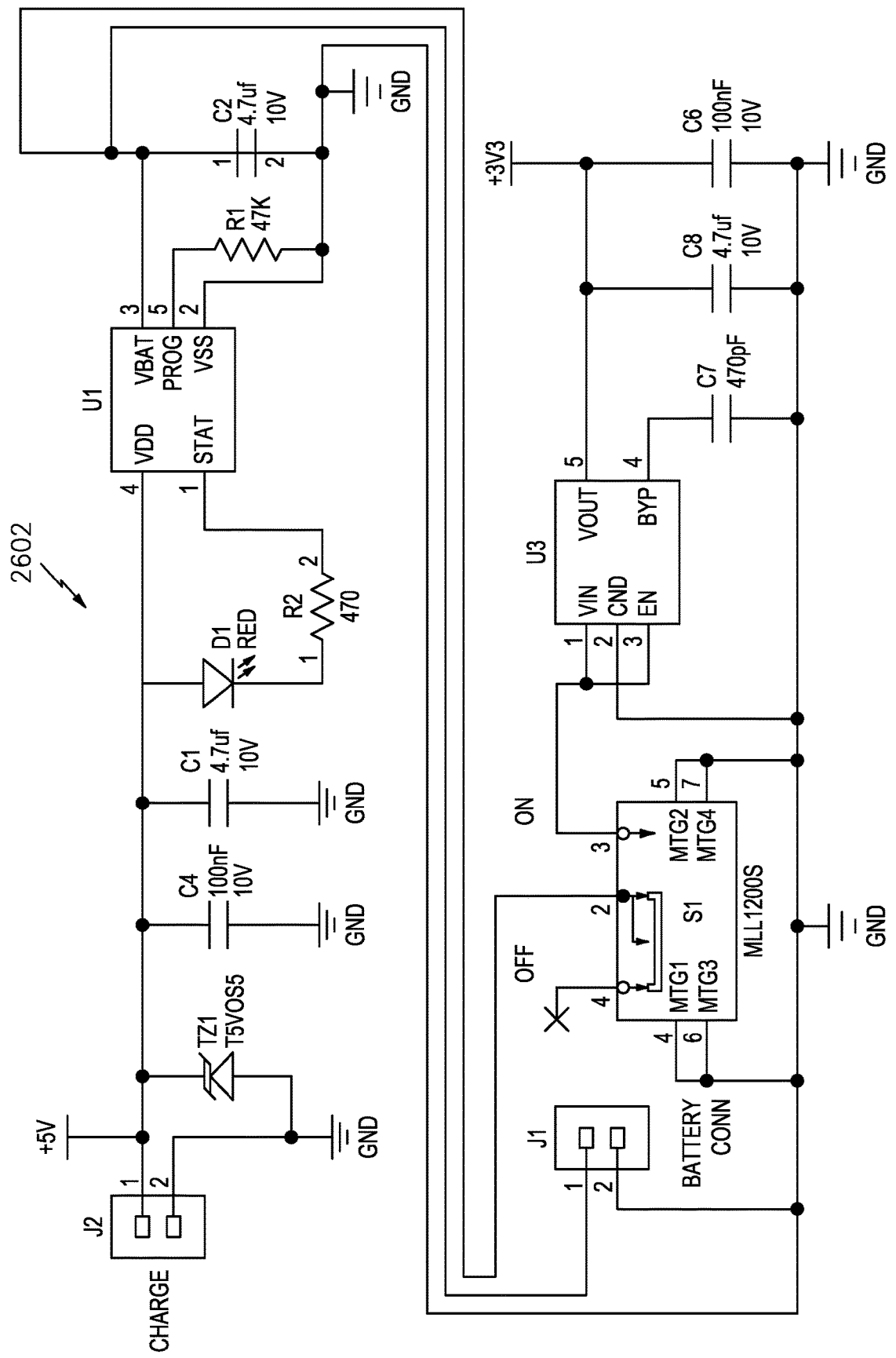
FIG. 30 is a circuit diagram of electronic hardware components implemented in a second embodiment of a PWM device, in accordance with embodiments of the present disclosure.
Figure 31:
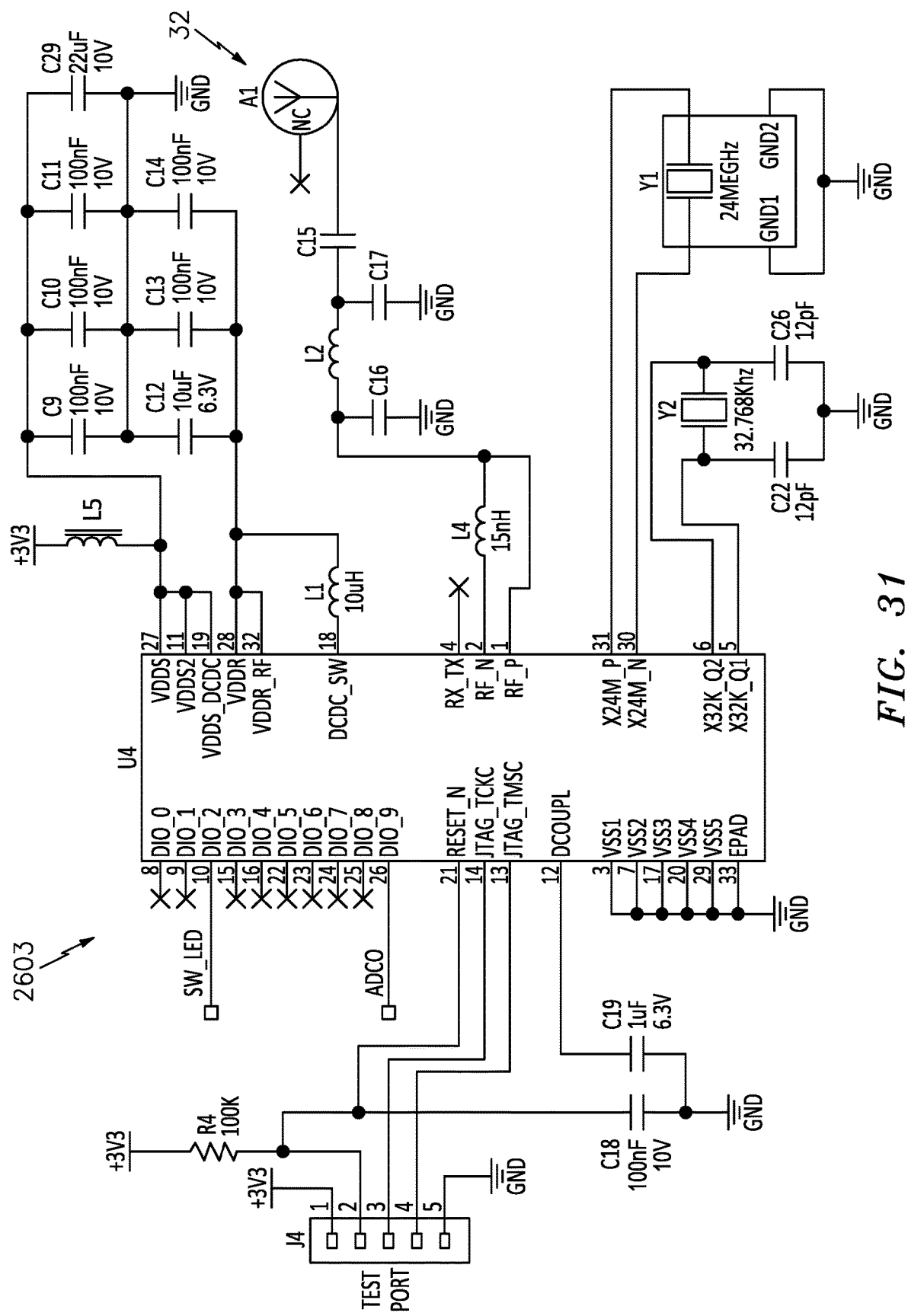
FIG. 31 is a circuit diagram of electronic hardware components implemented in a second embodiment of a PWM device, in accordance with embodiments of the present disclosure.

Referring to FIGS. 33 and 34B, in the second embodiment, the circuits 2602, 2603, 2604 are located on circuit board 30 (FIG. 33) except for sensor 16 or sensors 16, 16a (FIG. 47B) may be located on a separate board 31 from the printed circuit board 30 of FIGS. 30, 31 and 32. In such embodiments, a circuit including two LEDs D2, D3 provide substantially balanced reflected (or uniform) light on either side of (or across the surface of) the optical sensor 16 (U5). We have found that PWM signal quality is improved with two LEDs. Additionally, as discussed herein, printed circuit board 30 has a top layer 104 and a bottom layer 106 secured together to complete the circuit board 30. Similarly, printed circuit board 31 has a top layer 108 and a bottom layer 110 secured together to complete circuit board 31.

In some embodiments, circuit board 31 may have openings 111, 111a disposed on the bottom layer 110 to allow incident light 4 from LEDs 14, 14a to pass through the bottom layer 110. The values or part numbers for the various components on the circuits 2602, 2603, 2604 of FIGS. 30, 31, 32, and 34A, are shown on the corresponding circuit diagrams or, if not, they are the same as in FIG. 27. Also, the function and operation of the circuits 2602, 2603, 2604 are substantially the same for both the first and second embodiments; however, the layouts may be different and certain components or component values may be different, but the effect of such differences would generally be understood by one skilled in the art and in view of the discussion of the description of FIG. 27 (first embodiment).

Other circuit components, component values, and schematic configurations may be used if desired, provided they meet the functions and performance requirements described herein.

Referring to FIGS. 35, 36A, 36B, 36C, 37, 38A, 38B, 38C and 40, 41 42A, and 42B, the casing 42 of the PWM device 2 houses the printed circuit boards 30 and/or 31 and the above-described electronic circuits and circuit components.

Referring to FIG. 35, a connector cable 112, such as a double male end USB connector cable, may connect the PWM device 2 to the user device 34 to exchange data. The connector cable 112 connects through the casing 42 via a data/power connection port 113 connected to the USB program or data download circuit 2606 by USB connector J2. Also, as discussed herein, the data transfer of the sampled pulse waveform data 72 off device and to the digital data processing logic 75 may be performed wirelessly e.g., via Bluetooth® or other wireless technology as discussed herein. The PWM device 2 may further include an on/off switch 114 capable of turning on the PWM device 2.

Referring to FIGS. 36A, 36B and 36C, in some embodiments, the casing 42 may comprise two sections, a top section 116 and a user facing bottom section 118. The bottom section 118 is adapted to allow the optical sensor 16 to transmit the incident light 4 through the opening 48. The dimensions of the casing 42 are approximately 0.64 inches in height by 1.75 inches in length with a depth of 1.00 inch. Other dimensions may be used if desired, provided they meet the functions and performance requirements described herein. Further, the bottom section 118 may contain a curved surface with a curve radius of approximately 1.62 inches. In some embodiments, the top section 116 may have a matching curved surface as the bottom section 118. In some embodiments, the curve of the top section 116 and/or the curve of the bottom section 118 is between approximately 0.5 to 5 inches.

The small distance (approximately 2.5 mm) between the LED 14 and optical sensor 16 allows a nearly direct or direct vertical angle of light transmittance and absorbance and advantageously provides a more precise measurement of the pulse waveform without additional light scattering.

The on/off switch 114 can be a slid-able switch. In some embodiments, the switch 114 can be a push button, or wirelessly activated. The switch 114 may further protrude through the casing 42 to the exterior of the PWM device 2.

A pre-drilled hole 120 allows for a counter-sunk screw 122 to secure the top section 116 and the bottom section 118. In some embodiments, a latch 124 extending from the top section 116 secures the top section 116 and the bottom section 118.

Referring to FIGS. 37, 38A, 38B and 38C, in some embodiments the top section 116 is secured to the bottom section 118 with four screws 122. The counter sunk screws 122 secure the top section 116 to the bottom section 118 via the pre-drilled holes 120. Additionally, the top section 116 and bottom section 118 connect via a clamshell arrangement and latch 124. Structures on the inside of the top section 116 in FIG. 38B help hold the lithium-ion battery 64 (described in FIG. 3) within the casing 42.

Referring to FIG. 39, the sampled digital pulse waveform data 72 transmitted from the PWM device 2 may be implemented in a network environment 60. In particular, various components of an embodiment of the PWM system 28 of the present disclosure include the plurality of PWM devices 2 (e.g., Device 1 to Device N), which may interact with respective users (User 1 to User N). In some embodiments, the PWM Device 2 may communicate with a communications device 61 via Bluetooth®, near field communication (NFC), and/or radio frequency identification (RFID) transmission. The communications device 61 includes the previously described user device 34 as a subset of possible devices capable of performing the operations described herein.

In some embodiments, the PWM App 36 may reside on the communication device 61 (or user device 34) and communicate with the PWM device 2. In some embodiments, the PWM App 36 is configured to detect threshold conditions of the curve fit parameters (e.g., $A_1$-$A_6$, $y_o$ for Eq. 6; $A_i$, $y_o$ for Eq. 7, $y_o$ for Eq. 7.2) and provide alerts to the user 41 via text, e-mail, social-media updates or other communication methods. Thus the PWM device 2 and or PWM App 36 provides constant monitoring, data streaming, real-time detection and the like to reduce delay to seek treatment.

In some embodiments, the communications device 61 may transmit the sampled digital pulse waveform data 72 received from the PWM device 2 to, and communicate with, data processing servers 63, data storing servers 65, health results servers 67, and user attributes servers 69 through the communications network 60, such as a local area network (LAN), wide area network (WAN), virtual private network (VPN), peer-to-peer network, or the internet, wired or wireless, as indicated by lines 71, by sending and receiving digital data over the communications network 60.

The data processing server 63 may be a separate dedicated server running the digital data processing logic 75. The PWM data server 65 may store the sampled pulse waveform data 72 in real-time or serve as storage for older readings. The health results server 67 can interact with both the data processing server 63 and the data storing server 65 and compute or store some or all of the pulse waveform parameter calculation logic 76 and/or the health parameter calculation logic 78. The user attributes server 69 may include various user information or user data, such as the user data 90 discussed with FIGS. 6 and 11, such as age, height, weight, fitness level, ethnicity, DNA, geography, or any other personal attributes, as provided by or related to a user of the PWM device 2.

If the communication devices 61 are connected via a local or private or secured network, the devices 61 may have a separate network connection to the Internet for use by web browsers running on the devices 61. The devices 61 may also each have a web browser to connect to or communicate with the internet to obtain desired content in a standard client-server based configuration to obtain the PWM App 36 or other needed files to execute the logic of the present disclosure. The devices 61 may also have local digital storage located in the device itself (or connected directly thereto, such as an external USB connected hard drive, thumb drive or the like) for storing data, images, audio/video, documents, and the like, which may be accessed by the PWM App 36 running on the communication devices 61.

As mentioned, the communication devices 61 may also communicate with separate computers and computer servers via the network 60 for the data processing servers 63, data storing servers 65, health results servers 67, and user attributes servers 69. The servers 63, 65, 67 and 69 may be any type of computer server with the necessary software or hardware (including storage capability) for performing the functions described herein. Also, the servers 63, 65, 67 and 69 (or the functions performed thereby) may be located, individually or collectively, in a separate server on the network 60, or may be located, in whole or in part, within one (or more) of the communication devices 61 on the network 60. In addition, the data processing servers 63, data storing servers 65, health results servers 67 and user attributes servers 69, may each communicate via the network 60 with the PWM digital data processing logic 75, and with each other or any other network-enabled devices or logics as needed, to provide the functions described herein. Similarly, the communication devices 61 may each also communicate via the network 60 with the servers 63, 65, 67 and 69 and the PWM digital data processing logic 75, and any other network-enabled devices or logics necessary to perform the functions described herein.

In some embodiments, the PWM device 2 can communicate with a Bluetooth® Hub 37 via wireless transmission and perform the various communications and interactions as described in connection with the communication devices 61.

In some embodiments, the communication devices 61 communicate with a health portal computer 73 via the network 60. The health portal computer 73 contains a server running a website enabling multiple users to log in to store and/or review some or all of the PWM digital data processing results (e.g., the calculated health parameters 80). The users may securely log in through preset username and password information to ensure the privacy of their individual health parameters 80. In some embodiments, health parameters 80 may be displayed in multiple formats on the website or on the communication devices 61.

Portions of the present disclosure shown herein as being implemented outside the communications device 61, may be implemented within the communications device 61 by adding software or logic to the communications device 61, such as adding logic to the PWM App software 36 or installing a new/additional application software, firmware or hardware to perform some of the functions described herein, such as some or all of the PWM digital data processing logic 75, or other functions, logics, or processes described herein. Similarly, some or all of the digital data processing logic 75 of the present disclosure may be implemented by software in one or more of the data processing servers 63, data storing servers 65, health results servers 67, user attributes servers 69, and health portal computer 73 to perform the functions described herein, such as some or all of PWM digital data processing logic 75, or some or all of the functions performed by the PWM App software 36 in the communications device 61.

The system, computers, servers, devices and the like described herein have the necessary electronics, computer processing power, interfaces, memory, hardware, software, firmware, logic/state machines, databases, microprocessors, communication links, displays or other visual or audio user interfaces, printing devices, and any other input/output interfaces, to provide the functions or achieve the results described herein. Except as otherwise explicitly or implicitly indicated herein, process or method steps described herein may be implemented within software modules (or computer programs) executed on one or more general purpose computers. Specially designed hardware may alternatively be used to perform certain operations. Accordingly, any of the methods described herein may be performed by hardware, software, or any combination of these approaches. In addition, a computer-readable storage medium may store thereon instructions that when executed by a machine (such as a computer) result in performance according to any of the embodiments described herein.

Referring to FIGS. 40A and 40B, one position that is particularly advantageous to wear the PMW device 2 is secured flat against the anterior portion of the forearm or wrist 38. This allows for the PWM device 2 to be positioned against the radial artery 18 and provide a more precise reading of the arterial pulse compared to pulse oximetry finger readings, as well as receiving sufficient reflected light 12 from the artery 18 that is not contaminated by surrounding capillaries to produce the pulse waveform 72 with the desired data quality (or granularity or fidelity) to calculate the desired parameters, as discussed herein.

The calculated parameters from aspects of the pulse waveform data 72 may be used for numerous medical purposes. For example, the augmentation index has been shown to have predictive power of multiple cardiovascular diseases, as discussed in Michael F O'Rourke, Alfredo Pauca, Xiong-Jing Jiang, *Br J Clin Pharmacol.* 2001 June; 51(6): 507-522. Additionally, a sampled arterial pulse waveform 72 is of particular interest in clinical medicine. For example, the arterial pulse may be used to diagnose high blood pressure.

The stiffness (si) index correlates to the number of cardiovascular risk factors present. It is associated with fitness level, cardiovascular events, and mortality in patient populations with end-stage renal disease, diabetes, and metabolic syndrome. Additionally, the stiffness (si) index is informative for health factors in healthy elderly adults.

Figure 41:
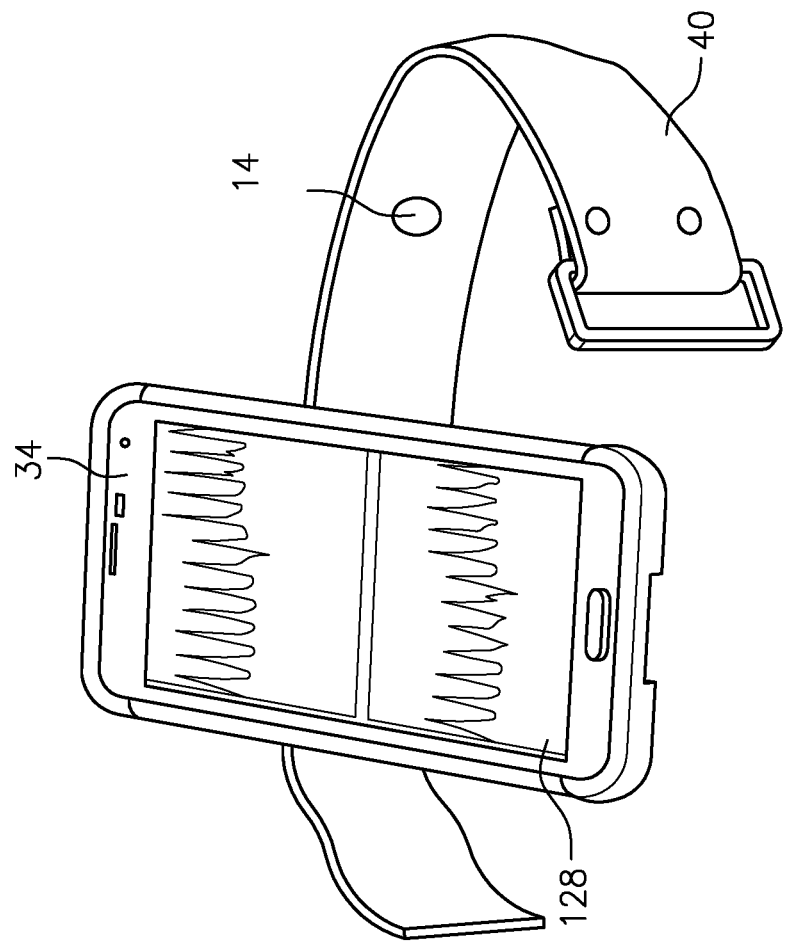
FIG. 41 is a perspective view of a user device displaying data from a PWM device within a band, in accordance with embodiments of the present disclosure.

Referring to FIG. 41, in some embodiments, the user device 34 may have a display screen 128 which can display the sampled pulse waveform 72 (FIG. 25C), as well as other manipulated waveforms and calculated parameters as discussed herein.

Figure 42A:
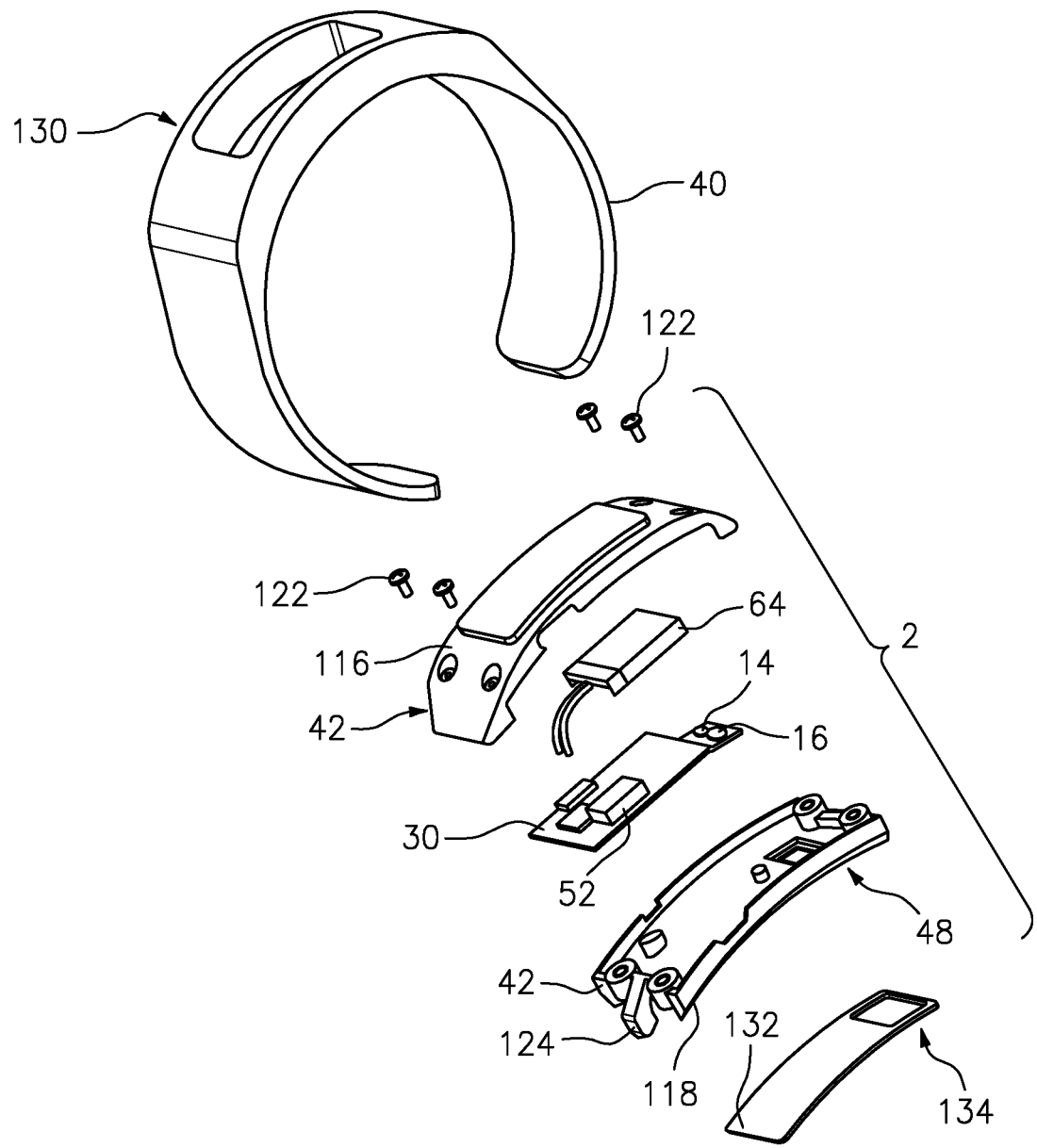
FIG. 42A is a perspective, exploded view of a PWM device including a band, casing, battery and printed circuit board, in accordance with an embodiment of the present disclosure.

Referring to FIG. 42A, in some embodiments, the band 40 has a flexible opening 130 to secure the PWM device 2 within the general footprint of the band 40. The casing 42 encloses the lithium-ion battery 64, printed circuit board 30, LED 14, optical sensor 16, data/power connection port (J2)

and other electronic components described herein via attachment screws 122. Similar to the positioning described in FIGS. 40A and 40B, the flexible opening 130 may be positioned against the anterior portion of the forearm or wrist 38. In some embodiments, the casing 42 may further include an additional metal or plastic insert 132 with a similar approximate 1.62-inch curve radius described in FIG. 36. The insert 132 has an insert opening 134 aligning with the bottom section 118 opening 48.

Figure 42B:
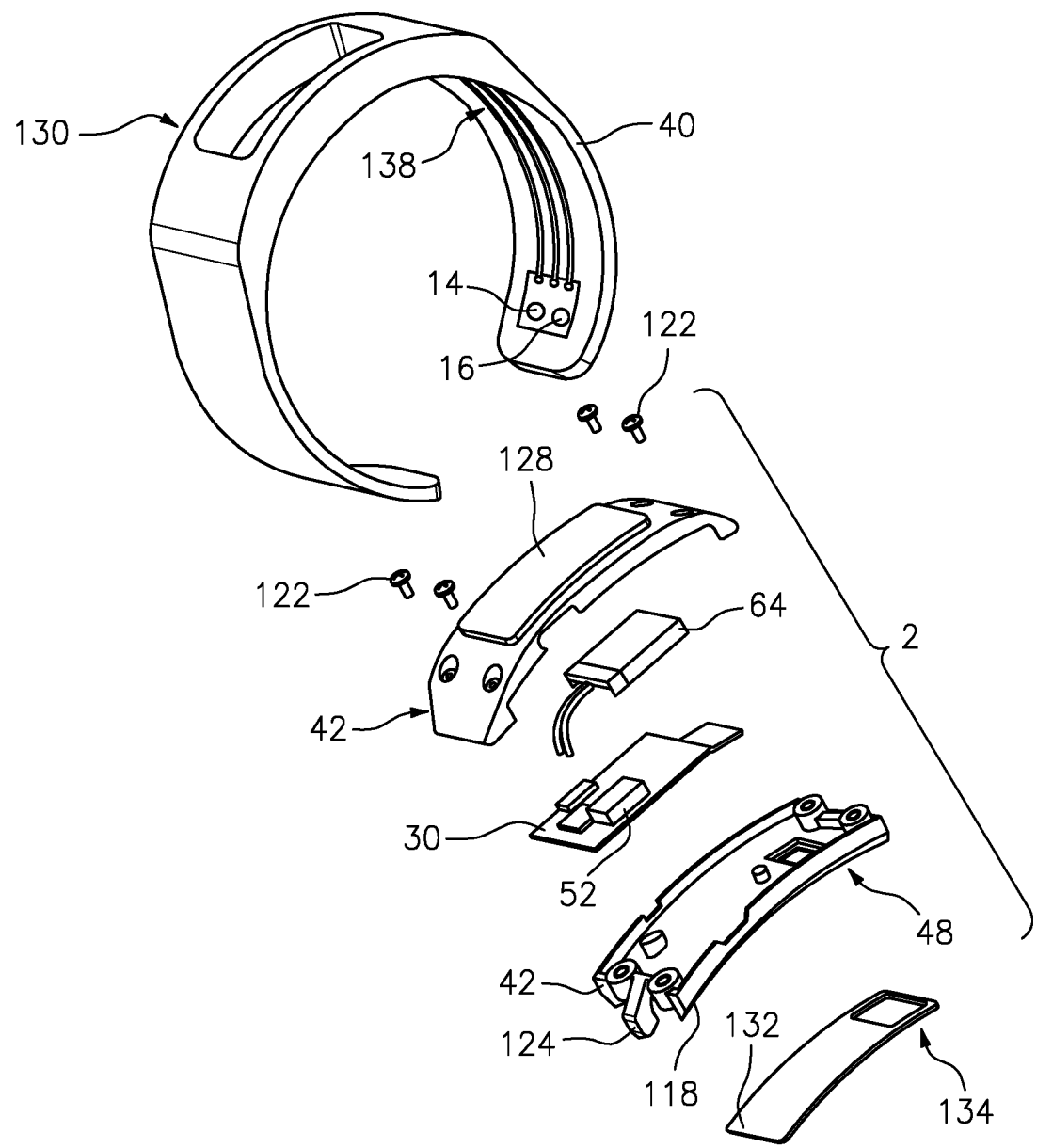
FIG. 42B is a perspective, exploded view of a PWM device including a display and an optical source/detector within a band, in accordance with embodiments of the present disclosure.

Referring to FIG. 42B, in an alternative embodiment, the LED 14 and optical sensor 16 may be disposed on the interior (or inside surface) of the band 40 with a plurality of wires 138 extending to the PWM device 2. Thus, the PWM device 2 can be worn like a wrist watch. As shown, the PWM device 2 may include a display 128 operatively connected to the circuit board 30 with the appropriate wiring and interface components or wirelessly with Bluetooth® or the like and viewable through the band opening 130. The display 128 may display the data provided by any or all of the digital data processing logic 75, pulse waveform parameter calculation logic 76 (e.g., p1, p2, n1, p3) health parameter calculation logic 78, health parameters 80 (e.g., artery resistance, augmentation index, stiffness index, blood pressure) and/or the data displayed by the user device 34 or PWM App 36, or a condensed version thereof.

Any other hardware or firmware may be used if desired provided it provides an LED source and optical sensor and provides a digital or analog pulse waveform signal described herein.

Figure 43B:
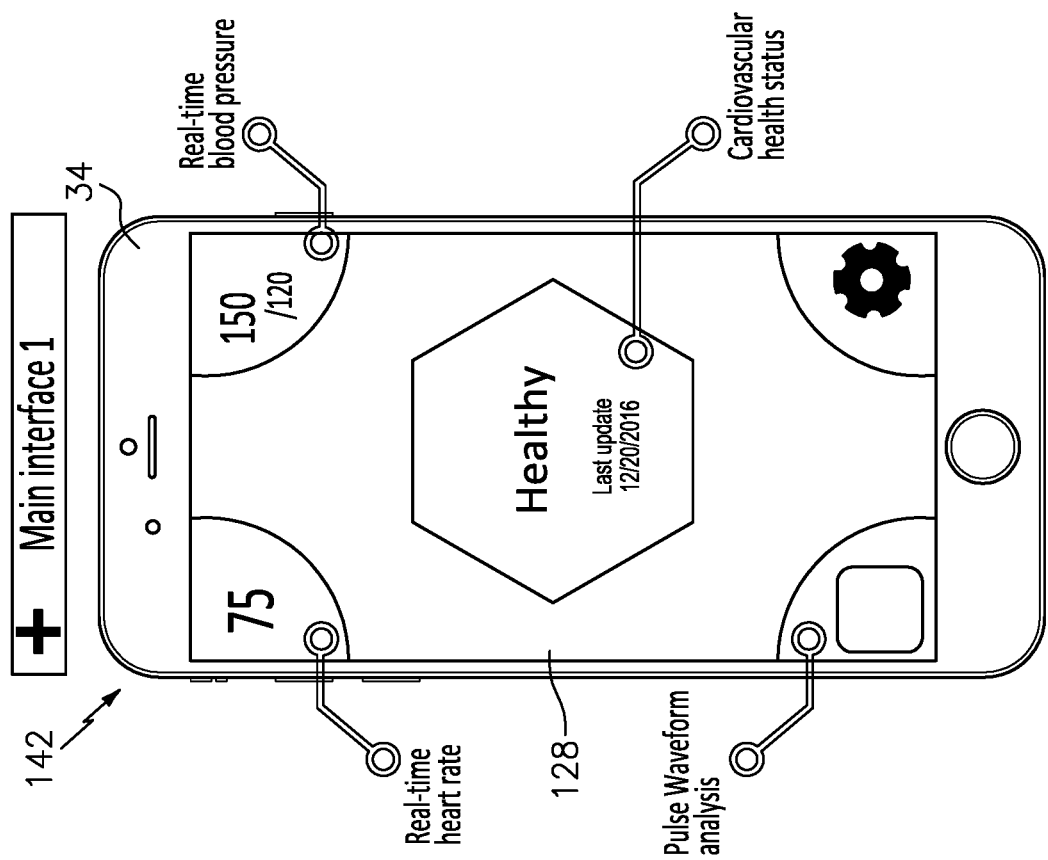
FIG. 43B is a main interface used in a PWM application implemented on a user device in accordance with embodiments of the present disclosure.
Figure 43A:
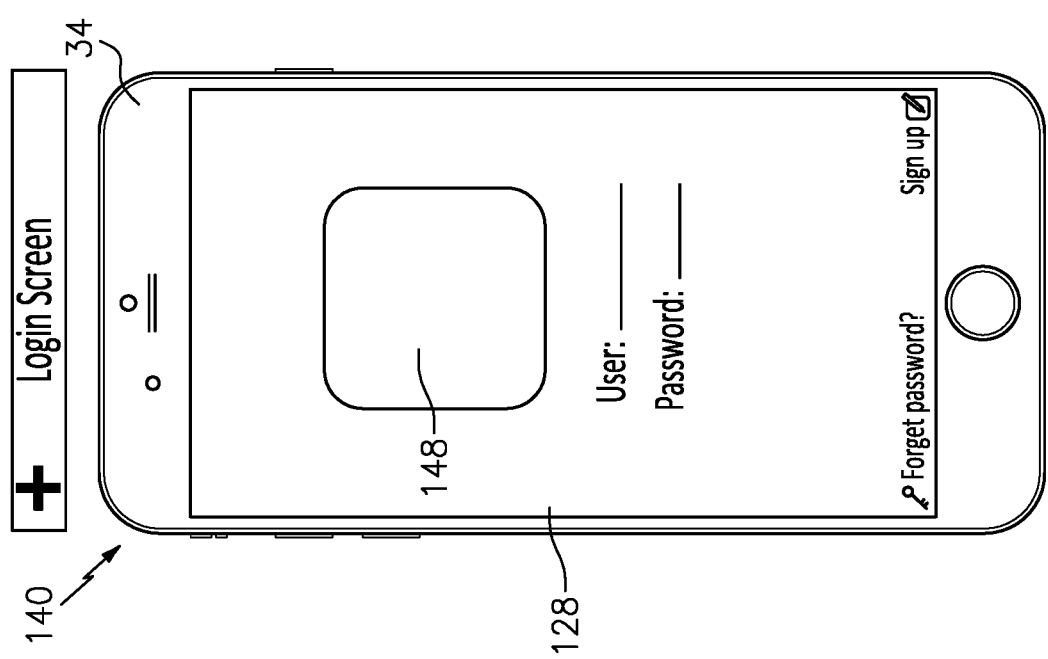
FIG. 43A is a login interface used in a PWM application implemented on a user device in accordance with embodiments of the present disclosure.
Figure 44:
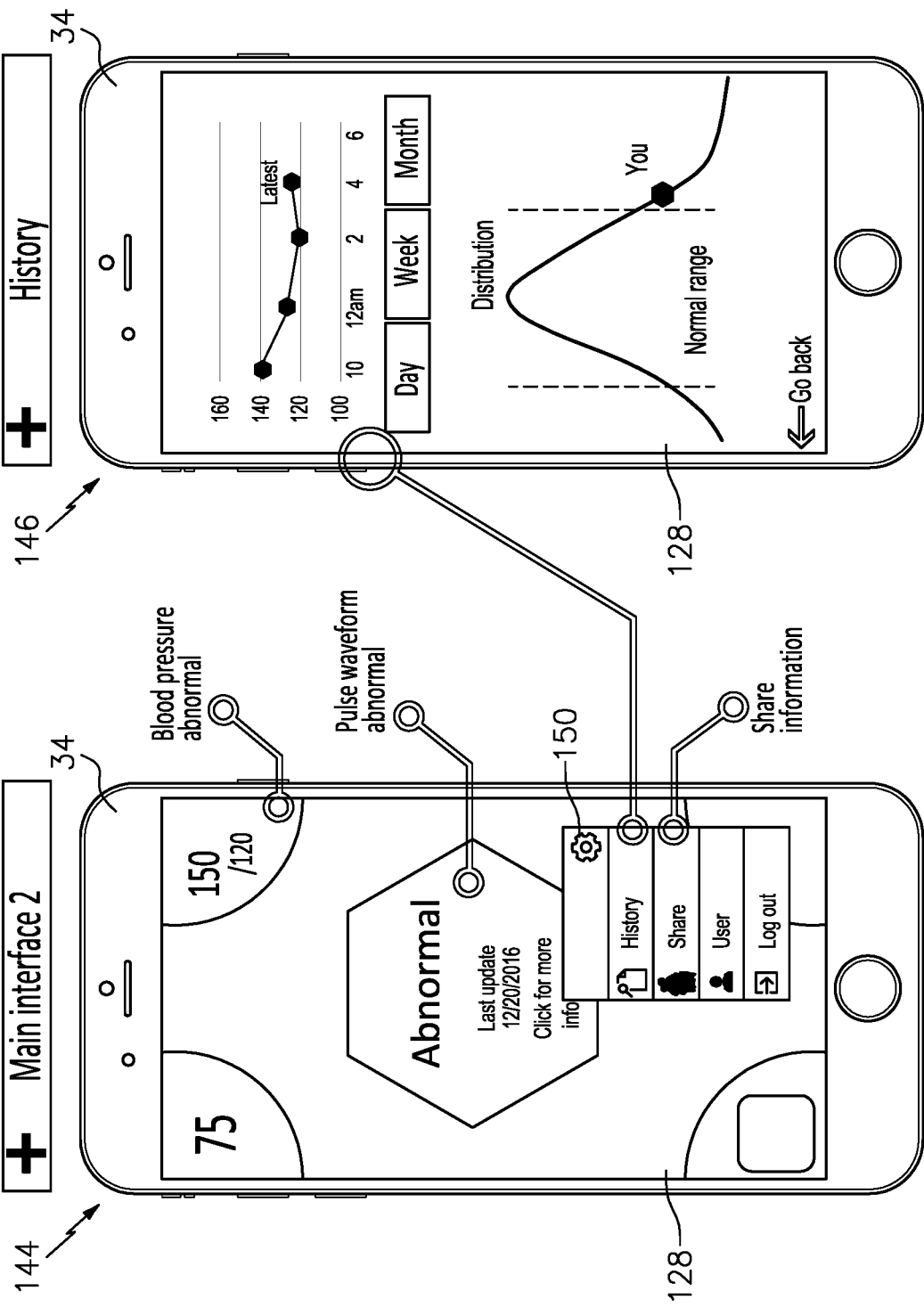
FIG. 44 is a main interface and a history interface used in a PWM application implemented on a user device in accordance with embodiments of the present disclosure.

Referring to FIGS. 43A, 43B, and 44, a login screen 140, a first main interface screen 142, a second main interface screen 144 and a history interface screen 146 are shown for displaying various pulse waveform and health attributes on the user device 34. After accessing the PWM app 36 (FIG. 1C), the login screen 140 (FIG. 43A) may include a logo 148 as well as user and password information.

After the user provides the username and password information in the login screen 140, the PWM app 36 may display the first main interface screen 142. In some embodiments, the first main interface screen 142 includes and displays real-time heart rate information, such as, for example, in the upper left corner of the user device 34 display screen 128. Real-time blood pressure information, calculated as discussed herein, may be displayed in the upper right corner of the display screen 128. Pulse waveform analysis, as discussed herein, may be displayed in the lower left corner of the display screen 128. Settings for the PWM app 36 can be displayed in the lower right corner of display screen 128, such as shown in FIG. 43B. Some or all of these screen sections may have drop-down menus 150 (shown in FIG. 44) displaying other options. The pulse waveform analysis shown in the lower left corner may display any or all of the data provided by the digital data processing logic 75 from the sampled pulse waveform data 72. For example, the data provided by the pulse waveform parameter calculation logic 76, the data provided by the health parameter calculation logic 78 (FIG. 23), and/or the calculated health parameters 80.

Referring to FIG. 44, in the center of the screen for the first main interface 142 and/or the second main interface 144, cardiovascular health status may be displayed. The cardiovascular health status may display, for example, a healthy (FIG. 43B) or an abnormal (FIG. 44) status depending on the reading and analysis of the pulse waveform data 72.

Still referring to FIGS. 43B and 44, the blood pressure information in the upper right corner of the display screen 128, may link a user to the history interface 146 and display a user's blood pressure information relative to a normal distribution curve. The blood pressure may be calculated from the pulse waveform parameters, such as (p1) and (p2) described herein. For example, from pulse waveform (and other parameters associated with the pulse waveform) the blood pressure may be mathematically computed from (p1) and (p2) or be obtained from a look up table (or the like) that correlates (p1) and (p2) (or any other parameters associated with the pulse waveform) to the blood pressure for the user of the PWM device 2.

In some embodiments, the user's blood pressure may be determined by measuring the pulse waveform parameters at (or near) the time when the user's blood pressure (BP) is measured using an external BP measurement device, such as manually by a nurse or doctor at a doctor's office, walk-in clinic, visiting nurse visit, or the like, or an automated measurement by an automated BP measurement device (cuff-based, or other form), or the like. In that case, the user may enter the BP values into the PWM App, as described herein regarding user attributes with FIG. 49. Alternatively, the BP measurement data may be sent digitally to the user's PWM App or a server accessed by the PWM App. The PWM App 36 or the Health Parameter Calculation Logic 78 may determine the relationship or correlation between the user's BP and the user's corresponding PWM parameters, such as the magnitude (or height) of P1 and P2, at the time of the BP measurement. This correlation may be improved or learned over time, e.g., by the machine learning logic 2312 (FIG. 23). The external BP measurements may be used as calibration BP user data that may occur periodically over time, depending on the frequency of the external BP measurements, to identify the individualized relationship between pulse waveform and blood pressure for a given user and a normal range for these parameters for that user.

Also, the logic may also measure "normal" patterns (or ranges) for the magnitudes of P1 and/or P2 at certain times of the day, e.g., morning, mid-day, night, and sleeping, and determine individual normative patterns for these parameters. The logic can then detect when changes occur in this normative pattern for P1 and/or P2 that may be indicative of a dangerous health event and alert the user. The logic can also detect when P1 or P2 changes greater than a danger threshold amount over a short period of time and alert the user. Such measurement may be performed on P1 or P2 individually or by taking the ratio of P1/P2 or P2/P1. Other PWM parameters (e.g., P3, n1) may also be incorporated into the above blood pressure detection logic or machine learning or identification of normative (or "normal") patterns, if desired.

By interacting with the settings disposed in the lower right corner in FIG. 44, the drop down menu 150 may appear. Options in the drop-down menu 150 include settings ("gear" icon), history, share, user and log-out. Selecting the "history" option can bring the user to the history interface 146. Selecting the "share" option can share information with another user or device, such as a doctor, health-care provider or other service. Selecting the "user" option may allow for input and/or display of a user profile such as physical attributes and the like. Selecting the "log-out" option may close the PWM App 36 or allow another user to login at the login screen 140.

Still referring to FIG. 44, the history interface 146 may show graphs (or other graphics) which track various health parameters 80, such as blood pressure, along various time inputs, such as hours, days, weeks, months, years, etc. Any other display formats or graphics or GUI's (graphical user interfaces) may be used if desired to represent the data and results described herein.

Figure 45:
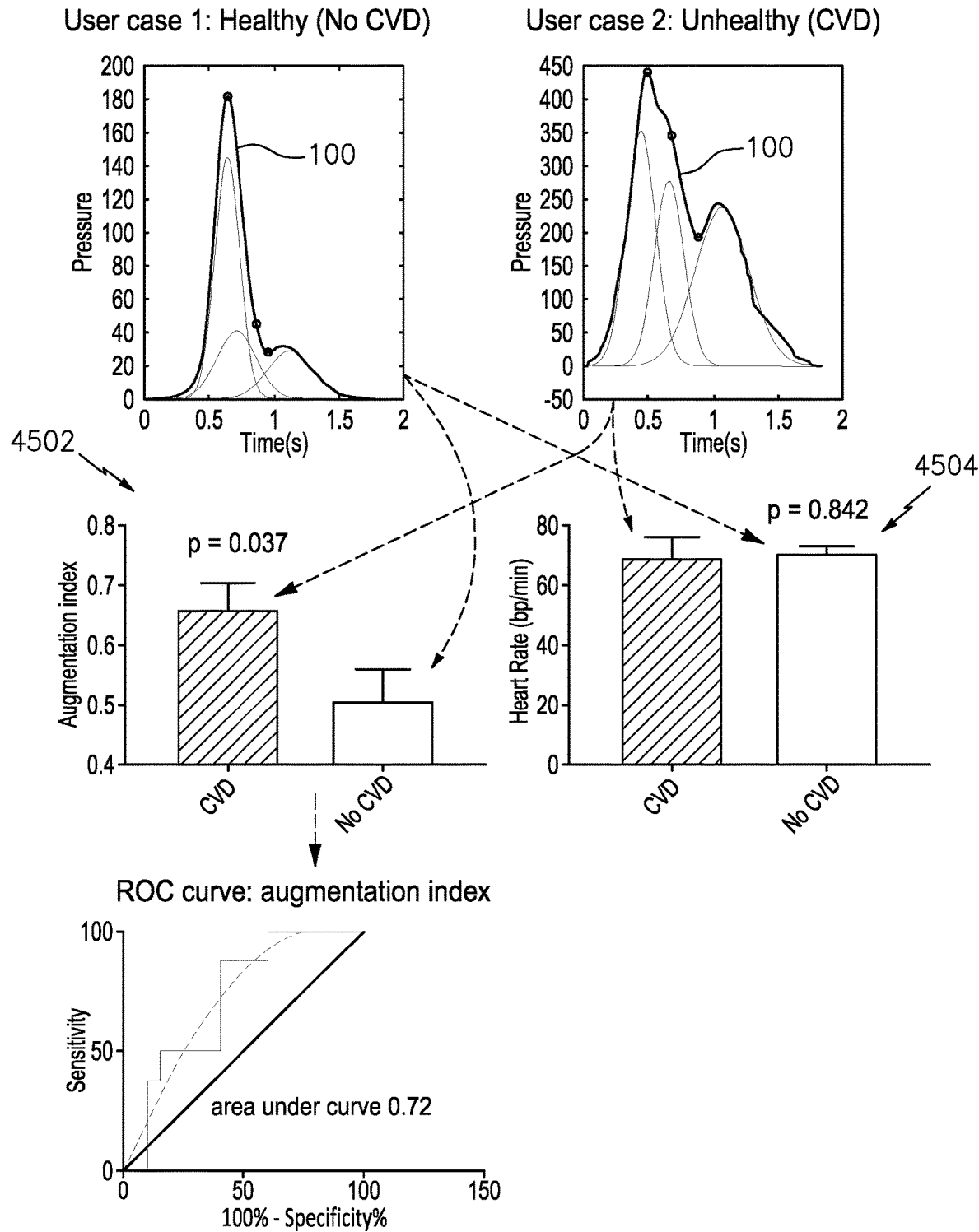
FIG. 45 is graphical depictions of exemplary results from curve-fitted pulse waveforms calculated from eight subject with cardiovascular disease and twenty subjects without cardio vascular disease.

Referring to FIG. 45, different calculations between two population groups were performed. Eight (8) subjects with cardio vascular disease (CVD) and twenty (20) subjects without CVD were split into two group populations. Averaged pulse waveforms 99 and curve fitted pulse waveforms 100 were calculated from the subjects in each population.

From the curve fitted pulse waveforms 100, the Augmentation Index (ai) of each person was calculated. The first bar graph 4502 shows that the CVD groups have, on average, a higher Augmentation Index (ai) as compared to the group without CVD. Using a Mann-Whitney test, the variance among individuals still does not account for the statistically significant higher Augmentation Index (ai), as indicated by the p value of 0.037. The p-value is a measure of probability with a value closer to zero representing a high probability that the two groups are different.

However, when comparing the heart rate between the two groups, as shown in the last bar graph 4504, there is not a distinguishable difference (p-value of 0.842). Thus, the Augmentation Index of the present disclosure is capable of distinguishing a CVD group from a non-CVD group, while commercially available devices that measure heart rate would not be able to make such a determination. Accordingly, the present disclosure provides a diagnostic tool, based on the Augmentation Index, to determine health status, such as cardiovascular disease.

An ROC curve, as shown in FIG. 45, is another way of showing the difference between two groups. By using Augmentation Index (ai) as a diagnostic tool, there needs to be a threshold, above and below which a determination of normal or abnormal, (i.e. has cardiovascular disease) can be determined. The ROC curve is a way to show that if the threshold is varied, what is the performance for disease prognostication. The area under the ROC curve shows the diagnostic value of the augmentation index for CVD.

Referring to FIG. 46, possible pulse waveform irregularities and diseases or maladies associated with the irregularities can be discerned based on the shape of the calculated pulse waveform (and/or parameters associated therewith, as discussed herein) compared to the ideal or normal or theoretical pulse waveform 74 and displayed, such as on display 128 on the user device 34, 61 or the PWM device 2 itself. Additionally, the possible pulse waveform irregularities and diseases or maladies associated with the irregularities may be displayed on the PWM App 36, as further described with regards to FIGS. 48 and 49. For example, diseases such as heart failure, hypovolemia, severe aortic stenosis, fever, anemia, hyperthyroidism, aortic regurgitation, bradycardia, heart block, atherosclerosis, hypertrophic cardiomyopathy and left ventricular failure can be deduced based on the variation of the pulse waveform from a normal pulse waveform such as described in Zhaopeng Fan, Gong Zhang and Simon Liao (2011). *Pulse Wave Analysis, Advanced Biomedical Engineering*, Dr. Gaetano Gargiulo (Ed.), ISBN: 978-953-307-555-6 which is incorporated herein by reference to the extent necessary to understand the present disclosure.

Referring to FIGS. 47A, 47B, 47C, 47D, 47E, 47F, 47G and 47H, different optical sensor configurations are shown. For example, multiple sensors (16, 16a, 16b, 16c, 16d) and multiple LEDs (14, 14a, 14b, 14c) may be used to provide enhanced source (or incident) light 4, and thus enhanced reflected light, and provide substantially uniform distribution of reflected light on the sensor. Additionally, the quantity and configuration of the sensors 16, 16a, 16b, 16c may provide enhanced detection characteristics. Additionally, different locations can provide redundancy and/or greater fidelity/granularity. Other configurations may be used provided they provide the performance described herein. Each of FIGS. 47A, 47B, 47C, 47D, 47E, 47F and 47G can be referred to herein as a PWM sensing unit.

In some embodiments the PWM sensing unit (or PWM sensing units) may be positioned in the flow direction of blood within an artery. In some embodiments the PWM sensing unit (or PWM sensing units) may be positioned perpendicular to the flow direction of blood within an artery. In some embodiments, the PWM sensing unit may consist of two sensors 16, 16a surrounding an LED 14, as shown in FIG. 47B. In some embodiments, LEDs 14 and 14a provide source light from either side of a sensor 16 in a sensing unit, as shown in FIGS. 47C and 47E. In some embodiments, a substrate 31A may contain multiple sensing units (or circuit boards 31) arranged in an array or matrix (2-dimensional or 1-dimensional), as shown in FIG. 47H. The contemplated configurations may be used to maximize exposure of the sensor (e.g., 16, 16a, 16b, 16d in FIG. 47F or 16 in FIGS. 47C, 47E and 47G) to substantially uniform reflected light from the body (or blood vessel).

In FIG. 47F, there are four sensors (16, 16a, 16b, 16c) surrounding a single LED 14 source, and in FIG. 47G, there are four sources (14, 14a, 14b, 14c) surrounding a single sensor 16.

Additionally, as shown in FIG. 47H, multiple sensing units are arranged on the substrate 31A and can measure sampled pulse waveform data 72 at at least two different artery locations. The separate spatial locations of measurement advantageously allow for other health parameters, such as wave velocity (PWV), to be calculated. Additional health parameters and information may be determined by utilizing different (or multiple) artery locations, are contemplated within the scope of the present disclosure.

In particular, in some embodiments, the sensing unit arrangements on a layout 4702 having two (or more) sensing units in series, and may be positioned in the flow direction of blood within an artery (e.g., left/right in FIG. 47 H). In some embodiments, the sensing unit arrangements on a layout 4704 may be positioned perpendicular to the flow direction of blood within an artery (e.g., up/down in FIG. 47H). In some embodiments, both layout configurations 4702, 4704 may be utilized in the same substrate 31A to provide the PWM and health parameters, and information. Any configuration or combination of configurations or orientations of the sensing units shown in FIGS. 47A, 47B, 47C, 47D, 47E, 47F, 47G and/or 47H may be utilized on individual or separate substrates or circuit boards to provide the PWM and health parameters and information described herein or other health parameters or information.

Figure 48:
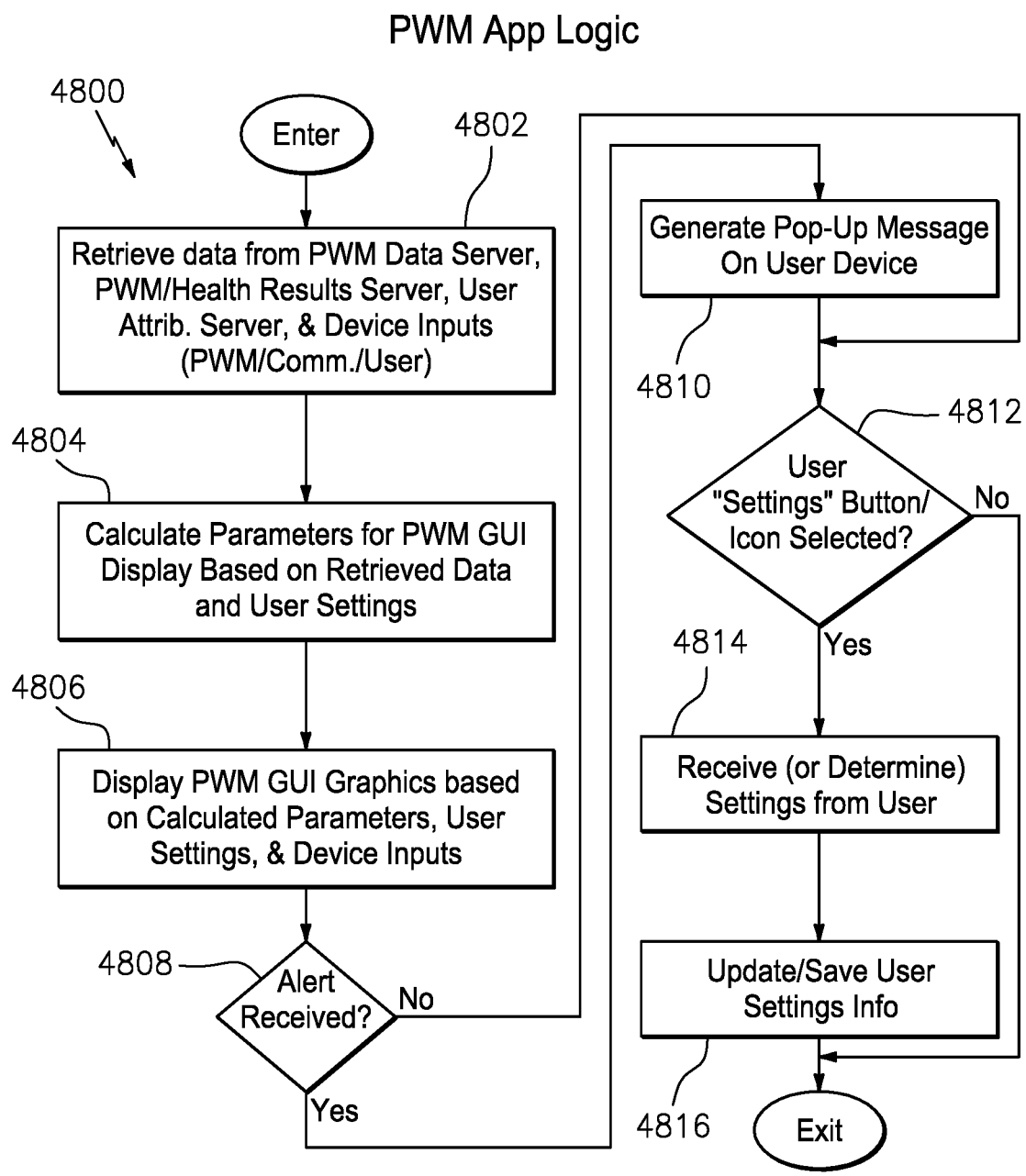
FIG. 48 is a flow diagram of a PWM software application (PWM App), in accordance with embodiments of the present disclosure.

Referring to FIG. 48, a flow diagram 4800 illustrates one embodiment of a process or logic of the present disclosure for providing, among other things, a graphic user interface (GUI) to the user 41 on the display 38 of the user/communication device 34,61 (FIGS. 1C, 39), for receiving and displaying PWM alerts, and for allowing the user to set preferences, settings and the like, which may be implemented by the PWM App Software Logic 36 (FIGS. 1C, 39). The process 4800 runs when the PWM App 36 is launched and begins at a block 4802, which retrieves data from the PWM Data Server 65 (FIG. 39), the PWM/Health Results Server 67, the User Attribute Server 69, as well as input data from the user 41 via the user device 34,61 user input (e.g., touch screen display, mouse or other user input interface).

Next, a block 4804 uses the data retrieved in the block 4802 (including the user settings) to calculate the needed parameters to display the PWM GUI on the display 128 of the user device 34,61 (FIGS. 1C, 39). Next, a block 4806 displays the graphics for the PWM GUI on the display 128 of the user device 34. In particular, the Heart Rate, Blood Pressure, Healthy/Abnormal Status, Normal Distribution Graph, BP Chart/details, PWM Graph Details, PWM Parameters, Health Parameters, and any other display components, images, or icons discussed or shown herein for the PWM GUI.

Next, a block 4808 determines whether a PWM Alert has been received. If YES, a block 4810 generates a pop-up message on the user device 34 display 128 indicating a PWM Alert has occurred and the user 41 can then go to the PWM GUI screen 128 to view the alert. Next, or if the result of block 4808 is NO, a block 4812 checks if the "Settings" (gear) icon has been selected on the screen 128. If YES, a block 4814 receives input settings data from the user 41, e.g., for display format, user attributes, and alert settings (as discussed herein). Next, a block 4816 saves (or updates) the settings info, based on the selections made by the user, e.g., on the device 34 or on the User Attributes Server 69 (FIG. 39), and the process exits. For example, some of the PWM App settings data, such as the User Attributes and the Alert Settings, may be stored in a table or database on the User Attributes Server 69 (FIG. 39), and other settings data may be stored locally on the User Device 34, such as the Display Format settings. Any other data storage arrangement that performs the functions of the present disclosure may be used if desired.

Referring to FIGS. 43A, 43B, and 44, in the lower right portion of the display screen 128 is a user settings menu ("gear") icon, which, when selected, allows the user to select various attributes and features associated with the PWM App software 36, to perform the functions described herein, such as various display options, defaults, and the like, as well as to provide information about the user (user attributes) and for setting PWM alerts, or for other purposes as described hereinafter. In particular, referring to FIG. 49, when the Settings "gear" icon option (FIG. 44) is selected, a new GUI pop-up menu 4900 may appear on the display 128 (FIG. 44), having a series of options or user settings to select. More specifically, the user settings are shown in three sections, a display format section 4902, a user attributes section 4904, and an alert settings section 4906. In the display format section 4902, checkboxes are provided to indicate which of the display items should be displayed by the App on the screen. Also, there may be an option to display aggregated data from other users and to filter the data based on age, health history or medical conditions, location, physical conditioning, and the like. There may also be options (not shown) to select screen locations (e.g., top, bottom, left, right), size, and colors for the various display items, as well as types of graphs or charts or data displays (line, bar, pie, etc.). Other display format settings may be provided if desired, or as needed or discussed herein, to perform the functions of the present disclosure.

The User Attributes section 4904 allows the user to provide information about himself/herself, which may be saved in a table or database in the User Attributes Server 69 (FIG. 39) for use in determining user personalized thresholds for normal/abnormal status, medical conditions, alerts, and for other purposes, as described herein.

In particular, the User Attributes section 4904 has fields or checkboxes or corresponding (single or multi-pick) dropdown menus for: date of birth, male/female, age group, home address/location, health history, physical conditioning, latest blood pressure data and date, and allow receipt of data (e.g., BP, or other data). In particular, a multi-pick dropdown menu is provided to allow the user to select all the health history information applicable for the user, e.g., types of medical conditions (e.g., asthma, heart disease, etc.) and currently medications being used. There is also a multi-pick dropdown menu provided to allow the user to select all the healthy conditioning activities the user does, e.g., run, lift, bike, meditate, yoga, organic foods, and the like). Also, a checkbox and fields are provided for the user to enter the last blood pressure (BP) measurement obtained and the date (and optionally time) it was measured. This BP information may also be automatically populated digitally by the PWM App 36 and/or by the PWM Processing Logic 75, if the user agrees to receive external BP data by checking the corresponding checkbox. In that case, when the user has his/her blood pressure measured, the measurement may be sent electronically and/or stored in the appropriate location in the User Attributes Server 69, or other location that allows it to be used by the PWM App 36 and/or by the PWM Processing Logic 75.

The Alert Settings section 4906 allows the user to set-up alerts for certain types of events relating to data collected and analyzed by the PWM App 36 and/or by the PWM Processing Logic 75. In particular, a checkbox is provided to turn on (or off) alerts that may be generated by the logic of the present disclosure, as discussed herein. A checkbox is also provided to allow the user to select what type of events to receive alerts for, such as when abnormal status or data values are detected for one or more of a list of checkable items, e.g., BP, PWM Parameters, Health Parameters, Healthy/Abnormal Status, Pulse Rate, Urgent Health Event (or highly likely event based on data collected and analyzed by the present disclosure), such as heart attack, stroke, organ failure, other. A checkbox is also provided to send an alert (or status) to one or more individuals or services, such as: Doctor, 911 service, Hospital, Family/Friend, and the like. Also, negative preferences or exclusionary criteria may be used if desired, e.g., do NOT send me an alert when certain events or items happen. Other alert settings and preferences may be used if desired, or as needed or discussed herein, to perform the functions of the present disclosure.

Any software, hardware, or firmware, including algorithms and other techniques for extracting the pulse waveforms (using time domain or frequency domain) from the collected data may be used if desired provided it provides a pulse waveform as described herein.

A pulse waveform can reflect health conditions of the human cardiovascular system. While certain parameters derived from a pulse waveform have been applied in clinical and research settings, these principles have not been applied outside of a clinical setting. Additionally, real-time measurement and analysis of a pulse waveform is not currently available in any device. However, the device of the present disclosure enables measurement and analysis of the pulse waveform anywhere at anytime and in real-time.

The present disclosure provides for measurement of substantially (or a substantial portion of) the entire pressure pulse waveform curve/profile or a sufficient portion of the pulse waveform curve/profile to determine (or calculate or identify) any parameters that can be derived therefrom such as those described herein. The measurement techniques discussed herein produce a pulse waveform of sufficient signal quality to determine p1, p2, n1, p3, T1, $\Delta T$, $A_{P1}$ and $A_{P2}$, as well as to determine the entire (or substantially the entire) pulse waveform curve/profile and any parameters that can be derived therefrom. This is a significant improvement over current technology, which provides the ability to determine primarily the main peak P1. As discussed herein, obtaining the entire pulse waveform with sufficient fidelity is required to calculate many of these parameters.

Current pulse waveform measurement tools are cumbersome in size, difficult to use, and lack automated analysis capability.

An advantage of the PWM device 2 or system 28 of the present disclosure is the fidelity, stability and reliability of the pulse waveform data 72 when sampled above about 100 Hz frequency and the corresponding parameters determined/calculated therefrom, as discussed herein.

Compared to other heartrate measuring devices such as Fitbit®, Jawbone®, Apple Watch®, and the like, the PWM device 2 or system 28 of present disclosure provides a different sampling rate, measuring site and readout (i.e., an arterial pulse waveform).

Also, compared to fingertip photoplethysmogram, the PWM device 2 or system 28 of the present disclosure provides a different transmitted wavelength, measuring site, data processing and displayed parameters.

In addition, compared to applanation tonometry, which is typically only employed in clinical use, the PWM device 2 or system 28 of present disclosure provides a smaller, portable reflection measurement and not a pressure measurement.

Although various above described embodiments depict a wearable and portable PWM device, it is understood that the PWM device 2 may be added to known probe or pressure devices (i.e. applanation tonometry devices) for measuring PWM or health parameters and connected to an instrument in a wired fashion or wirelessly. For example, the PWM device may be placed on the skin to conduct pulse waveform measurements and removed after a sufficient period of time.

Another advantage of the PWM device 2 or system 28 of the present disclosure is the small size and energy requirement of the PWM device 2. Due to its size it may be incorporated into bracelets, wristbands and/or clothing such as sweatshirts, long sleeve shirts and the like.

More specifically, the PWM device 2 or system 28 of the present disclosure may be integrated with other devices, for example an Apple Watch®, to display any or all of the data from the digital data processing logic 75, health parameter calculation logic 78, health parameters 80 or a condensed version thereof.

Another advantage of the PWM device 2, system 28 and/or PWM App 36 of the present disclosure is that the PWM device 2, system 28 and/or PWM App 36 may be configured to detect threshold conditions of the PWM parameters (or other health parameters 80 (e.g. artery resistance, augmentation index, stiffness index, blood pressure)) and provide alerts to the user via text, e-mail, social-media updates or other communication methods. Thus, constant monitoring, data streaming, real-time detection and the like may reduce delay to seek treatment, help to manage existing conditions, and alert the user in real-time. Also, the present disclosure allows for receiving comparison information against other users who share their PWM data.

Although the device and system described above have a 2.5 mm distance between the LED 14 and optical sensor 16, larger distances and greater reflectance angles are also contemplated within the scope of the present disclosure.

As will be recognized by those of ordinary skill in the pertinent art, numerous modifications and substitutions can be made to the above-described embodiments of the present disclosure without departing from the scope of the disclosure. Accordingly, the preceding portion of this specification is to be taken in an illustrative, as opposed to a limiting, sense.

Although the disclosure has been described herein using exemplary techniques, algorithms, or processes for implementing the present disclosure, it should be understood by those skilled in the art that other techniques, algorithms and processes or other combinations and sequences of the techniques, algorithms and processes described herein may be used or performed that achieve the same function(s) and result(s) described herein and which are included within the scope of the present disclosure.

Any process descriptions, steps, or blocks in process or logic flow diagrams provided herein indicate one potential implementation, do not imply a fixed order, and alternate implementations are included within the scope of the preferred embodiments of the systems and methods described herein in which functions or steps may be deleted or performed out of order from that shown or discussed, including substantially concurrently or in reverse order, depending on the functionality involved, as would be understood by those reasonably skilled in the art.

It is noted that the Figures are to be taken as an illustrative example only, and are not to scale.

All cited references are incorporated in their entirety to the extent needed to understand the present disclosure, and to the extent permitted by applicable law.

It should be understood that, unless otherwise explicitly or implicitly indicated herein, any of the features, characteristics, alternatives or modifications described regarding a particular embodiment herein may also be applied, used, or incorporated with any other embodiment described herein.

Conditional language, such as, among others, "can," "could," "might," or "may," unless specifically stated otherwise, or otherwise understood within the context as used, is generally intended to convey that certain embodiments could include, but do not require, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Although the invention has been described and illustrated with respect to exemplary embodiments thereof, the foregoing and various other additions and omissions may be made therein and thereto without departing from the spirit and scope of the present disclosure.

What is claimed is:

1. A, computer-based wearable pressure pulse waveform measurement device for determining one or more health parameters or health conditions, comprising:
   a first light source adapted to transmit light to a blood carrying artery at a measurement location;
   an optical sensor adapted to receive a reflected light in response to the transmitted light from the blood carrying artery;
   a processor configured to measure the reflected light and to convert the reflected light into measured digital pulse waveform measurement (PWM) data indicative of an entire shape of one cycle of the pressure pulse waveform in the blood carrying artery at the measurement location, by performing a Fast Fourier Transform (FFT) or a convolution on the measured digital pulse waveform data and performing curve fitting to provide the entire shape of one cycle of the pressure pulse waveform;

the processor further configured to determine pulse waveform parameters from the entire shape of one cycle of the measured digital pulse waveform;

the processor further configured to receive digital reference pulse waveform data indicative of normal and abnormal PWM data, and configured to determine continuously in real-time one or more health parameters or health conditions indicative of an abnormal PWM, using the pulse waveform parameters, the entire shape of one cycle of the measured digital PWM data and an entire shape of one cycle of the digital reference pulse waveform data; and the processor further configured to generate a PWM alert based on the determined one or more health parameters or health conditions indicative of an abnormal PWM and to provide the PWM alert to a user device or to the wearable device.

2. The device of claim 1, wherein the light from the first light source is transmitted to a radial artery.

3. The device of claim 1, wherein the first light source comprises an LED (Light Emitting Diode) having a wavelength in the range of 500-640 nm.

4. The device of claim 1 further comprising a second light source adapted to transmit light to the blood carrying artery at the measurement location, and wherein the optical sensor is disposed between the first and second light sources, and wherein the reflected light being in response to light from the first and second light sources such that the reflected light is distributed substantially uniformly across the sensor.

5. The device of claim 1, wherein the processor measures the reflected light at a sampling rate in the range of 100-500 Hz.

6. The device of claim 1, wherein the at least one health parameter, comprises at least one of: stiffness index, mean arterial pressure, stroke volume, augmentation index, blood pressure and heart rate.

7. The device of claim 1, wherein the processor is configured to identify a period from the measured digital pulse waveform measurement (PWM) data by finding the time between pulses obtained by at least one of time domain convolution and frequency domain analysis.

8. A computer-based method for determining one or more health parameters or health conditions by measuring a pressure pulse waveform of a user using a portable, wearable device, the method comprising:

providing an optical source light from at least one light source disposed in the wearable device, the optical source light being incident on a blood carrying artery at a measurement location on the user;

measuring a reflected light, with an optical sensor disposed in the device, in response to the optical source light, the reflected light being indicative of the pressure pulse waveform associated within the blood carrying artery at the measurement location;

converting the reflected light into measured digital pulse waveform measurement (PWM) data, indicative of an entire shape of one cycle of the pressure pulse waveform in the blood carrying artery of the user at the measurement location, the converting comprising performing a Fast Fourier Transform (FFT) or a convolution on the measured digital pulse waveform data and performing curve fitting to provide the entire shape of one cycle of the pressure pulse waveform;

determining pulse waveform parameters from the entire shape of one cycle of the measured digital pulse waveform;

receiving digital reference pulse waveform data indicative of normal and abnormal PWM data;

determining, continuously in real-time by the computer, one or more of the health parameters or health conditions indicative of an abnormal PWM, using the pulse waveform parameters, the entire shape of one cycle of the measured digital PWM data to and an entire shape of one cycle of the digital reference pulse waveform data;

generating a PWM alert based on the determining of the one or more health parameters or health conditions indicative of an abnormal PWM; and providing the PWM alert to a user device or to the wearable device.

9. The method of claim 8 further comprising: identifying a period from the PWM data by finding a time between pulses obtained by at least one of: time domain convolution and frequency domain analysis.

10. The method of claim 8 further comprising:

extracting pulse waveform segments from the PWM data; and averaging the extracted pulse waveform segments, as averaged pulse waveform segments.

11. The method of claim 10, wherein the pulse waveform segments are extracted by finding a time between pulses obtained by at least one of time domain convolution and frequency domain analysis.

12. The method of claim 10, wherein the curve fitting comprises performing a mathematical curve fit to the averaged pulse waveform segments to obtain a fitted pulse waveform curve.

13. The method of claim 12, wherein the mathematical curve fitting used to obtain the fitted pulse waveform curve comprises at least one of: exponential and Gaussian.

14. The method of claim 8, wherein the convolution comprises convolving the PWM data with a standard pulse waveform curve.

15. The method of claim 14, wherein the convolving is repeated multiple times in an iterative fashion.

16. The method of claim 8, wherein the at least one light source comprises an LED (Light Emitting Diode) having a wavelength in the range of 500-640 nm.

17. The device of claim 8 wherein the at least one light source comprises a plurality of light sources adapted to transmit light to the blood carrying artery at the measurement location, and wherein the reflected light being in response to light from the plurality of sources such that the reflected light is distributed across the optical sensor.

18. The device of claim 8 wherein the at least one light source comprises a first light source and a second light source adapted to transmit light to the blood carrying artery at the measurement location, and wherein the optical sensor is disposed between the first and second light sources, and wherein the reflected light being in response to the optical source light from the first and second light sources such that the reflected light is distributed across the optical sensor.

19. The method of claim 8, wherein the measuring the reflected light occurs at a sampling rate in the range of 100-500 Hz.

20. The method of claim 8, further comprising providing the PWM alert when the at least one health parameter is in an unsafe range.

21. The method of claim 8, wherein the light source is transmitted to a radial artery of the user.

22. The method of claim 8, wherein the wearable device is worn on the user's wrist.

23. The method of claim 8, wherein the health conditions comprises a normal or abnormal condition of the user.

24. The method of claim 8, wherein the reference pulse waveform data is derived from at least one of: PWM curves from other users and theoretical pulse waveform data.

25. The method of claim 8, wherein the health parameters comprises at least one of: stiffness index, mean arterial pressure, stroke volume, augmentation index, blood pressure and heart rate.

* * * * *